United States Patent
Helms et al.

(10) Patent No.: US 10,727,488 B2
(45) Date of Patent: Jul. 28, 2020

(54) REDOX MEDIATORS FOR METAL-SULFUR BATTERIES

(71) Applicants: The Regents of the University of California, Oakland, CA (US); The Massachusetts Institute of Technology, Cambridge, MA (US)

(72) Inventors: Brett A. Helms, San Francisco, CA (US); Peter D. Frischmann, Berkeley, CA (US); Yet-Ming Chiang, Cambridge, MA (US); Frank Y. Fan, Cambridge, MA (US); Sean E. Doris, San Francisco, CA (US); Laura C. H. Gerber, Berkeley, CA (US)

(73) Assignees: The Massachusetts Institute of Technology, Cambridge, MA (US); The Regents of the University of California, Oakland, CA (US)

( * ) Notice: Subject to any disclaimer, the term of this patent is extended or adjusted under 35 U.S.C. 154(b) by 28 days.

(21) Appl. No.: 15/502,479

(22) PCT Filed: Aug. 11, 2015

(86) PCT No.: PCT/US2015/044637
§ 371 (c)(1),
(2) Date: Feb. 7, 2017

(87) PCT Pub. No.: WO2016/025467
PCT Pub. Date: Feb. 18, 2016

(65) Prior Publication Data
US 2017/0222226 A1    Aug. 3, 2017

Related U.S. Application Data

(60) Provisional application No. 62/154,040, filed on Apr. 28, 2015, provisional application No. 62/136,348, filed on Mar. 20, 2015, provisional application No. 62/036,056, filed on Aug. 11, 2014.

(51) Int. Cl.
| | | |
|---|---|---|
| *H01M 4/62* | (2006.01) |
| *H01M 4/38* | (2006.01) |
| *H01M 4/58* | (2010.01) |
| *H01M 10/052* | (2010.01) |
| *C07D 209/58* | (2006.01) |
| *C07D 471/06* | (2006.01) |
| *H01M 8/18* | (2006.01) |
| *H01M 4/60* | (2006.01) |

(52) U.S. Cl.
CPC ............ *H01M 4/62* (2013.01); *C07D 209/58* (2013.01); *C07D 471/06* (2013.01); *H01M 4/382* (2013.01); *H01M 4/5815* (2013.01); *H01M 8/188* (2013.01); *H01M 10/052* (2013.01); *H01M 4/606* (2013.01); *H01M 2300/0028* (2013.01)

(58) Field of Classification Search
CPC ............ H01M 4/62; H01M 4/38; H01M 4/58; H01M 8/18; H01M 4/382; H01M 4/5815; H01M 8/188; H01M 2300/0028; C07D 209/58; C07D 471/06
See application file for complete search history.

(56) References Cited

U.S. PATENT DOCUMENTS

| | | | | |
|---|---|---|---|---|
| 2009/0211726 A1* | 8/2009 | Bank | ...................... | C09K 5/063 |
| | | | | 165/10 |
| 2009/0251849 A1* | 10/2009 | Yamagishi | ............. | H01G 9/038 |
| | | | | 361/502 |
| 2011/0189520 A1* | 8/2011 | Carter | ................. | B60L 11/1879 |
| | | | | 429/107 |
| 2014/0117321 A1 | 5/2014 | Lim et al. | | |

FOREIGN PATENT DOCUMENTS

| | | | |
|---|---|---|---|
| JP | 2004/238301 | * | 8/2004 |
| JP | 2004/238301 A1 | | 8/2004 |
| JP | 2004238301 | * | 8/2004 |
| KR | 2013/0135135 A1 | | 12/2013 |
| KR | 20130135135 | * | 12/2013 |
| WO | 2014/121276 A2 | | 8/2014 |
| WO | WO 2014121276 | * | 8/2014 |

OTHER PUBLICATIONS

Chen et all, Chem. Mater. 2005, 17, 2208-2215 (Year: 2005).*
JP2004238301MT (Year: 2004).*
Fan, et al., "Polysulfide Flow Batteries Enabled by Percolating Nanoscale Conductor Networks," Nano Lett. 2014, 14, 2210-2218.
International Search Report dated Nov. 27, 2015, issued in PCT/US2015/044637.

* cited by examiner

*Primary Examiner* — Alexander Usyatinsky
(74) *Attorney, Agent, or Firm* — Kilpatrick Townsend & Stockton LLP

(57) ABSTRACT

Metal-sulfur energy storage devices also comprising new redox mediator compounds are described.

11 Claims, 27 Drawing Sheets

Figure 17

| Molecule | $E_{ea}$ | $E_i$ | Molecule | $E_{ea}$ | $E_i$ |
| --- | --- | --- | --- | --- | --- |
| SUM 1 | 0.19 | 4.23 | CDI 20 | 2.25 | 4.75 |
| triphenylene | 0.31 | 4.62 | CDI 26 | 2.26 | 4.83 |
| naphthalene | 0.32 | 4.57 | CIA | 2.26 | 4.79 |
| HEL 1 | 0.65 | 4.24 | DBCDI 2 | 2.27 | 4.28 |
| CAN 3 | 0.74 | NA | CDI 24 | 2.29 | 4.86 |
| HBC 1 | 0.76 | 4.02 | CDI 5 | 2.29 | 4.87 |
| HEL 2 | 0.80 | 4.21 | CDI 7 | 2.30 | 4.89 |
| CAN 1 | 0.92 | 4.70 | CDI 6 | 2.31 | 4.89 |
| anthracene | 0.93 | 3.99 | PBI 13 | 2.33 | 4.70 |
| perylene | 1.22 | 3.72 | CDI 25 | 2.33 | 4.91 |
| terrylene | 1.60 | 3.35 | DBCDI 3 | 2.34 | 4.45 |
| pentacene | 1.63 | 3.35 | PBI 16 | 2.36 | 4.10 |
| NB 1 | 1.71 | 4.37 | DBCDI 10 | 2.37 | 4.53 |
| NB 2 | 1.71 | 4.13 | DBCDI 4 | 2.39 | 4.62 |
| quaterrylene | 1.81 | 3.14 | CDI 12 | 2.41 | NA |
| PMI 4 | 1.85 | NA | PBI 3 | 2.43 | 4.22 |
| PMI 3 | 1.90 | 3.67 | CDI 11 | 2.44 | 5.15 |
| PB 2 | 2.01 | 3.92 | NBB 1a | 2.46 | 4.53 |
| PMI 2 | 2.03 | 3.99 | PBI 15 | 2.47 | 4.65 |
| CAN 2 | 2.05 | 4.91 | PBI 1 | 2.47 | NA |
| DBCDI 7 | 2.07 | 3.77 | PBI 11 | 2.48 | 4.89 |
| PB 1 | 2.08 | 3.94 | NBB 1s | 2.49 | 4.34 |
| OCDI 1 | 2.08 | 4.68 | NBB 2s | 2.49 | 4.19 |
| CDI 15 | 2.11 | 4.41 | PBB 2a | 2.50 | 4.01 |
| CDI 10 | 2.14 | 4.52 | PBB 1a | 2.50 | 4.12 |
| CDI 14 | 2.15 | 4.55 | PBB 2s | 2.50 | 3.95 |
| CDI 1 | 2.15 | 4.58 | PBB 1s | 2.51 | 4.07 |
| CDI 18 | 2.16 | 4.58 | DBCDI 9 | 2.51 | 4.80 |
| CDI 16 | 2.16 | 4.58 | PBI 6 | 2.51 | NA |
| CDI 17 | 2.16 | 4.61 | PBI 5 | 2.52 | 4.19 |
| DBCDI 6 | 2.17 | 4.04 | NDI 1 | 2.52 | 5.57 |
| CDI 2 | 2.17 | 4.51 | PBI 8 | 2.52 | NA |
| CDI 19 | 2.17 | 4.60 | PBI | 2.53 | 4.50 |
| CDI 9 | 2.18 | 4.53 | BPI | 2.53 | NA |
| CDI 13 | 2.18 | 4.62 | PBI 17 | 2.58 | 4.60 |
| DBCDI 5 | 2.19 | 4.10 | PBI 12 | 2.60 | 4.98 |
| CDI 21 | 2.19 | 4.75 | PBI 14 | 2.64 | 4.09 |
| Benzimidazole CDI | 2.20 | 4.52 | NDI 3 | 2.65 | 5.71 |
| CDI 3 | 2.20 | 4.66 | PBI 10 | 2.67 | 4.72 |
| DBCDI 1 | 2.23 | 4.21 | ACTI 1 | 2.76 | 4.00 |
| CDI 8 | 2.23 | 4.77 | PBI 4 | 2.94 | 4.94 |
| PBI 7 | 2.24 | 3.93 | NDI 2 | 3.08 | 6.08 |
| CDI 4 | 2.25 | 4.73 | | | |

Figure 18

| PBI 1 + Li$_2$S$_8$ | Li$_2$S$_8$ |
|---|---|
| 207 | 31 |
| 225 | 71 |
| 227 | 126 |
| 230 | 139 |
| 242 | 143 |
| 245 | 148 |
| 250 | 163 |
| 251 | 189 |
| 254 | 189 |
| 254 | 192 |
| 260 | 205 |
| 265 | 205 |
| 265 | 206 |
| 266 | 211 |
| 266 | 215 |
| 267 | 227 |
| 268 | 235 |
| 272 | 240 |
| 295 | 241 |
| 295 | 258 |
| 297 | 263 |
| 315 | - |
| 316 | - |
| 322 | - |
| 326 | - |
| 383 | - |
| 26 Cells | 21 Cells |

Figure 19

| Catholyte Identity | Average (All Data) | Std. Deviation (All Data) | Standard Error of the Mean | Average (Chauvenet's) | Std. Deviation (Chauvenet's) | Standard Error of the Mean |
|---|---|---|---|---|---|---|
| PBI 1 + Li$_2$S$_8$ | 272 | 37.7 | 7.39 | 267 | 31.0 | 6.21 |
| Li$_2$S$_8$ | 186 | 58.0 | 12.7 | 193 | 47.7 | 10.7 |

Figure 29
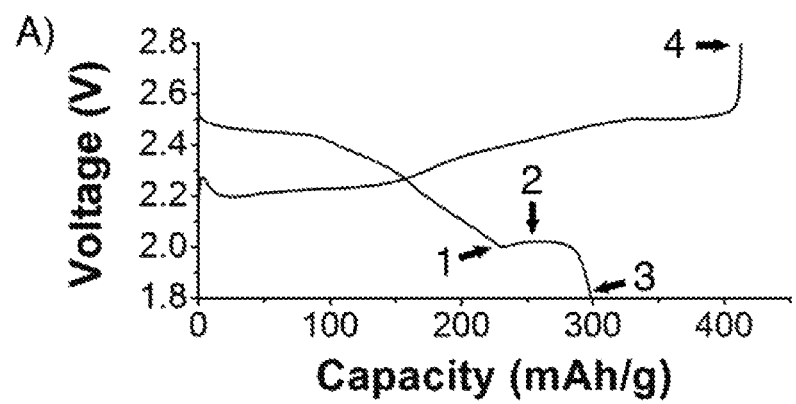
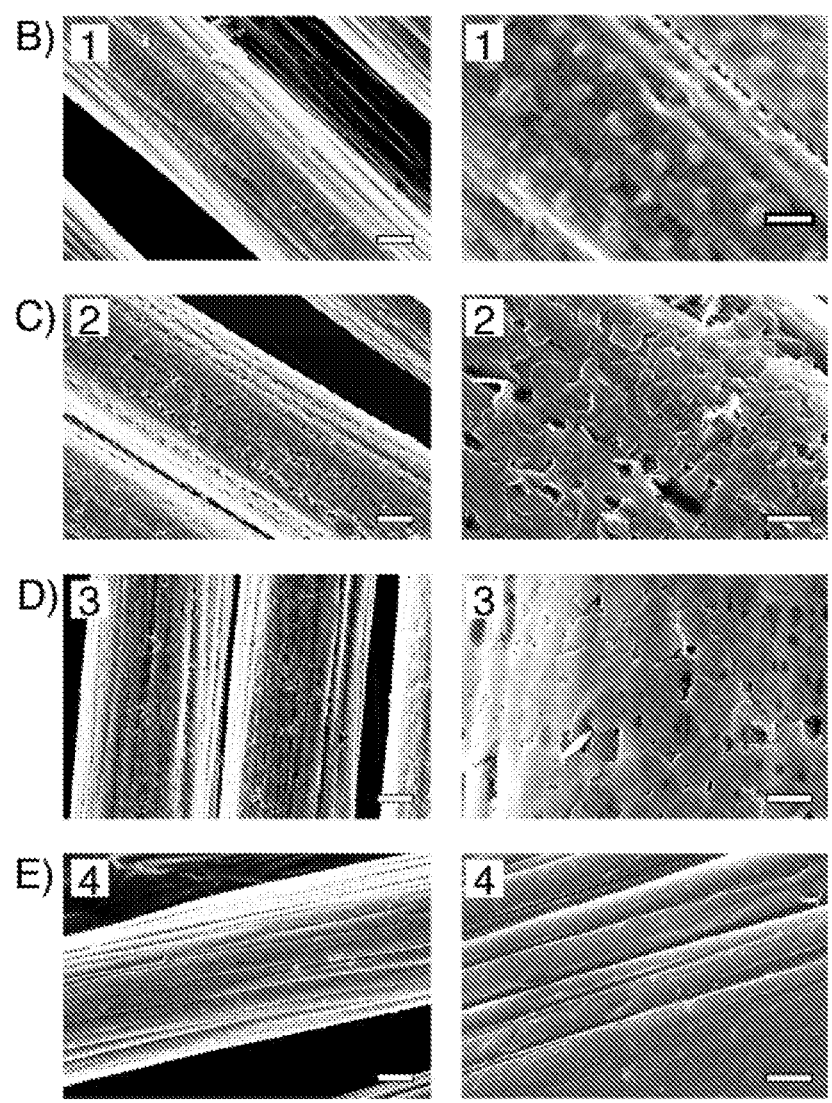

REDOX MEDIATORS FOR METAL-SULFUR BATTERIES

CROSS-REFERENCES TO RELATED APPLICATIONS

This application claims priority to U.S. Provisional Application Nos. 62/154,040, filed Apr. 28, 2015, 62/136,348, filed Mar. 20, 2015, and 62/036,056, filed Aug. 11, 2014, each of which is incorporated in its entirety herein for all purposes.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 and under the Joint Center for Energy Storage Research awarded by the U.S. Department of Energy. The government has certain rights in the invention.

BACKGROUND OF THE INVENTION

Batteries require facile charge transfer to be successful, but it is a challenge when the desired active material is an electronic insulator. This is the case in many types of well-studied battery materials: $LiFePO_4$ in Li-ion batteries, $Li_2O_2$ in Li-air batteries, and $S_8$ and $Li_2S$ in Li-sulfur batteries. The insulating nature of these materials can cause low rate tolerance, low capacities, and polarization. This has remedied by adding a conductive additive, commonly conductive carbon materials.

Additional challenges occur when the insulating product of battery discharge undergoes a phase change to deposit as a solid. When a solid forms during cycling, the deposition of this species needs to be accounted for to design a successful battery by providing surface area on which it can deposit. In Li-sulfur battery cathodes elemental sulfur ($S_8$) is reduced to $Li_2S$ through soluble (in typical battery electrolytes) polysulfide species ($Li_2S_x$, x=4-8), while $Li_2S$, the final discharge product, is an insoluble, electronically insulating species. In Li—$O_2$ batteries, gaseous $O_2$ is reduced to form solid, insulating, insoluble $Li_2O_2$. In both cases, the solid phase nucleates on the surface where it is reduced, usually by the conductive carbon additive, and once an insulating layer is formed, the reaction can no longer proceed terminating discharge (although conductivity may be imparted to $Li_2O_2$ through Li vacancies). This means that the surface area of the conductive carbon additive contributes to the amount of active material that can be utilized. In order to increase battery capacity, many types of carbon materials with high surface areas are utilized, including commercial microparticles (such as Ketjenblack or Super P), carbon fibers and nanotubes, and hierarchically porous carbons.

A redox mediator is a compound with a reversible redox couple that facilitates electron transfer from the electrode to the active species. Rather than direct electron transfer from the electrode to the active species, electron transfer takes place over two steps; the redox mediator is reduced/oxidized at the electrode, diffuses away, reduces/oxidizes the active species, and in this process is returned to its original state so the process can repeat. Soluble redox mediators have been used in batteries to facilitate the charge, discharge, or both of the $Li_2O_2/O_2$ cathode in Li—$O_2$ batteries as well as to facilitate charge transfer to insulating $LiFePO_4$ in Li-ion batteries. Redox mediators are only beginning to be explored in their application to Li—S batteries, e.g., Aurbach et al. have reported on the use of redox mediators to lower the overpotential required for activating solid-state $Li_2S$ cathodes (WO 2015044829). What is needed are new redox mediators and energy storage devices incorporating the new redox mediators. Surprisingly, the present invention meets this and other needs.

BRIEF SUMMARY OF THE INVENTION

In one embodiment, the present invention provides an energy storage device having an anode, a cathode having a metal sulfide $M_xS_y$, wherein M is a metal, subscript x is from 0 to 2 and y is from 1 to 8, a redox mediator having a redox potential suitable for reducing or oxidizing $M_xS_y$, and an electrolyte. The energy storage device also includes a membrane separator between the anode and the cathode, and a current collector in electrical contact with the anode and cathode.

In another embodiment, the present invention provides a compound of Formula I:

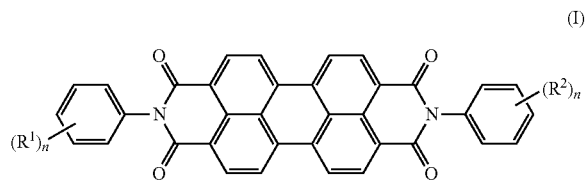

(I)

wherein each $R^1$ and $R^2$ is independently selected from the group consisting of halogen, $C_{1-20}$ alkyl, $C_{1-20}$ haloalkyl, $C_{1-20}$ alkoxy, $C_{1-20}$ heteroalkyl, $C_{3-20}$ carbocycle, $C_{3-20}$ heterocycle, $C_{6-20}$ aryl, $C_{5-20}$ heteroaryl, —N($R^3$)($R^4$), —O$R^3$, —C(O)$R^3$, —C(O)O$R^3$, —OC(O)$R^3$, —C(O)N($R^3$)($R^4$), —N($R^3$)C(O)$R^4$, —N($R^3$)C(O)N($R^4$)($R^5$), —OC(O)N($R^4$)($R^5$), —N($R^3$)C(O)O$R^4$, —S$R^3$, —S(O)$R^3$, —S(O)$_2R^3$, —$N_3$, —B(O$R^3$)$_2$, and —Se$R^3$; alternatively, two $R^1$ or $R^2$ groups on adjacent ring atoms can be combined to form —O(CH$_2$CH$_2$)$_m$O—, wherein subscript m is an integer from 3 to 10; each $R^3$, $R^4$ and $R^5$ is independently selected from the group consisting of H and $C_{1-20}$ alkyl; and each subscript n is from 1 to 5.

In another embodiment, the present invention provides a compound of Formula II:

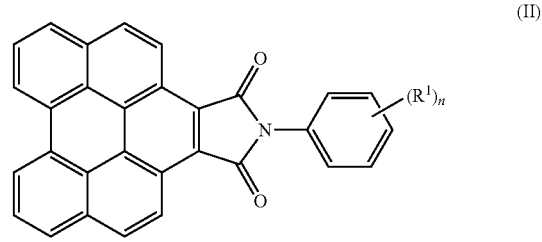

(II)

wherein each $R^1$ is independently selected from the group consisting of halogen, $C_{1-20}$ alkyl, $C_{1-20}$ haloalkyl, $C_{1-20}$ alkoxy, $C_{1-20}$ heteroalkyl, $C_{3-20}$ carbocycle, $C_{3-20}$ heterocycle, $C_{6-20}$ aryl, $C_{5-20}$ heteroaryl, —N($R^3$)($R^4$), —O$R^3$, —C(O)$R^3$, —C(O)O$R^3$, —OC(O)$R^3$, —C(O)N($R^3$)($R^4$), —N($R^3$)C(O)$R^4$, —N($R^3$)C(O)N($R^4$)($R^5$), —OC(O)N($R^4$)($R^5$), —N($R^3$)C(O)O$R^4$, —S$R^3$, —S(O)$R^3$, —S(O)$_2R^3$, —$N_3$, —B(O$R^3$)$_2$, and —Se$R^3$; alternatively, two $R^1$ groups on adjacent ring atoms can be combined to form —O(CH$_2$CH$_2$)$_m$O—, wherein subscript m is an integer from 3 to 10; each R$^3$, R$^4$ and R$^5$ is independently selected from the group consisting of H and C$_{1-20}$ alkyl; and subscript n is from 1 to 5.

In another embodiment, the present invention includes an electrode composition having a metal sulfide M$_x$S$_y$, wherein M is a metal, subscript x is from 0 to 2 and y is from 1 to 8, a redox mediator having a redox potential suitable for reducing or oxidizing M$_x$S$_y$, and an electrolyte.

BRIEF DESCRIPTION OF THE DRAWINGS

FIG. 17 shows a list of E$_{ea}$ and E$_i$ values (vs. Li/Li$^+$) computed for molecules with labels corresponding to the structures in FIG. 15 and FIG. 16. The list is ordered from lowest to highest E$_{ea}$. The color-coding is by class of molecule: polycyclic aromatic hydrocarbons (yellow), miscellaneous (green), coronene diimides (blue), and perylene bisimides (orange).

FIG. 18 shows second cycle discharge capacities (mAh g$^{-1}$(S)) of batteries with PBI 1+Li$_2$S$_8$ or Li$_2$S$_8$ alone as catholyte cycled at C/8 rate from 2.8 to 2.0 V. The values highlighted in yellow were rejected from the overall data analysis using Chauvenet's criterion.

FIG. 19 shows statistical analysis of second cycle discharge capacities (mAh g$^{-1}$ (S)) of batteries with PBI 1+Li$_2$S$_8$ or Li$_2$S$_8$ alone as catholyte cycled at C/8 rate from 2.8 to 2.0 V. The average and standard error after rejection of outliers by Chauvenet's criterion are reported in the text.

FIGS. 29A, B, C, D and E shows deposition of Li$_2$S on carbon felt imaged at different states-of-charge (first discharge and charge, C/8) A) Representative discharge/charge curve of a Li—S battery without BPI and the states-of-charge at which batteries were stopped to remove the carbon felt and image the Li$_2$S that had been deposited. Voltage is versus Li/Li$^+$. B) SEM images of Li$_2$S on C felt at the nucleation point, 1. C) SEM images of Li$_2$S on C felt in the Li$_2$S deposition plateau, 2. D) SEM images of Li$_2$S on C felt after discharge, 3. E) SEM images of C felt after recharge, 4. Scale bar (left images)=2 μm. Scale bar (right images)= 500 nm.

34 shows a schematic representation of HBC assembly into supramolecular networks in liquid electrolyte.

Figure 35:
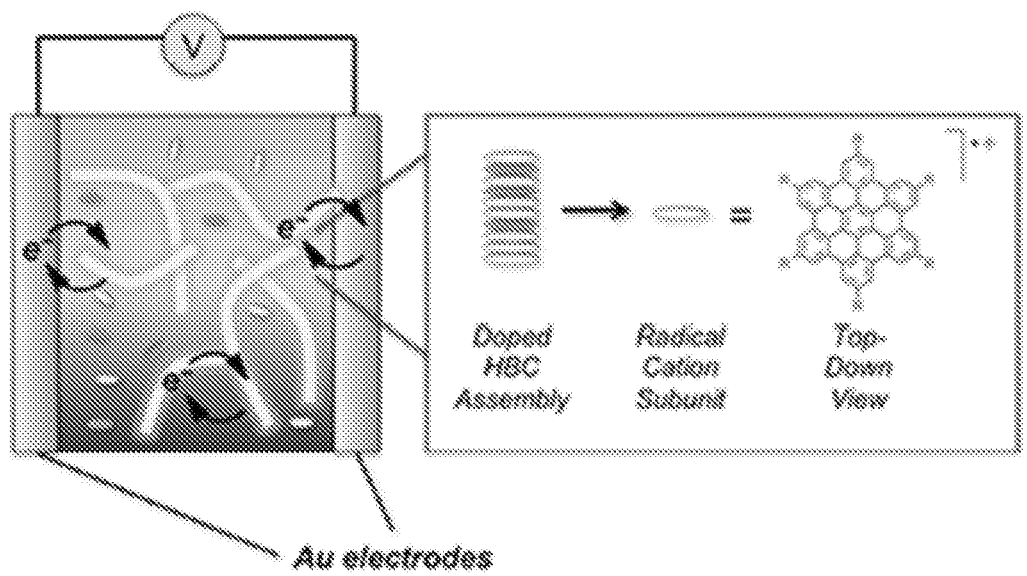

FIG. 35 shows schematic representation of HBC assembly into supramolecular networks in liquid electrolyte and subsequent chemical doping by HBC radical cations, which enhance the electronic charge transporting ability of the network.

Figure 36:
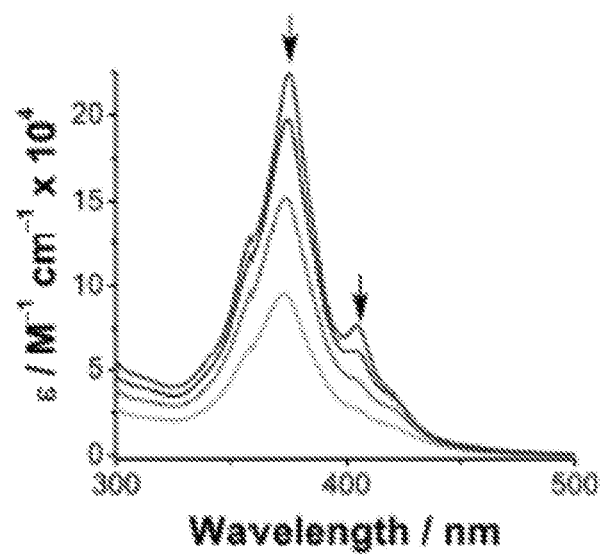

FIG. 36 shows variation in the optical extinction coefficient ($\varepsilon$ with concentration (c). Arrows indicate change with increasing c.

Figure 37:
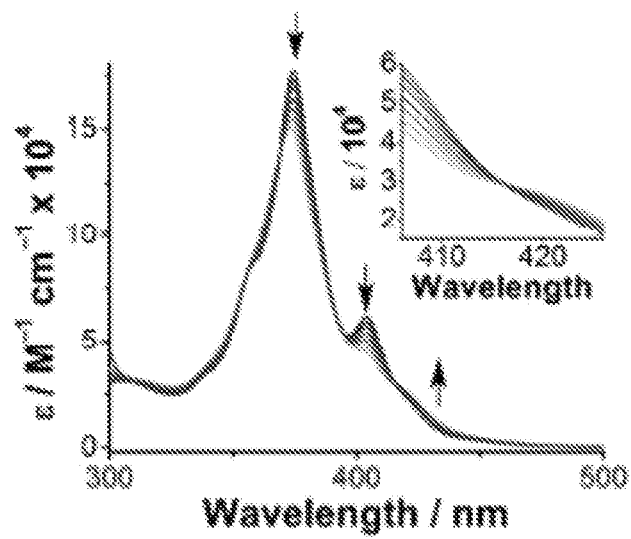

FIG. 37 shows variation in with temperature (T). Arrows indicate change with decreasing T (90° C. to 30° C.). Inset: Isosbestic point at $\lambda$=416 nm.

Figure 38:
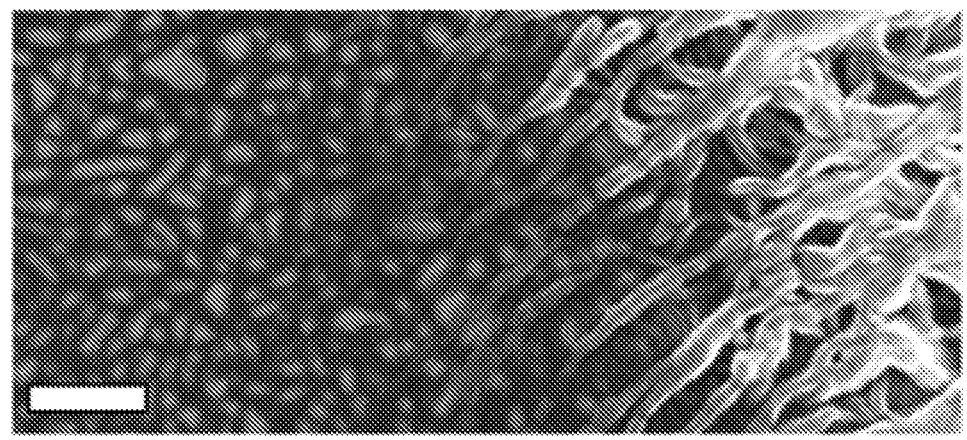

FIG. 38 shows SEM of supramolecular networks of HBC 7. Scale bar=2 µm.

Figure 39:
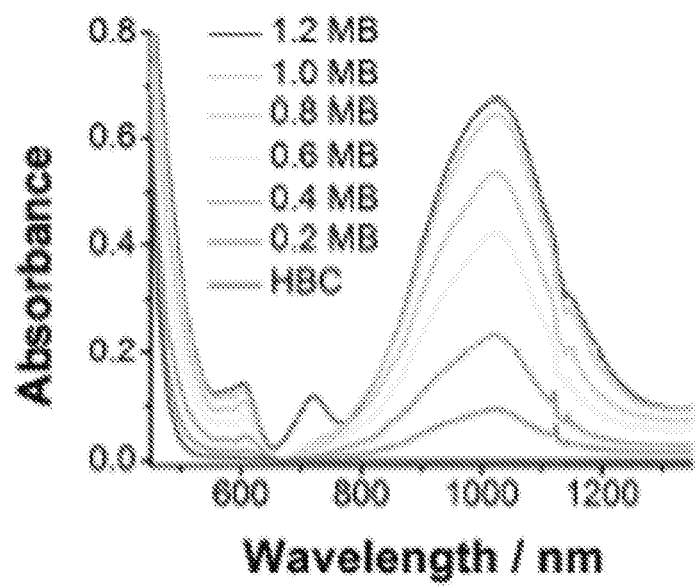

FIG. 39 shows UV-vis spectroscopy obtained during the chemical oxidation of 7 with controlled amounts of MB in electrolyte.

Figure 40:
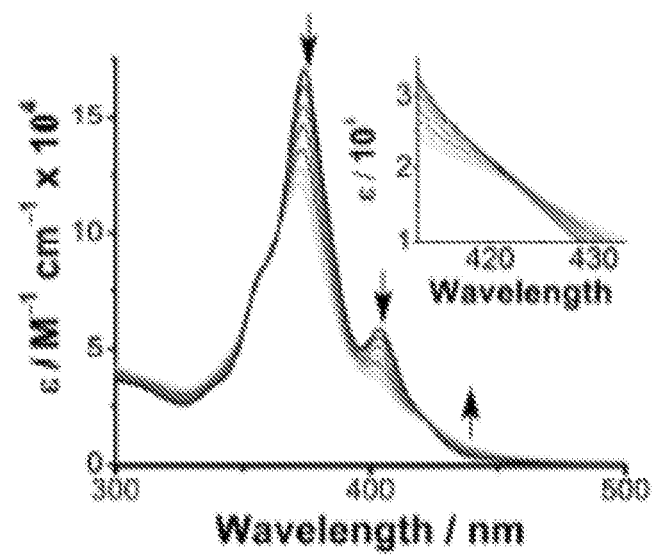

FIG. 40 shows variable temperature UV-Vis of a 3:1 mixture of 7:8 between 30 and 90° C. Arrows indicate change with decreasing temperature. Inset: Isosbestic point at $\lambda$=423 nm.

Figure 41:
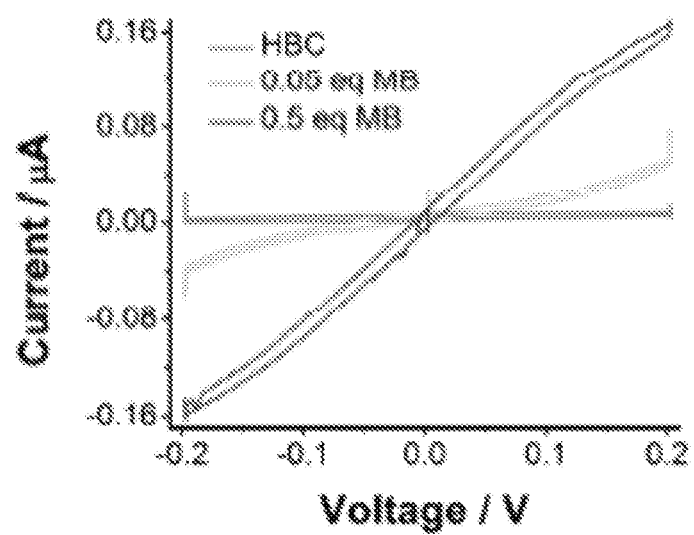

FIG. 41 shows I-V curves of different ratios of 7:8.

Figure 42:
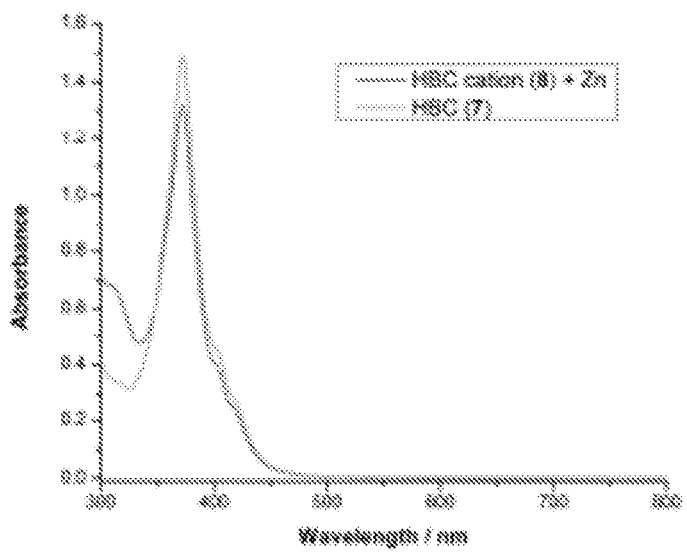

FIG. 42 shows reversible reduction of HBC radical cation 8 at 10 µM.

Figure 43:
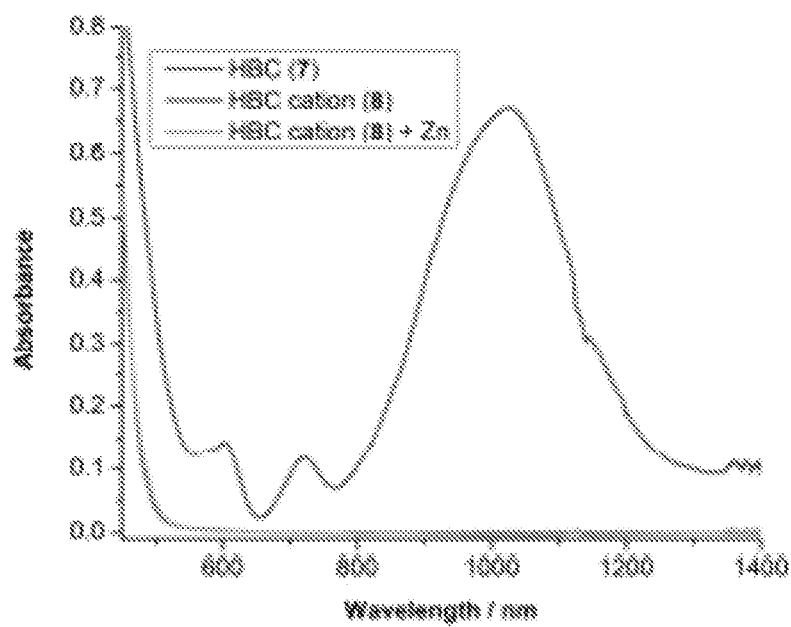

FIG. 43 shows Reversible reduction of HBC radical cation 8 at 150 µM.

Figure 44:
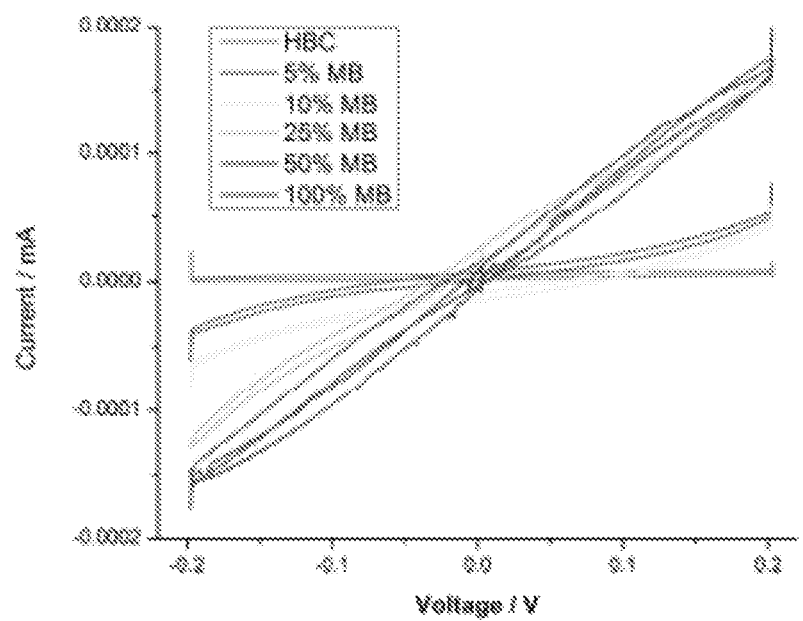

FIG. 44 shows IV curves of HBC with increasing amounts of Magic Blue.

DETAILED DESCRIPTION OF THE INVENTION

I. General

The present invention generally relates to energy storage devices, and to sulfur or metal sulfide energy storage devices in particular. Some aspects of the invention relate to energy storage devices comprising at least one flowable electrode, wherein the flowable electrode comprises a sulfur or metal sulfide electroactive material suspended and/or dissolved in a fluid. In some embodiments, the flowable electrode further comprises a plurality of electronically conductive particles suspended in the fluid, wherein the electronically conductive particles form a percolating conductive network. An energy storage device comprising a flowable electrode comprising a sulfur or metal sulfide electroactive material and a percolating conductive network may advantageously exhibit, upon reversible cycling, higher energy densities and specific capacities than conventional energy storage devices.

In many conventional energy storage devices with flow-based systems (e.g., flow batteries, half-flow batteries, redox flow devices, etc.), an electrode comprising an electroactive material is flowed through or adjacent a stationary current collector. In these conventional energy storage devices, the charge transfer required for redox reactions takes place only when redox species contact the current collector surface through diffusion or fluid convection. By contrast, some embodiments of the present invention include an electrode comprising a percolating conductive network, and charge transfer may occur throughout the volume of the electrode. As a result, the available charge transfer area may significantly increase or be utilized more efficiently and may lead to a reduction in charge transfer resistance. Additionally, in some embodiments, an energy storage device comprising a sulfur or metal sulfide electroactive material and a percolating conductive network may be reversibly cycled into regimes where a metal sulfide is precipitated from and subsequently dissolved and/or suspended in the fluid. The ability to participate in precipitation regimes may result in higher energy densities and specific capacities than conventional redox solution-based energy storage devices, which generally cannot be reversibly cycled through such precipitation regimes. The present invention provides a new electrode composition for metal-sulfide batteries, including a polycyclic aromatic hydrocarbon redox mediator. Examples of polycyclic aromatic hydrocarbons pertaining to the present invention include, but are not limited to, naphthalenes, perylenes, benzoperylenes, and coronenes. In some embodiments the redox mediator may self-assemble into $\pi$-stacked supramolecular fibers where charge transport is improved by self-exchange of charge between redox mediators in a fiber. Fibers composed of self-assembled redox mediators may be brought in close proximity by electrostatic interactions between anionic polysulfide and cationic metal that is coordinated to the redox mediator. This inter-fiber contact may improve charge transfer between fibers and alter the rheological properties of the mixture.

II. Definitions

"Metal" refers to elements of the periodic table that are metallic and that can be neutral, or negatively or positively charged as a result of having more or fewer electrons in the valence shell than is present for the neutral metallic element. Metals useful in the present invention include the alkali metals, alkaline earth metals, transition metals and post-transition metals. Alkali metals include Li, Na, K, Rb and Cs. Alkaline earth metals include Be, Mg, Ca, Sr and Ba. Transition metals include Ti, V, Cr, Mn, Fe, Co, Ni, Cu, Zn, Zr, Nb, Mo, Tc, Ru, Rh, Pd, Ag, Cd, Hf, Ta, W, Re, Os, Ir, Pt, Au, Hg. Post-transition metals include Al, Ga, In, Tl, Ge, Sn, Pb, Sb, Bi, and Po. Rare earth metals include Sc, Y, La, Ac, Ce, Pr, Nd, Sm, Eu, Gd, Tb, Dy, Ho, Er, Tm, Yb and Lu. One of skill in the art will appreciate that the metals described above can each adopt several different oxidation states, all of which are useful in the present invention. In some instances, the most stable oxidation state is formed, but other oxidation states are useful in the present invention.

"Redox mediator" refers to any material facilitating the reduction of a metal sulfide, metal polysulfide or sulfur. Representative redox mediators include polycyclic aromatic hydrocarbons (PAHs) and compounds of the present invention. Polycyclic aromatic hydrocarbons are compounds containing multiple aromatic rings, and can include polynuclear aromatic hydrocarbons (PNAs) where at least some of the aromatic rings are fused to one another. Representative polycyclic aromatic hydrocarbons can include naphthalene, anthracene, pyrene, phenanthrene, tetracene, chrysene, triphenylene, pentacene, benzopyrenes such as benzo[a]pyrine and benzo[e]pyrene, corannulene, benzoperylene such as benzo[ghi]perylene, fluoranthene, benzofluoranthene such as benzo[b]fluoranthene, benzo[i]fluoranthene and benzo[k]fluoranthene, coronene, ovalene, and perylene.

"Electrolyte" refers to an ionically conductive substance or composition and can include solvents, ionic liquids, metal salts, ions such as metal ions or inorganic ions, polymers and other components.

"Membrane separator" refers to a membrane between the anode and the cathode that is ionically conductive but not electrically conductive.

"Metal salt" refers to a metal cation having a corresponding anion.

"Conductive additive" refers to a component of the cathode that improves the electrical conductivity of the cathode.

"Halogen" refers to fluorine, chlorine, bromine and iodine.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc. Longer haloalkyl groups are also contemplated, such as $C_{1-20}$ haloalkyl. In some instances, the term "perfluoro" can be used to define a compound or radical where all the hydrogens are replaced with fluorine. For example, perfluoromethyl refers to 1,1,1-trifluoromethyl.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Longer alkoxy groups are also contemplated, such as $C_{1-20}$ alkoxy. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Heteroalkyl" refers to an alkyl group of any suitable length and having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines. The heteroatom portion of the heteroalkyl can replace a hydrogen of the alkyl group to form a hydroxy, thio or amino group. Alternatively, the heteroatom portion can be the connecting atom, or be inserted between two carbon atoms.

"Cycloalkyl" or "carbocycle" refers to a saturated or partially unsaturated, monocyclic, fused bicyclic or bridged polycyclic ring assembly containing from 3 to 20 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Heterocycloalkyl" or "heterocycle" refers to a saturated ring system having from 3 to 20 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (═O), among many others.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15, 16, 17, 18, 19 or 20 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic or fused bicyclic or tricyclic aromatic ring assembly containing 5 to 20 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

wherein each $R^1$ and $R^2$ is independently selected from the group consisting of halogen, $C_{1-20}$ alkyl, $C_{1-20}$ haloalkyl, $C_{1-20}$ alkoxy, $C_{1-20}$ heteroalkyl, $C_{3-20}$ carbocycle, $C_{3-20}$ heterocycle, $C_{6-20}$ aryl, $C_{5-20}$ heteroaryl, —N($R^3$)($R^4$), —O$R^3$, —C(O)$R^3$, —C(O)O$R^3$, —OC(O)$R^3$, —C(O)N($R^3$)($R^4$), —N($R^3$)C(O)$R^4$, —N($R^3$)C(O)N($R^4$)($R^5$), —OC(O)N($R^4$)($R^5$), —N($R^3$)C(O)O$R^4$, —S$R^3$, —S(O)$R^3$, —S(O)$_2R^3$, —N$_3$, —B(O$R^3$)$_2$, and —Se$R^3$; alternatively, two $R^1$ or $R^2$ groups on adjacent ring atoms can be combined to form —O(CH$_2$CH$_2$)$_m$O—, wherein subscript m is an integer from 3 to 10; each $R^3$, $R^4$ and $R^5$ is independently selected from the group consisting of H and $C_{1-20}$ alkyl; and each subscript n is from 1 to 5.

In some embodiments, the present invention can be the compound of Formula I, wherein each $R^1$ and $R^2$ can be $C_{1-20}$ alkoxy. In some embodiments, each $R^1$ and $R^2$ can be —O(CH$_2$)$_3$CH$_3$, —O(CH$_2$)$_5$CH$_3$, —O(CH$_2$)$_7$CH$_3$, or —O(CH$_2$)$_{11}$CH$_3$. In some embodiments, each $R^1$ and $R^2$ can be $C_{1-20}$ heteroalkyl. In some embodiments, each $R^1$ and $R^2$ can be —O—(CH$_2$CH$_2$O)$_2$CH$_3$. In some embodiments, each $R^1$ and $R^2$ can be —OCH$_3$, —O—(CH$_2$CH$_2$O)CH$_3$, —O—(CH$_2$CH$_2$O)$_2$CH$_3$, —O—(CH$_2$CH$_2$O)$_3$CH$_3$, —O—(CH$_2$CH$_2$O)$_4$CH$_3$, or —O—(CH$_2$CH$_2$O)$_5$CH$_3$. In some embodiments, each $R^1$ and $R^2$ can be —O—(CH$_2$CH$_2$O)$_2$CH$_3$. In some embodiments, the compound of Formula I can have the following structure:

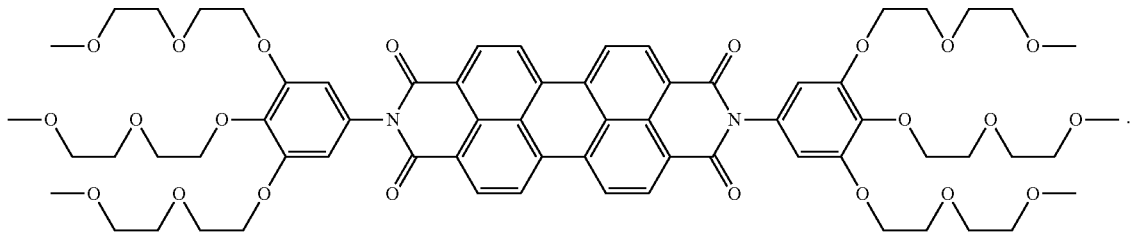

In some embodiments, the present invention provides a compound of Formula Ia:

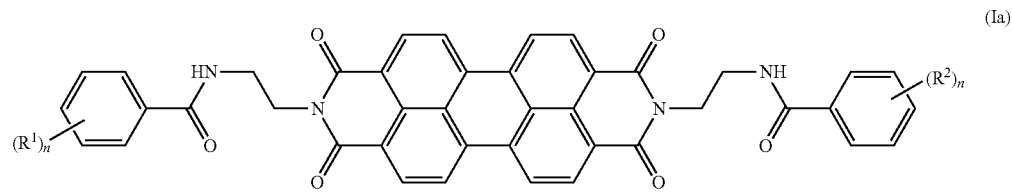

(Ia)

III. Redox Compounds

The present invention provides redox compounds of Formula I and Formula II. In some embodiments, the present invention provides a compound of Formula I:

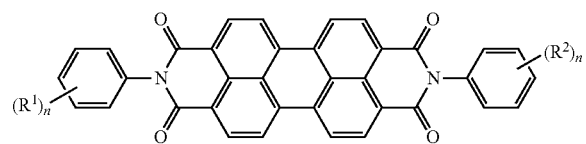

(I)

wherein each $R^1$ and $R^2$ is independently selected from the group consisting of halogen, $C_{1-20}$ alkyl, $C_{1-20}$ haloalkyl, $C_{1-20}$ alkoxy, $C_{1-20}$ heteroalkyl, $C_{3-20}$ carbocycle, $C_{3-20}$ heterocycle, $C_{6-20}$ aryl, $C_{5-20}$ heteroaryl, —N($R^3$)($R^4$), —O$R^3$, —C(O)$R^3$, —C(O)O$R^3$, —OC(O)$R^3$, —C(O)N($R^3$)($R^4$), —N($R^3$)C(O)$R^4$, —N($R^3$)C(O)N($R^4$)($R^5$), —OC(O)N($R^4$)($R^5$), —N($R^3$)C(O)O$R^4$, —S$R^3$, —S(O)$R^3$, —S(O)$_2R^3$, —N$_3$, —B(O$R^3$)$_2$, and —Se$R^3$; alternatively, two $R^1$ or $R^2$ groups on adjacent ring atoms can be combined to form —O(CH$_2$CH$_2$)$_m$O—, wherein subscript m is an integer from 3 to 10; each $R^3$, $R^4$ and $R^5$ is independently selected from the group consisting of H and $C_{1-20}$ alkyl; and each subscript n is from 1 to 5.

In some embodiments, the present invention provides a compound of Formula II:

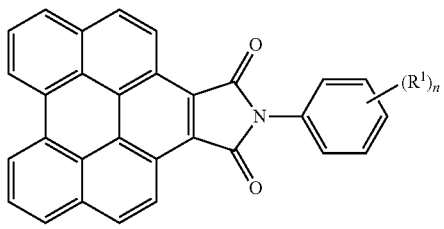

(II)

wherein each $R^1$ is independently selected from the group consisting of halogen, $C_{1-20}$ alkyl, $C_{1-20}$ haloalkyl, $C_{1-20}$ alkoxy, $C_{1-20}$ heteroalkyl, $C_{3-20}$ carbocycle, $C_{3-20}$ heterocycle, $C_{6-20}$ aryl, $C_{5-20}$ heteroaryl, $-N(R^3)(R^4)$, $-OR^3$, $-C(O)R^3$, $-C(O)OR^3$, $-OC(O)R^3$, $-C(O)N(R^3)(R^4)$, $-N(R^3)C(O)R^4$, $-N(R^3)C(O)N(R^4)(R^5)$, $-OC(O)N(R^4)(R^5)$, $-N(R^3)C(O)OR^4$, $-SR^3$, $-S(O)R^3$, $-S(O)_2R^3$, $-N_3$, $-B(OR^3)_2$, and $-SeR^3$; alternatively, two $R^1$ groups on adjacent ring atoms can be combined to form $-O(CH_2CH_2)_mO-$, wherein subscript m is an integer from 3 to 10; each $R^3$, $R^4$ and $R^5$ is independently selected from the group consisting of H and $C_{1-20}$ alkyl; and subscript n is from 1 to 5.

In some embodiments, the present invention provides a compound of Formula II wherein each $R^1$ is $-O-(CH_2CH_2O)_3CH_3$; and subscript n is 2. In some embodiments, the compound of Formula II can have the structure:

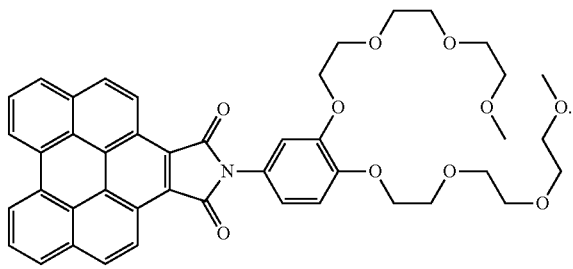 [SMILES: COCCOCCOCCOc1ccc(-n2c(=O)c3c4ccc5cccc6c7cccc8ccc(c3c2=O)c(c87)c4c56)cc1OCCOCCOCCOC]

In some embodiments, the present invention provides a compound of Formula III:

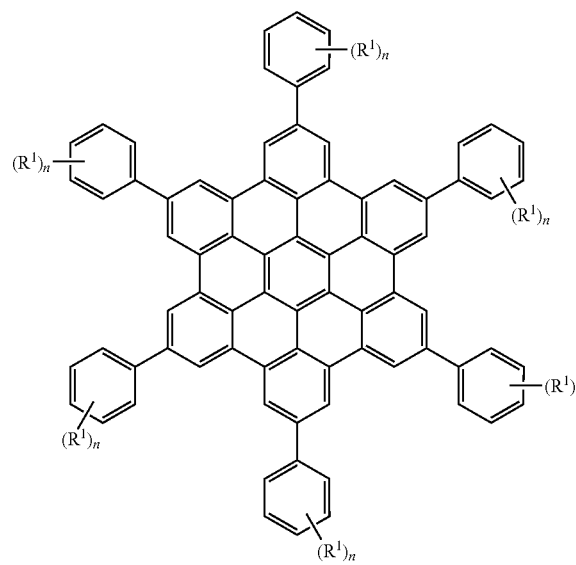

(III)

wherein each $R^1$ is independently selected from the group consisting of halogen, $C_{1-20}$ alkyl, $C_{1-20}$ haloalkyl, $C_{1-20}$ alkoxy, $C_{1-20}$ heteroalkyl, $C_{3-20}$ carbocycle, $C_{3-20}$ heterocycle, $C_{6-20}$ aryl, $C_{5-20}$ heteroaryl, $-N(R^3)(R^4)$, $-OR^3$, $-C(O)R^3$, $-C(O)OR^3$, $-OC(O)R^3$, $-C(O)N(R^3)(R^4)$, $C_{1-20}$ alkyl-$C(O)N(R^3)(R^4)$, $-N(R^3)C(O)R^4$, $-N(R^3)C(O)N(R^4)(R^5)$, $-OC(O)N(R^4)(R^5)$, $-N(R^3)C(O)OR^4$, $-SR^3$, $-S(O)R^3$, $-S(O)_2R^3$, $-N_3$, $-B(OR^3)_2$, and $-SeR^3$; alternatively, two $R^1$ groups on adjacent ring atoms can be combined to form $-O(CH_2CH_2)_mO-$, wherein subscript m is an integer from 3 to 10; each $R^3$, $R^4$ and $R^5$ is independently selected from the group consisting of H and $C_{1-20}$ alkyl; and subscript n is from 1 to 5.

In some embodiments, each $R^1$ can independently be halogen, $C_{1-20}$ alkoxy, $-OR^3$, or $C_{1-20}$ alkyl-$C(O)N(R^3)(R^4)$. In some embodiments, subscript n can be 3. In some embodiments, each $R^1$ can be fluoro, $-(CH_2)_5C(O)NMe_2$, $-O(CH_2)_3CH_3$, $-O(CH_2)_5CH_3$, $-O(CH_2)_7CH_3$, $-O(CH_2)_9CH_3$, or $-O(CH_2)_{11}CH_3$.

In some embodiments, the present invention provides a compound of Formula III having the structure:

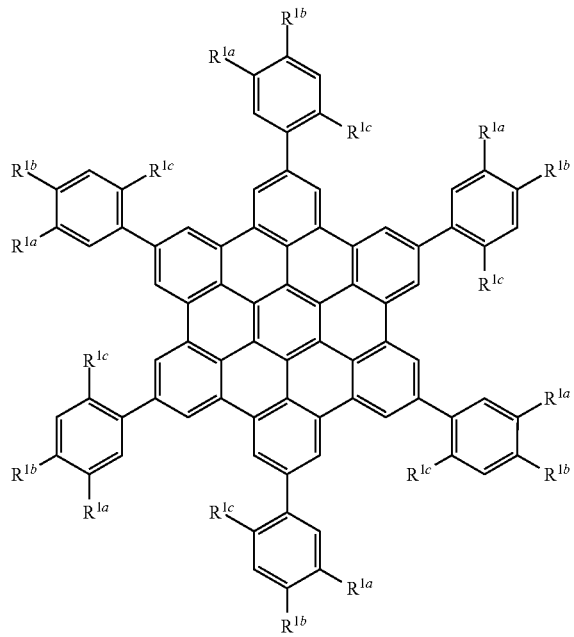

wherein each of $R^{1a}$, $R^{1b}$ and $R^{1c}$ can independently be halogen, $C_{1-20}$ alkyl, $C_{1-20}$ haloalkyl, $C_{1-20}$ alkoxy, $C_{1-20}$ heteroalkyl, $C_{3-20}$ carbocycle, $C_{3-20}$ heterocycle, $C_{6-20}$ aryl, $C_{5-20}$ heteroaryl, $-N(R^3)(R^4)$, $-OR^3$, $-C(O)R^3$, $-C(O)OR^3$, $-OC(O)R^3$, $-C(O)N(R^3)(R^4)$, $C_{1-20}$ alkyl-$C(O)N(R^3)(R^4)$, $-N(R^3)C(O)R^4$, $-N(R^3)C(O)N(R^4)(R^5)$, $-OC(O)N(R^4)(R^5)$, $-N(R^3)C(O)OR^4$, $-SR^3$, $-S(O)R^3$, $-S(O)_2R^3$, $-N_3$, $-B(OR^3)_2$, and $-SeR^3$; alternatively, two $R^1$ groups on adjacent ring atoms can be combined to form $-O(CH_2CH_2)_mO-$, wherein subscript m is an integer from 3 to 10; each $R^3$, $R^4$ and $R^5$ is independently selected from the group consisting of H and $C_{1-20}$ alkyl. In some embodiments, each of $R^{1a}$, $R^{1b}$ and $R^{1c}$ can independently be halogen, $C_{1-20}$ alkoxy, $-OR^3$, or $C_{1-20}$ alkyl-$C(O)N(R^3)(R^4)$. In some embodiments, $R^{1a}$ and $R^{1c}$ are each fluoro, and $R^{1b}$ can be $-(CH_2)_5C(O)NMe_2$.

In some embodiments, the present invention provides a compound of Formula III having the structure:

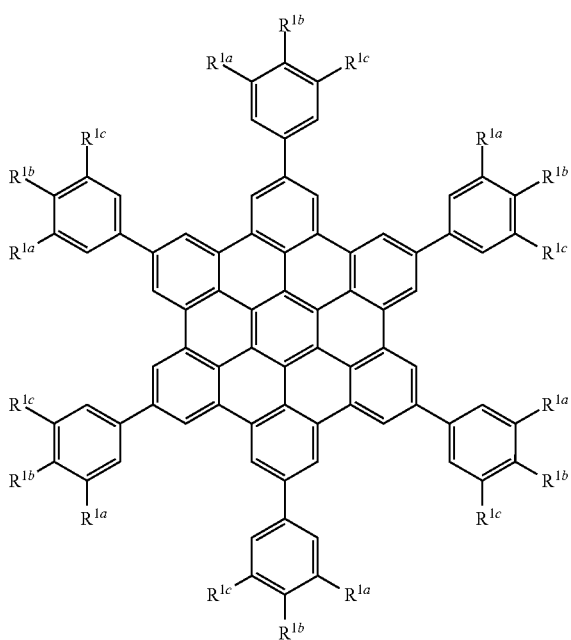

wherein each of $R^{1a}$, $R^{1b}$ and $R^{1c}$ can independently be halogen, $C_{1-20}$ alkyl, $C_{1-20}$ haloalkyl, $C_{1-20}$ alkoxy, $C_{1-20}$ heteroalkyl, $C_{3-20}$ carbocycle, $C_{3-20}$ heterocycle, $C_{6-20}$ aryl, $C_{5-20}$ heteroaryl, —N($R^3$)($R^4$), —O$R^3$, —C(O)$R^3$, —C(O)O$R^3$, —OC(O)$R^3$, —C(O)N($R^3$)($R^4$), $C_{1-20}$ alkyl-C(O)N($R^3$)($R^4$), —N($R^3$)C(O)$R^4$, —N($R^3$)C(O)N($R^4$)($R^5$), —OC(O)N($R^4$)($R^5$), —N($R^3$)C(O)O$R^4$, —S$R^3$, —(O)$R^3$, —S(O)$_2$ $R^3$, —N$_3$, —B(O$R^3$)$_2$, and —Se$R^3$; alternatively, two $R^1$ groups on adjacent ring atoms can be combined to form —O(CH$_2$CH$_2$)$_m$O—, wherein subscript m is an integer from 3 to 10; each $R^3$, $R^4$ and $R^5$ is independently selected from the group consisting of H and $C_{1-20}$ alkyl. In some embodiments, each of $R^{1a}$, $R^{1b}$ and $R^{1c}$ can independently be halogen, $C_{1-20}$ alkoxy, —O$R^3$, or $C_{1-20}$ alkyl-C(O)N($R^3$)($R^4$). In some embodiments, each of $R^{1a}$, $R^{1b}$ and $R^{1c}$ can independently be $C_{1-20}$ alkoxy. In some embodiments, $R^{1a}$, $R^{1b}$ and $R^{1c}$ can be —O(CH$_2$)$_3$CH$_3$, —O(CH$_2$)$_5$CH$_3$, —O(CH2)$_7$CH$_3$, —O(CH$_2$)$_9$CH$_3$, or —O(CH$_2$)$_{11}$CH$_3$.

IV. Energy Storage Device

The present invention provides an energy storage device having a redox mediator in the cathode. In some embodiments, the present invention provides an energy storage device having an anode, a cathode having a metal sulfide $M_xS_y$, wherein M is a metal, subscript x is from 0 to 2 and y is from 1 to 8, a redox mediator having a redox potential suitable for reducing or oxidizing $M_xS_y$, and an electrolyte. The energy storage device also includes a membrane separator between the anode and the cathode, and a current collector in electrical contact with the anode and cathode.

The energy storage device can be used for any suitable purpose, such as a battery.

The anode can be any suitable material. For example, the anode can include lithium. In some embodiments, the anode can be lithium.

The cathode of the energy storage device can include any suitable combination of material such as a metal sulfide, a redox mediator, and an electrolyte. Other cathode materials can include a conductive additive.

The metal sulfide of the cathode can be $M_xS_y$, wherein M is a metal, subscript x is from 0 to 2 and y is from 1 to 8. The metal M of the metal sulfide can be any suitable metal such as an alkali metal, an alkali earth metal, a transition metal, a post-transition metal or a rare-earth metal, or any combination thereof. The metal M can adopt any suitable oxidation state. In some embodiments, the metal M can be an alkali metal, an alkali earth metal or a transition metal. In some embodiments, the metal M can be an alkali metal. In some embodiments, the metal M can be lithium. The lithium metal can be in any suitable oxidation state, such as the ground oxidation state (Li$^0$). The metal M can be present in any suitable amount. In some embodiments, the metal M is absent, and subscript x is 0. In some embodiments, one metal M is present and subscript x is 1. In some embodiments, two metals M are present and subscript x is 2. When two metals M are present, the metals M can be the same or different.

When the metal M of the metal sulfide is lithium, the metal sulfide can be Li$_2$S$_8$, Li$_2$S$_6$, Li$_2$S$_4$, Li$_2$S$_2$, or Li$_2$S. In some embodiments, subscript x is 0, and the metal sulfide is elemental sulfur, S$_8$. In some embodiments, the metal sulfide can be at least one of Li$_2$S$_8$ and Li$_2$S$_6$.

Without being bound by any particular theory, discharge of an energy storage device can proceed by the elemental sulfur S$_8$ of the first electrode composition first being lithiated/reduced to form Li$_2$S$_8$, which is typically soluble in the fluid. The lithium polysulfide L$_2$S$_8$ can then be further lithiated/reduced to form Li$_2$S$_6$, Li$_2$S$_4$ and Li$_2$S$_2$, and/or Li$_2$S, etc. During charge of an energy storage device, the reactions may be reversed to form Li$_2$S, Li$_2$S$_2$, Li$_2$S$_3$, Li$_2$S$_4$, Li$_2$S$_6$, Li$_2$S$_8$, and S$_8$, etc. Generally, the discharge curve for the Li-polysulfide system exhibits at least a high voltage plateau, through which solid sulfur exists with soluble lithium polysulfides, a solution regime, in which sulfur is fully dissolved as higher-order polysulfides (e.g., Li$_2$S$_4$, Li$_2$S$_6$, Li$_2$S$_8$, etc.), and a low voltage plateau (precipitation regime), in which the discharge reaction proceeds via precipitation of lower-order polysulfides (e.g., Li$_2$S$_2$, Li$_2$S, etc.). In this embodiment, the first electrode composition may further comprise a percolating network of electronically conductive particles.

Some embodiments of the invention, like the particular embodiment described above, may provide advantages over conventional prior art devices in both the solution and precipitation regimes. Without being bound by a particular theory, cycling of an energy storage device in the solution regime may be rate-limited by charge-transfer kinetics, and embodiments comprising a percolating conductive network and/or redox mediator may experience lower charge transfer resistance than conventional energy storage devices comprising electronically-insulating redox flow compositions and stationary current collectors. In the precipitation regime, the percolating conductive network may provide greater surface area over which to deposit insoluble polysulfides, allowing an equivalent volume of polysulfide precipitate to be more thinly deposited or deposited in quasi 3-D deposits. These advantages may allow embodiments of the invention comprising a sulfur or metal sulfide electroactive material and a lithium metal anode to achieve higher specific capacities and energy densities than prior art devices. For example, in some embodiments, the specific capacity may be five times greater than the specific capacity of a conventional flow battery. As used herein, the term "specific capacity" refers to the amount of charge that can be delivered per unit mass. The term "energy density," as used herein, refers to the amount of energy stored per unit mass or per unit volume.

In some embodiments of the invention, the positive electroactive material comprises sulfur or a metal sulfide. The term "metal sulfide," as used herein, refers to chemical compounds having the formula $M_xS_y$, where M is at least one metal element, S is sulfur, x is a number between 0 and 2, and y is a number between 1 and 8. In certain cases, M represents 2 or more metal elements. Exemplary, non-limiting examples of suitable metal elements include lithium, sodium, magnesium, aluminum, zinc, manganese, titanium, and iron. In some embodiments, the metal sulfide comprises a lithium sulfide, a sodium sulfide, a magnesium sulfide, an aluminum sulfide, a zinc sulfide, a manganese sulfide, a titanium sulfide, and/or an iron sulfide. In certain cases, the metal sulfide is $Li_2S$, $Li_2S_2$, $Li_2S_3$, $Li_2S_4$, $Li_2S_6$, or $Li_2S_8$. In some embodiments, the positive electroactive material comprises elemental sulfur.

The redox mediator can be any suitable material to facilitate the oxidation or reduction of the metal sulfide. In some embodiments, the redox mediator can be a polycyclic aromatic hydrocarbon redox mediator. Suitable polycyclic aromatic hydrocarbon redox mediators include, but are not limited to, naphthalene, anthracene, pyrene, phenanthrene, tetracene, chrysene, triphenylene, pentacene, benzopyrenes such as benzo[a]pyrine and benzo[e]pyrene, corannulene, benzoperylene such as benzo[ghi]perylene, fluoranthene, benzofluoranthene such as benzo[b]fluoranthene, benzo[i]fluoranthene and benzo[k]fluoranthene, coronene, ovalene, and perylene. The perylene can be a perylene bisimide or a perylene monoimide. In some embodiments, polycyclic aromatic hydrocarbon redox mediator can be perylene. In some embodiments, polycyclic aromatic hydrocarbon redox mediator can be perylene bisimide. In some embodiments, polycyclic aromatic hydrocarbon redox mediator can be perylene monoimide. In some embodiments, polycyclic aromatic hydrocarbon redox mediator can be perylene bisimide (PBI), or benzo[ghi]peryleneimide (BPI). In some embodiments, the redox mediatior can be a perylenebisimide. In some embodiments, the redox mediator can be a perylene bisimide of Formula I. Benzoperyleneimides useful in the energy storage device of the present invention include benzo[ghi]peryleneimides, and others. In some embodiments, the redox mediator can be a benzo[ghi]perylene imide. Other useful redox mediators can include coronene, coronene diimide, polyoxometalate or a coordination complex.

The polycyclic aromatic hydrocarbon redox mediators of the present invention can be substituted with one or more groups such as, but not limited to, halogen, $C_{1-20}$ alkyl, $C_{1-20}$ haloalkyl, $C_{1-20}$ alkoxy, $C_{1-20}$ heteroalkyl, $C_{3-20}$ carbocycle, $C_{3-20}$ heterocycle, $C_{6-20}$ aryl, $C_{5-20}$ heteroaryl, —N(R³)(R⁴), —OR³, —C(O)R³, —C(O)OR³, —OC(O)R³, —C(O)N(R³)(R⁴), —N(R³)C(O)R⁴, —N(R³)C(O)N(R⁴)(R⁵), —OC(O)N(R⁴)(R⁵), —N(R³)C(O)OR⁴, —SR³, —S(O)R³, —S(O)₂R³, —N₃, —B(OR³)₂, or —SeR³. Alternatively, two groups on adjacent ring atoms can be combined to form —O(CH₂CH₂)$_m$O—, wherein subscript m is an integer from 3 to 10. Each R³, R⁴ and R⁵ can independently be H or $C_{1-20}$ alkyl.

In some embodiments, the redox mediator can be a compound of Formula I described above. In some embodiments, the redox mediator can be a compound of Formula I having the structure:

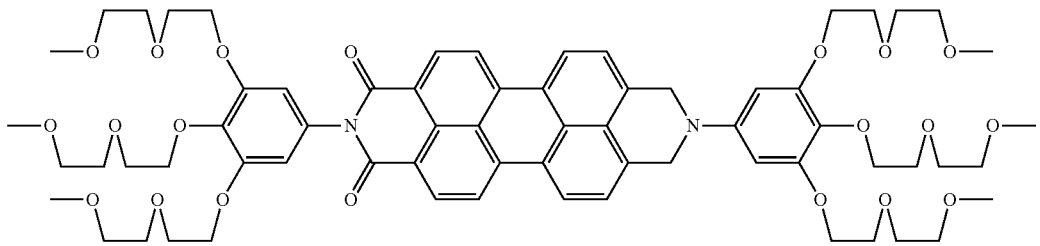

In some embodiments, the redox mediator can be a compound of Formula II described above. In some embodiments, the redox mediator can be a compound of Formula II having the structure:

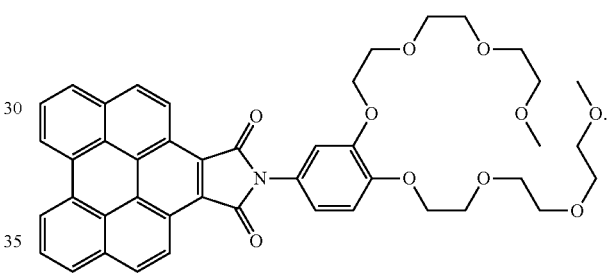

The electrolyte can include any suitable component. For example, the electrolyte can include a metal salt. Examples of suitable metal salts include, but are not limited to, bis(trifluoromethane)sulfonimide lithium salt (LiTFSI), lithium triflate (LiCF₃SO₃), sodium triflate (NaCF₃SO₃), lithium perchlorate (LiClO₄), sodium perchlorate (NaClO₄), lithium hexafluorophosphate (LiPF₆), sodium hexafluorophosphate (NaPF₆), lithium tetrafluoroborate (LiBF₄), and/or sodium tetrafluoroborate (NaBF₄). Other metal salts and ionic liquids suitable in the electrolyte of the present invention are known to one of skill in the art. In some embodiments, the molar concentration of the metal salt in the cathode composition is at least about 0.1 M, at least about 0.2 M, at least about 0.5 M (and/or, in certain embodiments, up to about 1 M, or more).

The metal salt can include any suitable metal as the cation, or any suitable anion. For example, the metal can be any alkali metal, alkali earth metal or transition metal. In some embodiments the metal can be an alkali metal. In some embodiments, the metal cation can be lithium or sodium. In some embodiments, the metal cation can be lithium.

The anion of the metal salt can be any suitable anion. In some embodiments, anion of the metal salt can be bis(trifluoromethyl)sulfonimide, trifluoromethylsulfonate, fluorosulfonimide, perchlorate, tetrafluoroborate, hexafluorophosphate, nitrate, fluoride, chloride, bromide, or iodide. In some embodiments, the metal salt can be lithium bis(trifluoromethyl)sulfonimide, lithium nitrate, or combinations thereof.

The electrolyte can include any suitable component. The electrolyte can include a solvent, an ionic liquid, a cation, an anion, or combinations thereof. Representative solvents include, but are not limited to, tetraethylene glycol dimethyl ether (TEGDME), dimethoxyethane (DME), diglyme, triglyme, dioxolane (DOL), tetrahydrofuran (THF), methyltetrahydrofuran (methyl-THF), ethyl methyl sulfone (EMS), propyl methyl sulfone (PMS), and gamma-butyrolactone (GBL). In some embodiments, the electrolyte can include at least one of diglyme, PGMEA, dimethoxyethane, triglyme, tetraglyme, dioxolane, THF, propylene carbonate, dimethylcarbonate, ethylene carbonate, ethyl methyl sulfone (EMS), propyl methyl sulfone (PMS), water, poly(ethylene oxide) and copolymers thereof, dimethylsulfoxide, N-methylpyrrolidinone, or acetonitrile. In some embodiments, the electrolyte includes diglyme.

The cathode of the present invention can be a solid or non-solid form. In some embodiments, the electrode is flowable. That is, in some embodiments, the electrode may be substantially fluid and/or easily deformed prior to first use and/or when substantially fully charged. For example, in some embodiments, the electrode may have a measurable viscosity, and/or the electrode may tend to flow and to conform to the outline of its container, and/or the electrode may have the consistency of a paste. In some cases, the flowable electrode, after being left undisturbed for a day or less, may be observably deformed from its original shape, and in some cases, such observable deformations may occur on the time scale of minutes or seconds.

In some embodiments, the electrode exhibits the behavior of a Newtonian fluid, e.g., a fluid in which shear stress is directly proportional to shear strain rate (also referred to as shear rate) and viscosity is independent of shear rate. For example, in some cases, an electrode comprising a sulfur or metal sulfide electroactive material dissolved and/or suspended in a fluid may, in the absence of electronically conductive particles, act as a Newtonian fluid.

In some embodiments, the electrode exhibits the behavior of a non-Newtonian fluid, e.g., a fluid whose viscosity is dependent on shear rate. For example, an electrode comprising a sulfur or metal sulfide electroactive material dissolved and/or suspended in a fluid and electronically conductive particles suspended in the fluid may act as a non-Newtonian fluid. In some cases, the addition of even small amounts of a conductive particle may result in non-Newtonian behavior.

The fluid of the electrode composition may be any ionically conductive liquid that can suspend and/or dissolve and transport the sulfur and/or metal sulfide electroactive material and the electronically conductive particles of the electrode composition. In an energy storage device comprising a first electrode comprising the electrode composition, a second electrode, and an ion-permeable separator separating the first and second electrodes, the working ions generally are the ions that are transported through the ion-permeable separator between the first and second electrodes. Ionically conductive liquids typically permit transport of the working ion and have an ionic conductivity of at least about 0.1 mS/cm, or at least about 0.5 mS/cm in some cases. The ionically conductive fluid may generally be referred to as an electrolyte. When an electroactive material is suspended and/or dissolved in the fluid and functions as the positive electrode, the fluid may be referred to as a catholyte. When an electroactive material is suspended and/or dissolved in the fluid and functions as the negative electrode, the fluid may be referred to as an anolyte. The fluid may be either aqueous or non-aqueous.

In some embodiments, the electrode composition may further comprise a supporting electrolyte. One of ordinary skill in the art would understand the term "supporting electrolyte" to refer to a non-electroactive, ionically conductive species. A supporting electrolyte may be added, for example, to increase the conductivity of the electrode composition. In some embodiments, the supporting electrolyte comprises a metal salt described above.

The cathode can also include a conductive additive and other elements. The conductive additive can be any component that improves the conductivity of the cathode. In some embodiments, the cathode also includes a conductive additive. In some embodiments, the conductive additive includes carbon. In some embodiments, the conductive additives comprise carbon-based particles. For example, non-limiting examples of suitable carbon-based, conductive additives include carbon black particles, graphitic carbon, carbon fibers, carbon felt, carbon cloth, carbon microfibers, vapor-grown carbon fibers, fullerenic carbons including "buckyballs," carbon nanotubes, multi-wall carbon nanotubes, single-wall carbon nanotubes, graphene sheets or aggregates of graphene sheets, and materials comprising fullerenic fragments. One of ordinary skill in the art would understand "carbon black" to refer to a form of carbon produced by partial combustion of hydrocarbons. In some embodiments, the conductive additives comprise a metal, a metal carbide, a metal nitride, a metal sulfide, and/or a metal oxide. In some embodiments, the metal comprises platinum, palladium, iridium, gold, silver, ruthenium, tantalum, tin, aluminum, a first-row transition metal, and/or alloys comprising one or more of these elements. In some embodiments, the metal carbide comprises a carbide of a first-row transition metal, of silicon, of tin, of tantalum, a mixed-metal carbide comprising one or more of these metals, and/or a mixture of different metal carbides. In one embodiment, the metal carbide is titanium carbide. In some embodiments, the metal nitride comprises a nitride of a first-row transition metal, a mixed-metal nitride comprising one or more of these metals, and/or a mixture of different metal nitrides. In one embodiment, the metal nitride is titanium nitride. In some embodiments the metal oxide comprises an oxide of a first-row transition metal, ruthenium oxide, tin oxide, or zinc oxide. In some embodiments the conductive oxide comprises an oxide usable as a transparent conducting oxide (TCO), including but not limited to indium tin oxide (ITO). In some embodiments, the nanoscale particles are substantially spherical, and/or have an aspect ratio (largest to smallest crosssectional dimension of the particle) of less than about 3, less than about 2, less than about 1.5, less than about 1.2, etc. In other embodiments, the nanoparticles have an aspect ratio greater than about 3 and include nanotubes, nanorods, nanowires, and nanoplatelets. The nanoscale particles may be prepared by a variety of methods including mechanical grinding, chemical precipitation, vapor phase reaction, laser-assisted reactions, and bio-assembly.

In some embodiments, the conductive additives are nanoscale particles. As noted above, the small size of the conductive additives may facilitate the formation of stable suspensions and/or may lower the percolation threshold. In some embodiments, the conductive additives have a primary particle size of less than about 1 micrometer, less than about 500 nm, less than about 100 nm, less than about 50 nm, less than about 30 nm, or less than about 20 nm (and/or, in certain embodiments, down to about 10 nm, or less). In some embodiments, the conductive additives have a primary particle size of at least about 10 nm, at least about 20 nm, at least about 30 nm, at least about 50 nm, at least about 100 nm, or at least about 500 nm (and/or, in certain embodiments, up to about 1 micrometer, or more). Combinations of these are also possible. In some embodiments, for instance, the conductive additives have a primary particle size in the range of about 10 nm to about 30 nm, about 10 nm to about 50 nm, about 10 nm to about 100 nm, about 10 nm to about 500 nm, about 10 nm to about 1 micrometer, about 50 nm to about 100 nm, about 50 nm to about 500 nm, about 50 nm to about 1 micrometer, about 100 nm to about 500 nm, or about 100 nm to about 1 micrometer. The primary particle size of a non-spherical particle may be taken as the diameter of a perfect sphere having the same volume as the particle.

The energy storage device of the present invention also includes any suitable membrane separator. The energy storage device may, additionally, comprise an ion-permeable separator between the first and second electrode compartments. The ion-permeable separator can include any suitable medium capable of allowing the working ion(s) of the energy storage device to be passed through it. In some embodiments, the ion-permeable medium comprises a membrane. The membrane can be any conventional membrane that is capable of ion transport. In some embodiments, the membrane may be a liquid-impermeable membrane that permits the transport of ions therethrough, namely a solid or gel ionic conductor. In other embodiments the membrane is a porous polymer membrane infused with a liquid that allows for the shuttling of ions between the first and second electroactive materials, while preventing the transfer of electrons. In some embodiments, the membrane is a microporous membrane that prevents particles forming the positive and negative electrode flowable compositions from crossing the membrane. Exemplary membrane materials include polyethyleneoxide (PEO) polymer in which a lithium salt is complexed to provide lithium conductivity, or Nafion membranes, which are proton conductors. For example, PEO-based electrolytes can be used as the membrane, which is pinhole-free and a solid ionic conductor, optionally stabilized with other membranes such as glass fiber separators as supporting layers. PEO can also be used as a slurry stabilizer, dispersant, etc. in the positive or negative flowable redox compositions.

The energy storage device also includes a current collector. The current collector can be any suitable element that is electrically conductive. In some embodiments, the current collector comprises at least one of carbon cloth, carbon felt, carbon paper, carbon particles, carbon nanomaterial, metal chalcogenide, metal, and metal oxide.

In some embodiments, the energy storage device includes the anode comprising lithium, the cathode comprising $Li_2S_8$, the redox mediator having the structure:

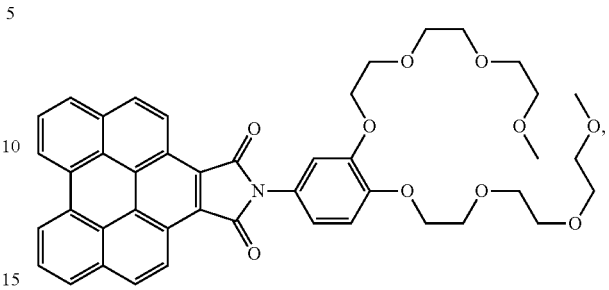

diglyme, lithium bis(trifluoromethyl)sulfonimide, and lithium nitrate. The energy storage device can also include the membrane separator, and the current collector.

In some embodiments, the energy storage device includes the anode comprising lithium, the cathode comprising $Li_2S_8$, the redox mediator having the structure:

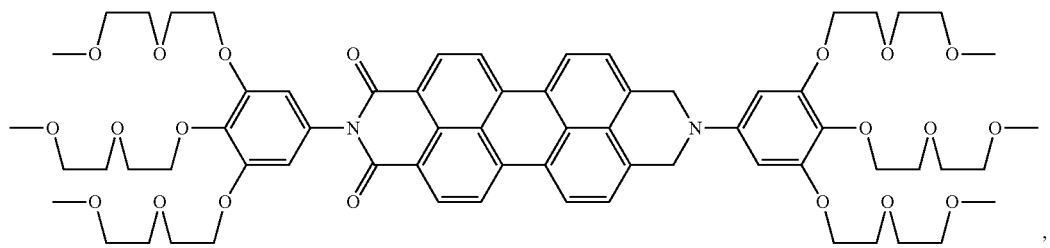

diglyme, lithium bis(trifluoromethyl)sulfonimide, and lithium nitrate. The energy storage device can also include the membrane separator, and the current collector.

The present invention also provides electrode compositions having a metal sulfide $M_xS_y$, wherein M is a metal, subscript x is from 0 to 2 and y is from 1 to 8, a redox mediator having a redox potential suitable for reducing or oxidizing $M_xS_y$, and an electrolyte. In some embodiments, the present invention includes an electrode composition having a metal sulfide $M_xS_y$, wherein M is a metal, subscript x is from 0 to 2 and y is from 1 to 8, a redox mediator having a redox potential suitable for reducing or oxidizing $M_xS_y$, and an electrolyte.

V. Examples

All manipulations involving lithium metal were performed in an Ar-filled glove box with water and $O_2$ content below 2.0 ppm. $^1H$ and $^{13}C$ NMR spectra are reported in δ (parts per million) relative to tetramethylsilane (TMS), and referenced to residual $^1H/^{13}C$ signals of the deuterated solvent ($^1H$ (δ) chloroform 7.27; $^{13}C$ (δ) chloroform 77.23).

Instrumentation. Water content was tested with a Mettler Toledo C20 Coulometric KF Titrator Karl-Fischer apparatus. Column chromatography was performed using Biotage HPFC SP4 Flash Purification System with Biotage SNAP cartridges containing KP-Sil. $^1H$ and $^{13}C$ NMR spectra were obtained with a Bruker Avance II 500 MHz NMR Spectrometer. UV-visible-NIR spectra were measured with a Cary 5000 UV-Vis-NIR spectrophotometer. FT-IR spectra were measured with a Perkin Elmer Spectrum One FT-IR spectrometer. MALDI-TOF mass spectrometry was obtained with an AB SCIEX TF4800 MALDI TOF-TOF Mass Spectrometer. Elemental analyses were performed by the University of California, Berkeley College of Chemistry Microanalytical Facility. Electrochemical experiments and battery testing were conducted with a BioLogic VMP3 potentiostat. SEM micrographs were obtained with a Zeiss Gemini Ultra-55 Analytical Field Emission Scanning Electron Microscope. Glassy carbon disc electrodes with a diameter of 1 mm were obtained from BAS Inc. (West Lafayette, Ind.) and polished before use.

Materials. Tri(ethylene glycol) monomethyl ether tosylate, benzoperylene anhydride, and 20% $HNO_3.SiO_2$ were synthesized according to literature procedures. Diethylene glycol dimethyl ether (diglyme), Pd/C, 18-Crown-6, imidazole, and lithium metal were purchased from Sigma Aldrich. Lithium nitrate, sulfur (Puratronic, 99.9995% (metals basis)), and lithium sulfide (99.9% (metals basis)) were purchased from Alfa Aesar. Lithium bis(trifluoromethanesulfonyl)imide (LiTFSI) was purchased from 3M. Carbon felt was purchased from Fuel Cell Store, AvCarb1071HBC.

Electrolyte and polysulfide preparation. Electrolyte refers to 0.50 M LiTFSI and 0.15 M $LiNO_3$ in diglyme unless otherwise specified. LiTFSI was dried for 16 h under vacuum at 150° C. $LiNO_3$ was dried for 16 h under vacuum at 110° C. Diglyme was tested for peroxides prior to use. Diglyme was dried with activated 3 Å molecular sieves until it measured <20 ppm $H_2O$. Electrolyte was tested for water content and confirmed to contain <30 ppm water before use. Solutions of $Li_2S_8$ (2.5 M sulfur in electrolyte) were prepared by mixing $Li_2S$ (0.144 g, 3.13 mmol), sulfur (0.701 g, 2.73 mmol), and 10 mL of electrolyte and heating at 60° C. until all solids were dissolved. $Li_2S_8$ solutions were kept at 60° C. in order to prevent precipitation of insoluble species and cooled to room temperature prior to use.

Example 1. Preparation of Redox Mediator PBI 1

The preparation of PBI 1 is provided below.

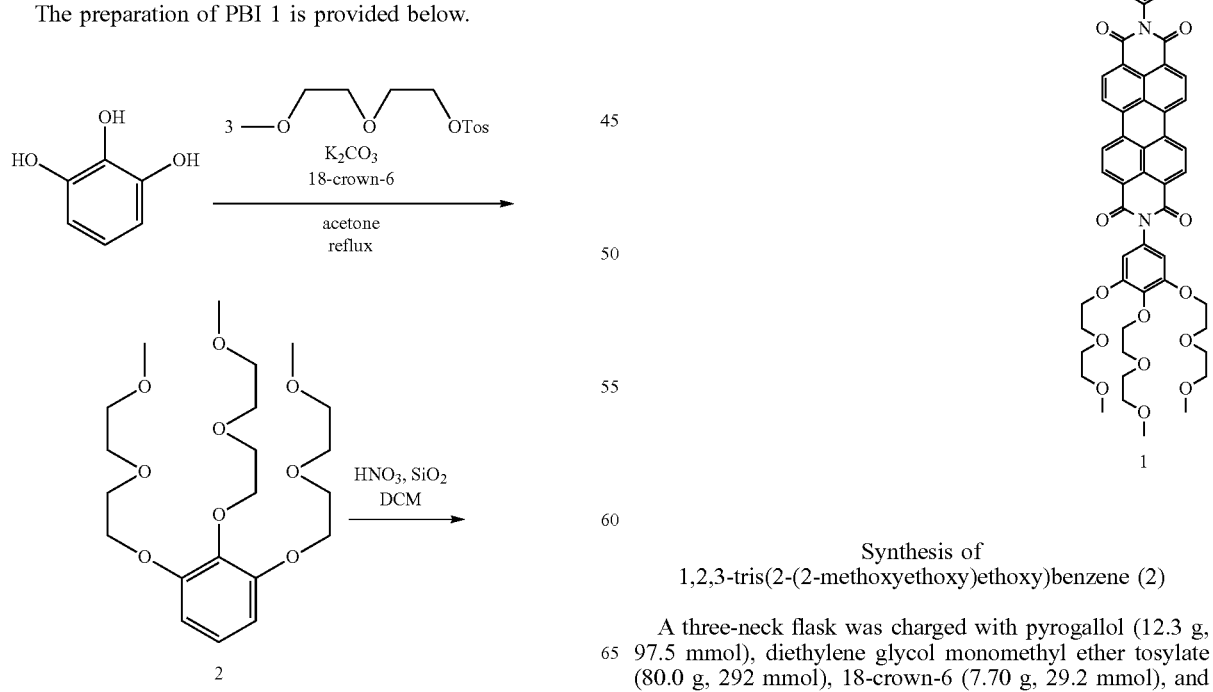

Synthesis of 1,2,3-tris(2-(2-methoxyethoxy)ethoxy)benzene (2)

A three-neck flask was charged with pyrogallol (12.3 g, 97.5 mmol), diethylene glycol monomethyl ether tosylate (80.0 g, 292 mmol), 18-crown-6 (7.70 g, 29.2 mmol), and acetone (350 mL). The flask was fit with a reflux condenser, and the solvent was sparged with $N_2$. After 30 min of sparging, pulverized and oven-dried $K_2CO_3$ (67.3 g, 487 mmol) was added, and the reaction was heated at 80° C. for 97 h. The beige colored suspension was cooled to room temperature, filtered, and rinsed with acetone. The filtrate was collected, concentrated under vacuum, dissolved in diethyl ether (400 mL), and washed with saturated $NaHCO_3$ (2×200 mL). The organic layer was collected, concentrated under vacuum, and dried under high vacuum to yield 2 as a pale brown oil (28.0 g, 66%). Compound 2 was used without further purification in the following reaction. Analytically pure samples were prepared by column chromatography with n-hexane/EtOAc as eluent ($SiO_2$, 20-100% EtOAc gradient). $^1$H NMR ($CDCl_3$) δ6.92 (t, 1H, $J_{HH}$=7 Hz ArH), 6.58 (d, 2H, $J_{HH}$=7 Hz, ArH), 4.16 (t, 6H, $J_{HH}$=5 Hz, $OCH_2$), 3.86 (t, 4H, $J_{HH}$=5 Hz, $OCH_2$), 3.81 (t, 2H, $J_{HH}$=5 Hz, $OCH_2$), 3.74-3.71 (m, 6H, $OCH_2$), 3.57-3.55 (m, 6H, $OCH_2$), 3.39 (s, 9H, $OCH_3$); $^{13}$C {$^1$H} NMR ($CDCl_3$) δ153.0, 138.6, 123.7, 107.9, 72.5, 72.22, 72.15, 70.9, 70.7, 70.6 69.9, 68.9, 59.25, 59.22; UV/vis ($CHCl_3$): $\lambda_{max}$/nm (ε/L $mol^{-1}$ $cm^{-1}$): 269 (700); FT-IR (neat) $\bar{v}$ ($cm^{-1}$) 2933, 2876, 2825, 1594, 1472, 1455, 1355, 1302, 1255, 1199, 1099, 1025, 933, 849; MS (MALDI-TOF, DCTB) m/z=471.17 [2+K]$^+$, 455.20 [2+Na]$^+$, 432.21 [2]$^+$; Anal Calc'd for $C_{21}H_{36}O_9$: C, 58.32; H, 8.39; Found: C, 58.08; H, 8.49.

Synthesis of 1,2,3-tris(2-(2-methoxyethoxy)ethoxy)-5-nitrobenzene (3)

A round bottom flask was charged with 2 (7.86 g, 18.2 mmol) and DCM (50 mL). Upon dissolution of 2, $SiO_2$ (8.0 g) was added, and the flask was fit with an addition funnel loaded with $HNO_3$ (10 mL, 16 mol $L^{-1}$). $HNO_3$ was added over 5 min to the stirring suspension of 3 and $SiO_2$. The deep red suspension was stirred for an additional 15 min then added to a separatory funnel and diluted with 50 mL of $H_2O$. The bottom organic fraction was collected and carefully washed with saturated $NaHCO_3$ (2×50 mL). The organic layer was then dried with $MgSO_4$, filtered, concentrated, and subject to column chromatography with DCM/MeOH as eluent ($SiO_2$, 1-8% MeOH gradient) to yield 3 as a dark yellow oil (2.83 g, 33%). $^1$H NMR ($CDCl_3$) δ7.53 (s, 2H, ArH), 4.28 (t, 2H, $J_{HH}$=5 Hz, $OCH_2$), 4.22 (t, 4H, $J_{HH}$=5 Hz, $OCH_2$), 3.71-3.68 (m, 6H, $OCH_2$), 3.56-3.51 (m, 6H, $OCH_2$), 3.37 (s, 6H, $OCH_3$), 3.35 (s, 3H, $OCH_3$); $^{13}$C{$^1$H} NMR ($CDCl_3$) δ152.4, 144.3, 143.3, 103.5, 73.0, 72.21, 72.16, 71.0, 70.8, 70.7, 69.7, 69.4, 59.30, 59.24; UV/vis ($CHCl_3$): $\lambda_{max}$/nm (ε/L $mol^{-1}$ $cm^{-1}$): 326 (6000); FT-IR (neat) $\bar{v}$ ($cm^{-1}$) 2931, 2876, 2822, 1618, 1519, 1492, 1438, 1336, 1319, 1244, 1200, 1098, 1026, 927, 850; MS (MALDI-TOF, DCTB) m/z=516.15 [3+K]$^+$, 500.18 [3+Na]$^+$; Anal Calc'd for $C_{21}H_{35}NO_{11}$: C, 52.82; H, 7.39; N, 2.93; Found: C, 52.52; H, 7.54; N, 2.92.

Synthesis of 3,4,5-tris(2-(2-methoxyethoxy)ethoxy)aniline (4)

A round bottom flask was charged with 3 (4.65 g, 9.74 mmol), Pd/C (10% w/w, 450 mg), and 50 mL of MeOH. The suspension was evacuated and purged with $H_2$ three times then allowed to stir under an $H_2$ atmosphere for 18 h. Filtration of the suspension through Celite followed by concentration under reduced pressure yielded 4 as a brown oil (4.28 g, 98%). Analytically pure samples were prepared by column chromatography with EtOAc/MeOH as eluent ($SiO_2$, 0-10% MeOH gradient). Broadening of the $NH_2$ protons due to H-bonding prevented their assignment; $^1$H NMR ($CDCl_3$) δ5.96 (s, 2H, ArH), 4.11 (t, 4H, $J_{HH}$=5 Hz, $OCH_2$), 4.06 (t, 2H, $J_{HH}$=5 Hz, $OCH_2$), 3.84 (t, 4H, $J_{HH}$=5 Hz, $OCH_2$), 3.78 (t, 2H, $J_{HH}$=5 Hz, $OCH_2$), 3.73-3.71 (m, 6H, $OCH_2$), 3.58-3.55 (m, 6H, $OCH_2$), 3.39 (s, 9H, $OCH_2$); $^{13}$C {$^1$H} NMR ($CDCl_3$) δ153.4, 142.8, 131.2, 95.5, 72.7, 72.3, 72.2, 70.9, 70.7, 70.6, 69.9, 68.8, 59.29, 59.25; UV/vis ($CHCl_3$): $\lambda_{max}$/nm (ε/L $mol^{-1}$ $cm^{-1}$): 288 (3435), 396 (895); FT-IR (neat) $\bar{v}$ ($cm^{-1}$) 3243, 2927, 2875, 2817, 1607, 1591, 1505, 1448, 1352, 1239, 1199, 1098, 1025, 934, 846; MS (MALDI-TOF, DCTB) m/z=486.05 [4+K]$^+$, 470.08 [5+Na]$^+$; Anal Calc'd for $C_{21}H_{37}NO_9$: C, 56.36; H, 8.33; N, 3.13; Found: C, 55.98; H, 8.49; N, 3.35.

Synthesis of PBI 1

A round bottom flask was charged with 4 (1.70 g, 3.84 mmol), 3,4,9,10-perylene tetracarboxylic dianhydride (685 mg, 1.75 mmol), Zn(OAc)$_2$ (242 mg, 1.75 mmol), and imidazole (25 g). The flask containing the reaction mixture was evacuated and refilled with $N_2$ three times then heated at 140° C. After 3 h the reaction was removed from heat, allowed to cool to ~80° C., and 50 mL of $CHCl_3$ was carefully added. The deep red solution was poured into a separatory funnel, the volume of $CHCl_3$ increased to 150 mL, and the organic layer was washed with aqueous HCl (2.0 mol $L^{-1}$, 2×200 mL). The organic phase was collected, concentrated under vacuum, and purified by column chromatography with DCM/MeOH as eluent ($SiO_2$, 0-10% MeOH gradient). PBI 1 was isolated as a deep red solid (1.68 g, 77%). $^1$H NMR ($CDCl_3$) δ8.50 (br d, 4H, $J_{HH}$=7 Hz, ArH), 8.18 (br s, 4H, ArH), 6.69 (s, 4H, ArH), 4.27 (t, 4H, $J_{HH}$=5 Hz, $OCH_2$), 4.10 (bt, 8H, $J_{HH}$=5 Hz, $OCH_2$), 3.90 (t, 4H, $J_{HH}$=5 Hz, $OCH_2$), 3.83-3.80 (m, 12H, $OCH_2$), 3.72-3.70 (m, 8H, $OCH_2$), 3.64-362 (m, 4H, $OCH_2$), 3.57-3.55 (m, 8H, $OCH_2$), 3.44 (s, 6H, $OCH_3$), 3.38 (s, 12H, $OCH_3$); $^{13}$C{$^1$H} NMR ($CDCl_3$) δ162.9, 153.2, 138.3, 133.8, 131.0, 130.2, 128.6, 125.5, 123.3, 123.0, 108.0, 72.8, 72.3, 72.2, 70.84, 70.79, 70.7, 69.8, 69.0, 59.28, 59.24; UV/vis ($CHCl_3$): $\lambda_{max}$/nm (ε/L $mol^{-1}$ $cm^{-1}$): 261 (26932), 369 (3639), 463 (16293), 493 (42001), 529 (53132); FT-IR (neat) $\bar{v}$ ($cm^{-1}$) 2959, 2924, 2870, 1698, 1661, 1576, 1463, 1441, 1402, 1350, 1318, 1247, 1220, 1181, 1103, 984, 929, 851, 809; MS (MALDI-TOF, DCTB) m/z=1289.16 [1+K]$^+$, 1273.20 [1+Na]$^+$; Anal Calc'd for $C_{66}H_{78}N_2O_{22}$: C, 63.35; H, 6.28; N, 2.24; Found: C, 62.99; H, 6.49; N, 2.29.

Example 2. Computational Details

The ionization energies ($E_i$) and electron affinities ($E_{ea}$) were calculated using Density Functional Theory (DFT) within a polarizable continuum medium model (with the dielectric constant set to that of water, 78.2) as implemented in the QChem software package. For all molecules, the adiabatic method was employed in which the geometry was optimized separately for each charge state before performing an energy calculation. Due to the computational complexity in converging large molecules versus small ones within a high-throughput context, separate computational workflows were applied for small molecules (<50 atoms) versus larger molecules (50 atoms or higher). For small molecules, we performed geometry optimization, vibrational frequency analysis, and energy evaluation at the B3LYP/6-31+G* level of theory. For larger molecules, we performed geometry optimization at the PBE/6-31+G* level of theory[4] followed by an energy evaluation at the B3LYP/6-31+G* level. In a previous study, we have determined that both strategies produce comparable accuracy, and that using the PBE functional for the geometry optimization portion of large molecules reduces computation time and improves convergence percentage.

It is noted that the computed $E_i$ and $E_{ea}$ represent the absolute oxidation and reduction potentials, respectively. To obtain the oxidation potential relative to a reference electrode, we subtract the absolute potential of the reference electrode from this value, $E_{oxd}°=E_i-E_{ref}°$. Similarly, the reduction potential is calculated by $E_{red}°=E_{ea}-E_{ref}°$. The reference potential for Li ($E_{ref}°$) was set to 1.4 eV.

Overall, 85 structures were computed that span an $E_{ea}$ range of 0.19 to 3.08 V vs. Li/Li$^+$ and $E_i$ range of 3.14 to 6.08 V vs. Li/Li$^+$.

Example 3. Electrochemistry

Cyclic Voltammetry. Our electrochemical cell was configured with a glassy carbon working electrode and lithium metal reference and counter electrodes. Working solutions for cyclic voltammetry (CV) were separated from lithium counter and reference electrodes with a glass frit with an average pore size of ~7 nm and thickness of 5 mm obtained from Advanced Glass and Ceramics (St. James, N.C., USA). In order to account for the potential drop across a highly resistive frit, all CV measurements were corrected for iR drop by measuring the impedance between the working and reference electrodes with an applied AC voltage with frequency of 100 MHz and correcting for 85% of the expected iR drop. CV of polysulfide alone and PBI 1 with polysulfide were conducted in electrolyte with 0.010 mol L$^{-1}$ PBI 1 and 0.010 mol S L$^{-1}$ of nominal composition Li$_2$S$_8$. CVs of PBI 1 was conducted with 0.010 mol L$^{-1}$ PBI 1 in electrolyte.

Interdigitated Array IV Measurements.

A drop of catholyte (5 µL) was introduced to the IDA, covering the electrodes entirely. The concentration of Li$_2$S$_8$ was 0.50 mol S L$^{-1}$ and PBI 1 concentration was 0.050 mol L$^{-1}$. The concentration of polysulfide was reduced five-fold from the concentration used for battery cycling to minimize hysteresis that is likely attributed to nucleation of insulating S$_8$ or Li$_2$S on the electrode when cycling the voltage bias in the ±0.5 V range from the open circuit potential.

Battery Preparation with PBI 1 Additive.

PBI 1 (15.0 mg) was heated at 120° C. for 30-60 min in 0.172 mL of electrolyte (TEGDME, 0.50 mol L$^{-1}$ LiTFSI, 0.15 mol L$^{-1}$ LiNO$_3$) until complete dissolution followed by cooling to room temperature. A solution of nominal composition Li$_2$S$_8$(1.0 mol L$^{-1}$, or 8.0 mol S L$^{-1}$) was prepared in the same electrolyte and kept at 60° C. to prevent gradual precipitation. The Li$_2$S$_8$ solution was cooled to room temperature and then 0.078 mL was added to the solution of PBI 1 followed by manual stirring with a spatula and brief vortexing yielding a viscous deep purple solution. Mixing was completed in less than two minutes to allow for manipulation of the catholyte as a liquid prior to gelation. Gelation generally occurred within 5 min of mixing the polysulfide solution with the PBI 1 solution. Roughly 0.020 mL of catholyte was then pipetted into the gold-coated well (0.5 mm deep, 6.35 mm diameter) of the nickel electrode to give a final catholyte mass of 15-22 mg, whose final composition was 5.0% w/w PBI 1 (0.048 mol L$^{-1}$) and 0.313 mol L$^{-1}$Li$_2$S$_8$ (i.e., 2.50 mol S L$^{-1}$). The catholyte was allowed to rest in the cathode well for a minimum of 30 min prior to battery assembly. Gelation results in a catholyte that is stable to inversion and has a glassy black appearance.

Lithium anodes were prepared by punching out 12.7 mm diameter circles from 1.5 mm thick lithium foil, pressing them onto nickel electrodes, and treating the exposed surface with electrolyte (TEGDME, 0.50 mol L$^{-1}$ LiTFSI, and 0.15 mol L$^{-1}$ LiNO$_3$) for a minimum of 30 min. A 12.7 mm diameter circle of Tonen separator was then placed on top of the lithium anode and an additional drop of electrolyte was added (~0.015 mL) before electrode assembly.

Battery Preparation with No Additive.

All procedures were identical to PBI 1 battery preparation with the exception that no PBI 1 was added to the initial 0.172 mL electrolyte solution.

Determination of Densities.

The density of electrolyte with and without dissolved polysulfides was measured by weighing at least five samples each with a known volume (5.00 mL) at room temperature. The measured densities were 1.084±0.003 g mL$^{-1}$ for electrolyte only and 1.121±0.001 g mL$^{-1}$ for electrolyte containing 2.5 mol S L$^{-1}$ as Li$_2$S$_8$.

Calculation of C-rates for 2.8 to 2.0 V cycling. The 2.8 to 2.0 V window nominally covers the overall reduction process depicted in equation (1).

$$S_8+4e^-+4Li^+\rightarrow 2Li_2S_4 \quad (1)$$

Based on equation (1), all C-rates are calculated for the reaction of 0.5 mol of Li$^+$ per 1.0 mol of S (or 0.5 mol e$^-$). Current for C/8 galvanostatic cycling was set with equations (2) and (3):

$$\frac{m_{catholyte} \times \text{wt}\%_{Li2S8\ electrolyte\ solution} \times M_S}{\rho_{Li2S8\ electrolyte\ solution} \times 0.001\ L\ mL^{-1}} = n_{mol\ of\ S} \quad (2)$$

$$n_{mol\ of\ S} \times 0.5_{mol\ e^-\ per\ mol\ S} \times 96485C\ mol^{-1}_{e^-}/28800s=i \quad (3)$$

The variables in equations (2) and (3) are defined as follows: $m_{catholyte}$=mass of catholyte; wt$\%_{Li2S8\ electrolyte\ solution}$=weight percent of the catholyte that is Li$_2$S$_8$ and electrolyte (0.95 with 5% w/w PBI 1, 1.0 for Li$_2$S$_8$ alone); $M_s$=molarity of S.

Calculation of Energy Density.

Figure 1:
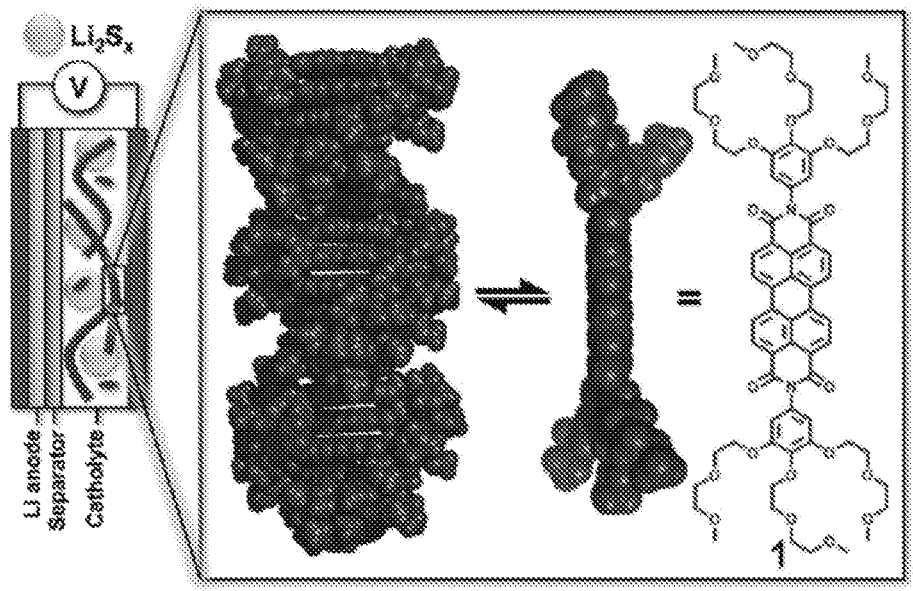
FIG. 1 shows a Li—S cell diagram of nanostructured perylene bisimide-polysulfide (PBI 1-PS) catholyte with side-on view of the PBI π-surface and its self-assembly into 1-D nanowires through it-stacking.
Figure 2:
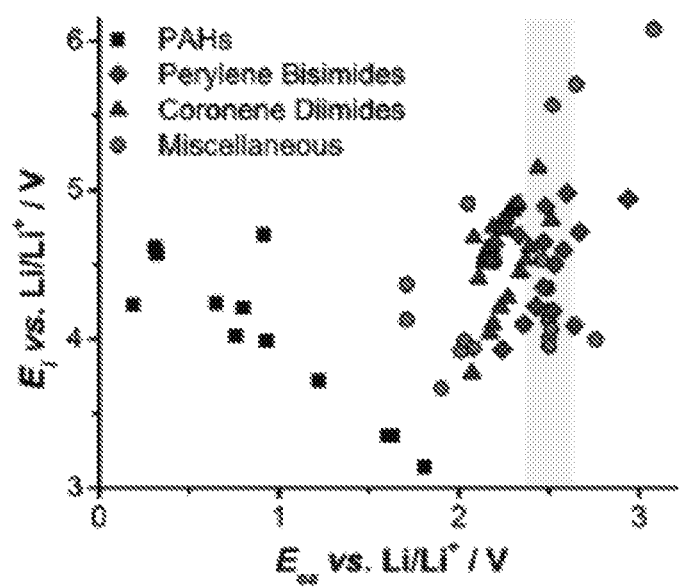
FIG. 2 shows a plot of E$_1$ vs. E$_{ea}$ calculated for candidate n-gelators. The yellow bar highlights the voltage window of interest for matching the calculated E$_{ea}$ of the redox mediator to the S$_8$/S$_4^{2-}$ redox couple.
Figure 3:
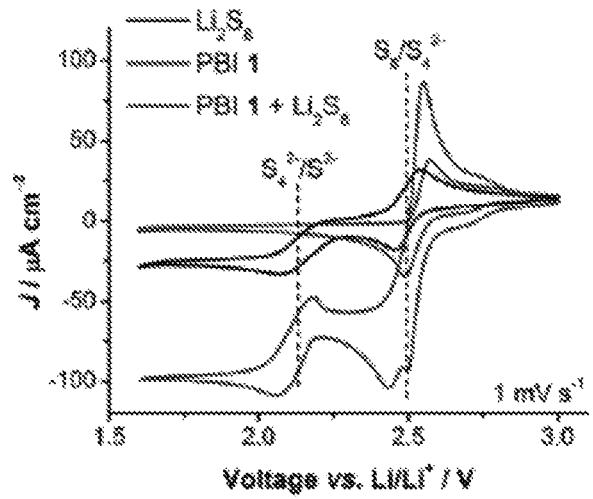
FIG. 3 shows a cyclic voltammograms of Li$_2$S$_8$, PBI 1, and PBI 1+Li$_2$S$_8$ in TEGDME with LiTFSI (0.50 mol L$^{-1}$) and LiNO$_3$ (0.15 mol L$^{-1}$) as electrolyte. The concentration of PBI 1 is 0.010 mol L$^{-1}$ and Li$_2$S$_8$ is 0.010 mol S L$^{-1}$ in all voltammograms.
Figure 4:
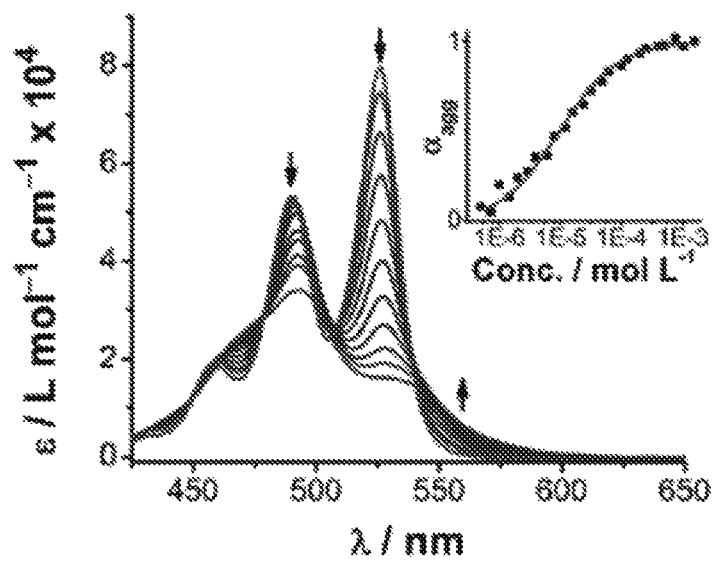
FIG. 4 shows a concentration dependent UV-Vis spectra of PBI 1 in electrolyte. Arrows indicate changes with increasing concentration. Inset: non-linear curve fitting of the concentration series at λ=555 nm (expressed as the degree of aggregation α$_{agg}$) to an isodesmic self-assembly model yielding K$_α$=6.1×10$^4$ L mol$^{-1}$.
Figure 5:
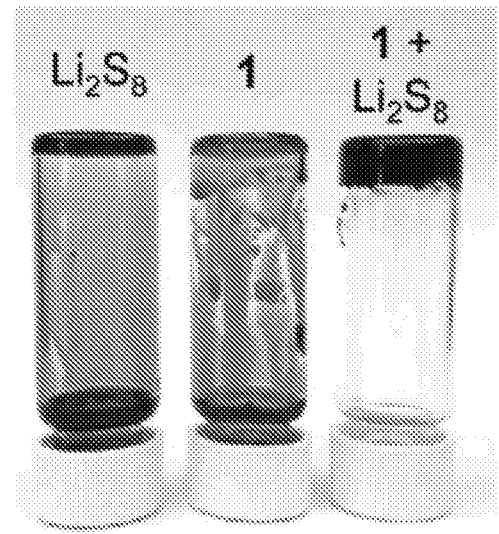
FIG. 5 shows a picture of Li$_2$S$_8$, PBI 1, and PBI 1+Li$_2$S$_8$ in electrolyte, showing unique gelation behavior for PBI 1+Li$_2$S$_8$.
Figure 6:
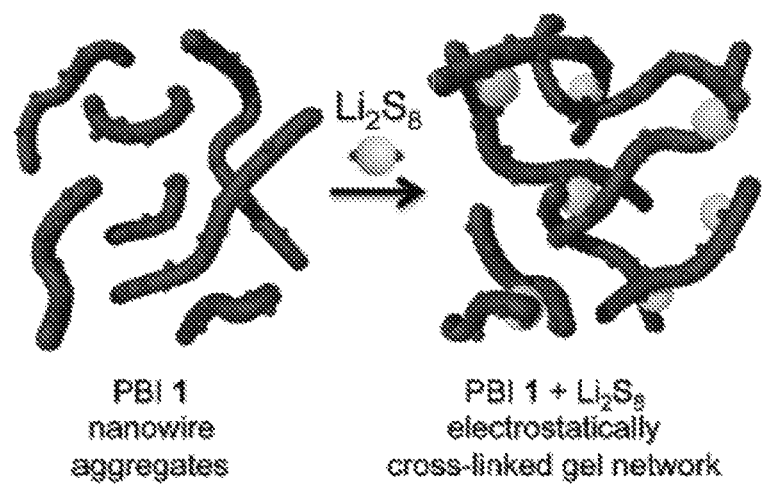
FIG. 6 shows an electrostatic cross-linking of the nanowire aggregates is triggered by addition of Li$_2$S$_8$ resulting in a gel with high local concentration of PS immobilized on the redox mediator network.
Figure 7:
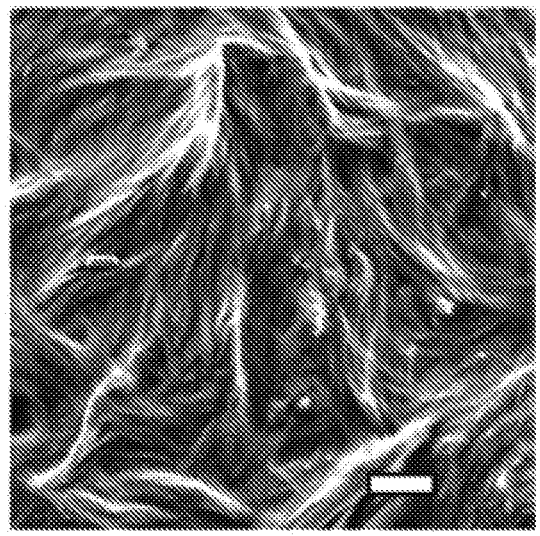
FIG. 7 shows a xerogel of the nanofiber network formed from PBI 1+Li$_2$S$_8$ (scale bar is 1 μm).
Figure 8:
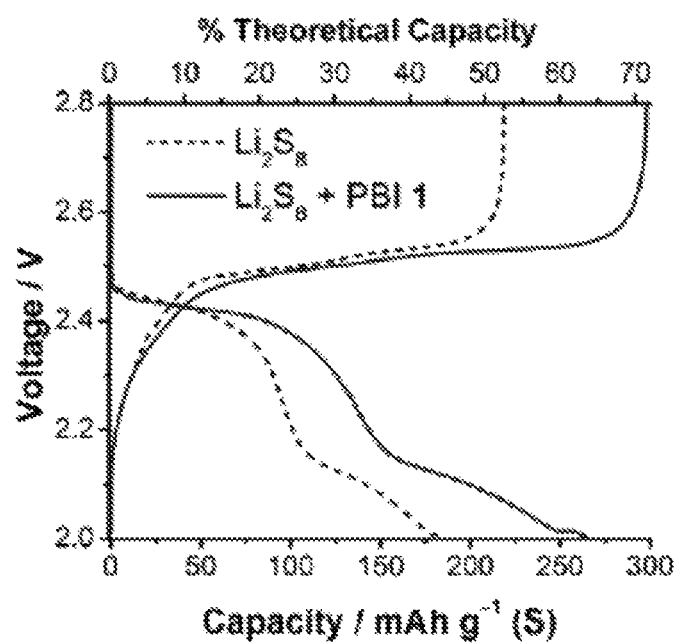
FIG. 8 shows charge-discharge profiles from galvanostatic cycling (second cycle) at a C/8 rate showing a 38% increase in discharge capacity for PBI 1+Li$_2$S$_8$.
Figure 9:
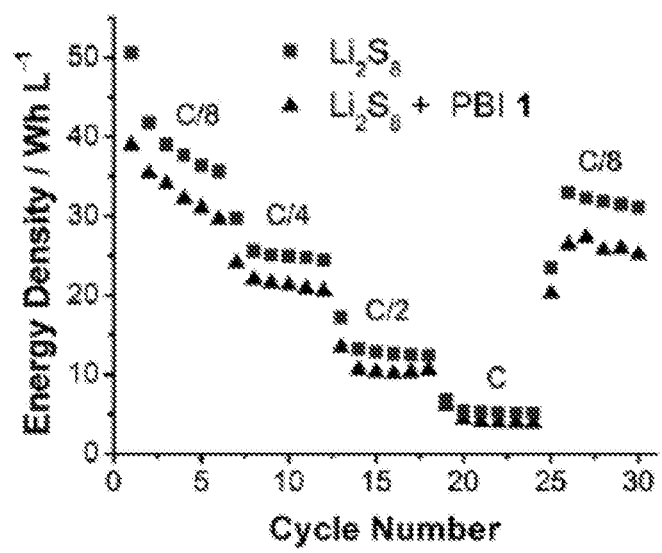
FIG. 9 shows rate performance at C/8, C/4, C/2, and 1C for PBI1+Li$_2$S$_8$.
Figure 10:
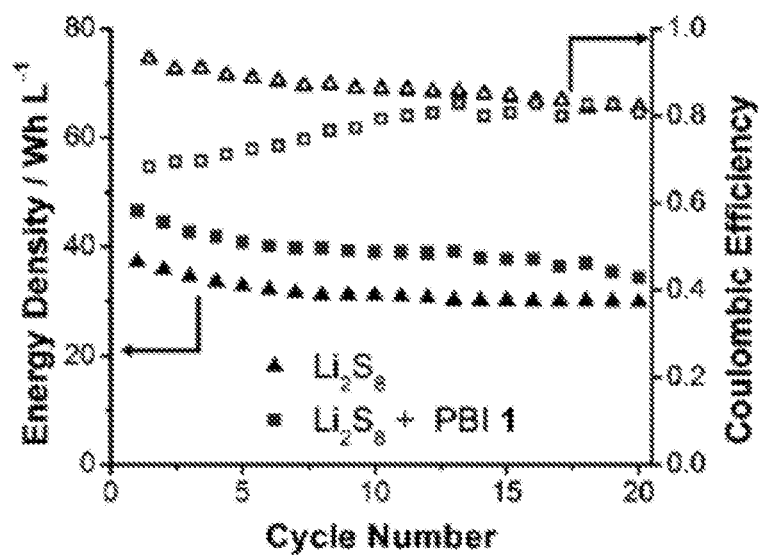
FIG. 10 shows energy density (solid) and Coulombic efficiency (hollow) vs. cycle number at C/8 rate for PBI 1+Li$_2$S$_8$.
Figure 11:
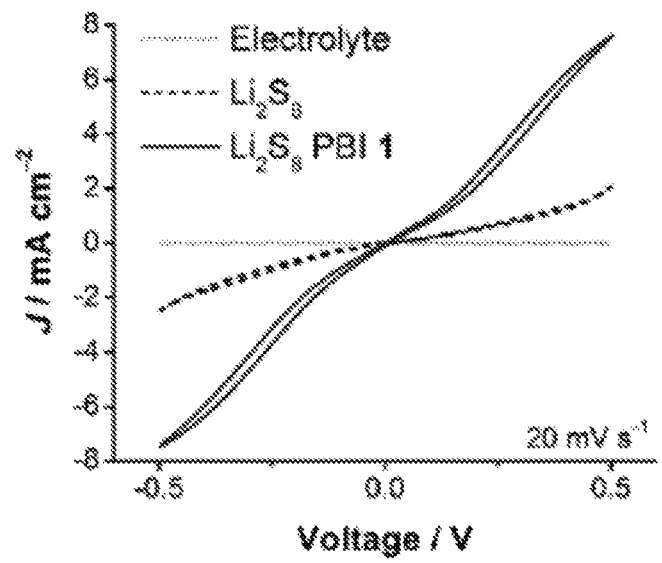
FIG. 11 shows IV curves from cyclic voltammetry with an interdigitated array electrode.
Figure 12:
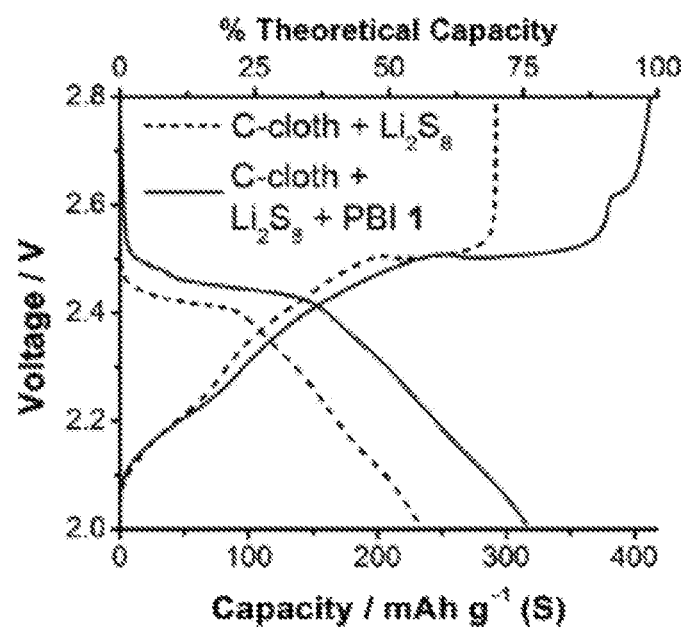
FIG. 12 shows a charge-discharge profiles from galvanostatic cycling (second cycle) at a C/8 rate showing a 31% increase in discharge capacity for C-cloth+Li$_2$S$_8$+PBI 1.
Figure 13:
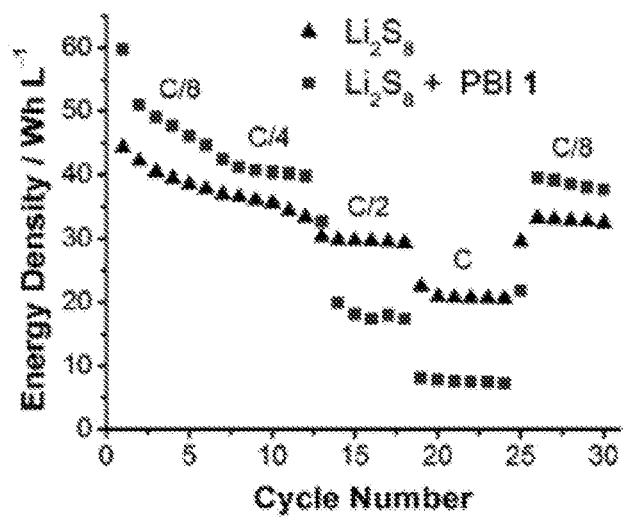
FIG. 13 shows rate performance at C/8, C/4, C/2, and 1C for C-cloth+Li$_2$S$_8$+PBI 1.
Figure 14:
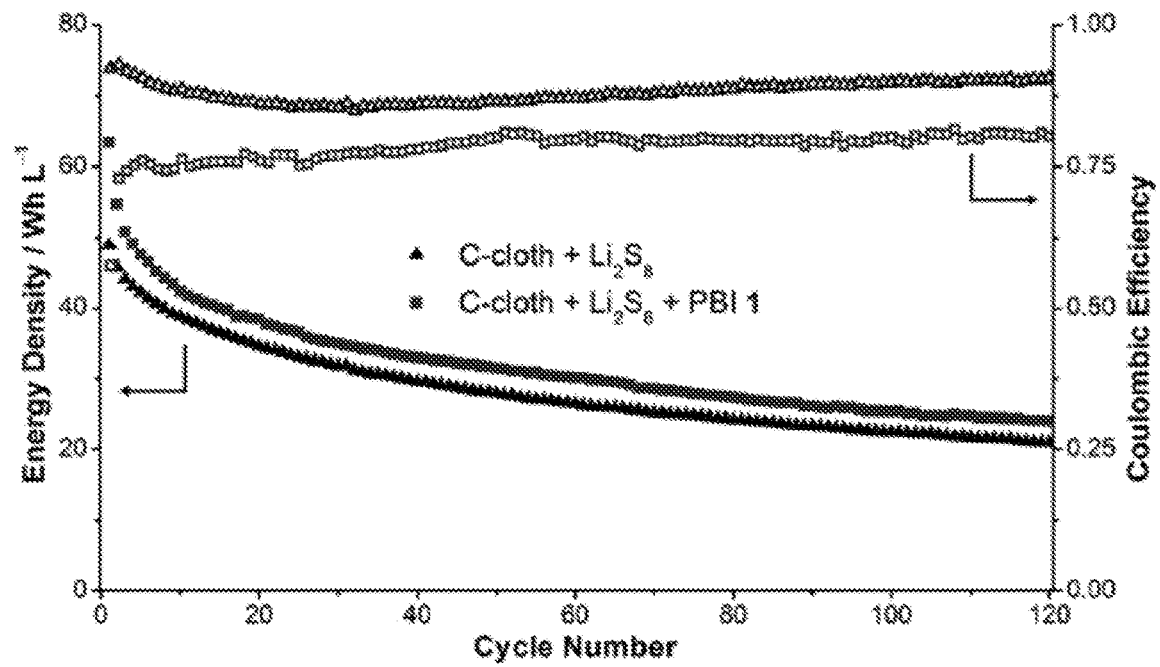
FIG. 14 shows energy density (solid) and Coulombic efficiency (hollow) vs. cycle number at C/4 rate.
Figure 15:
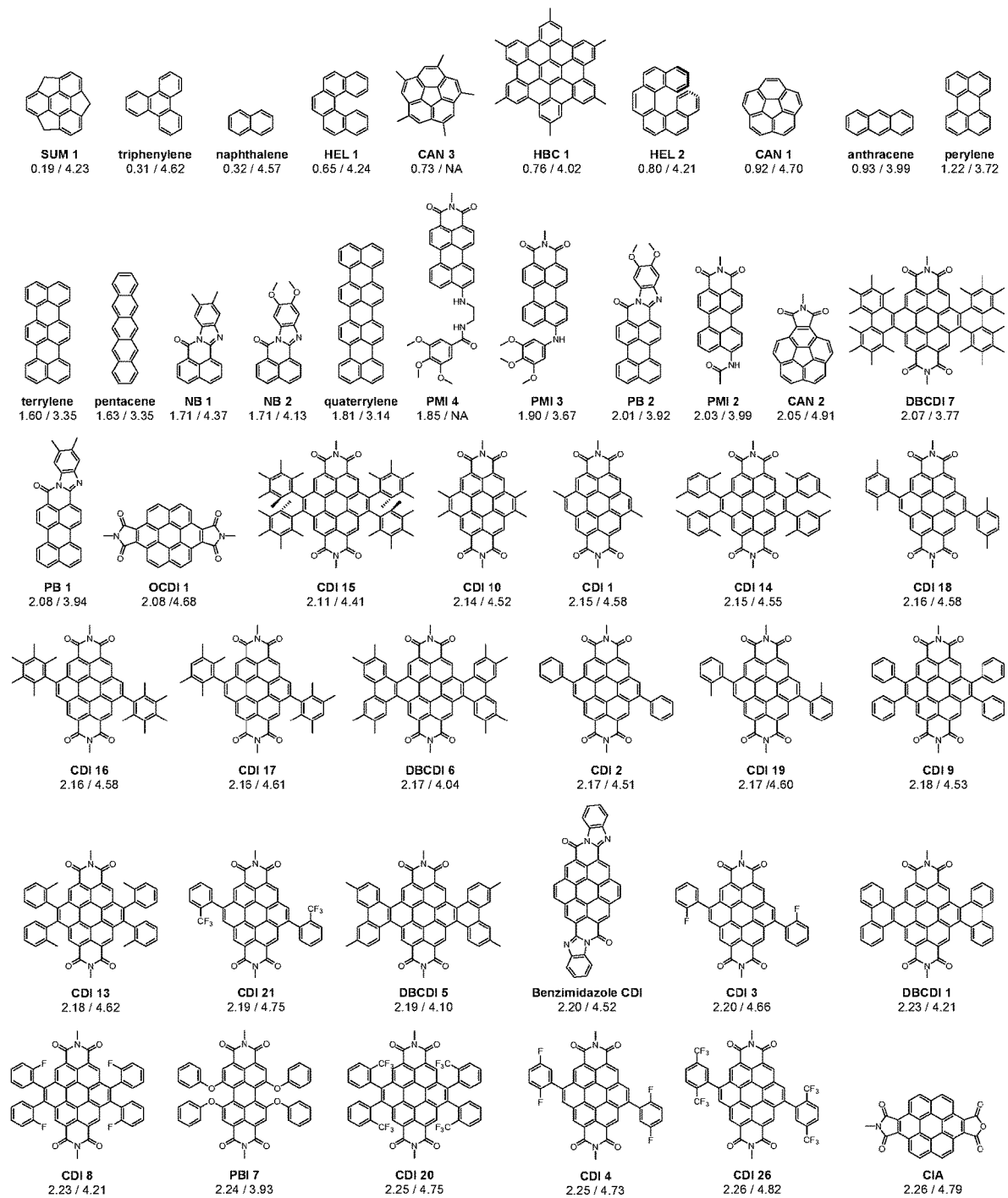
FIG. 15 shows molecular structures with electron affinity (E$_{ea}$) and ionization potential (E$_i$) calculated with the high-throughput computational model developed here and depicted below each structure (E$_{ea}$/E$_i$, vs. Li/Li$^+$). The structures are ordered from lowest to highest E$_{ea}$.
Figure 16:
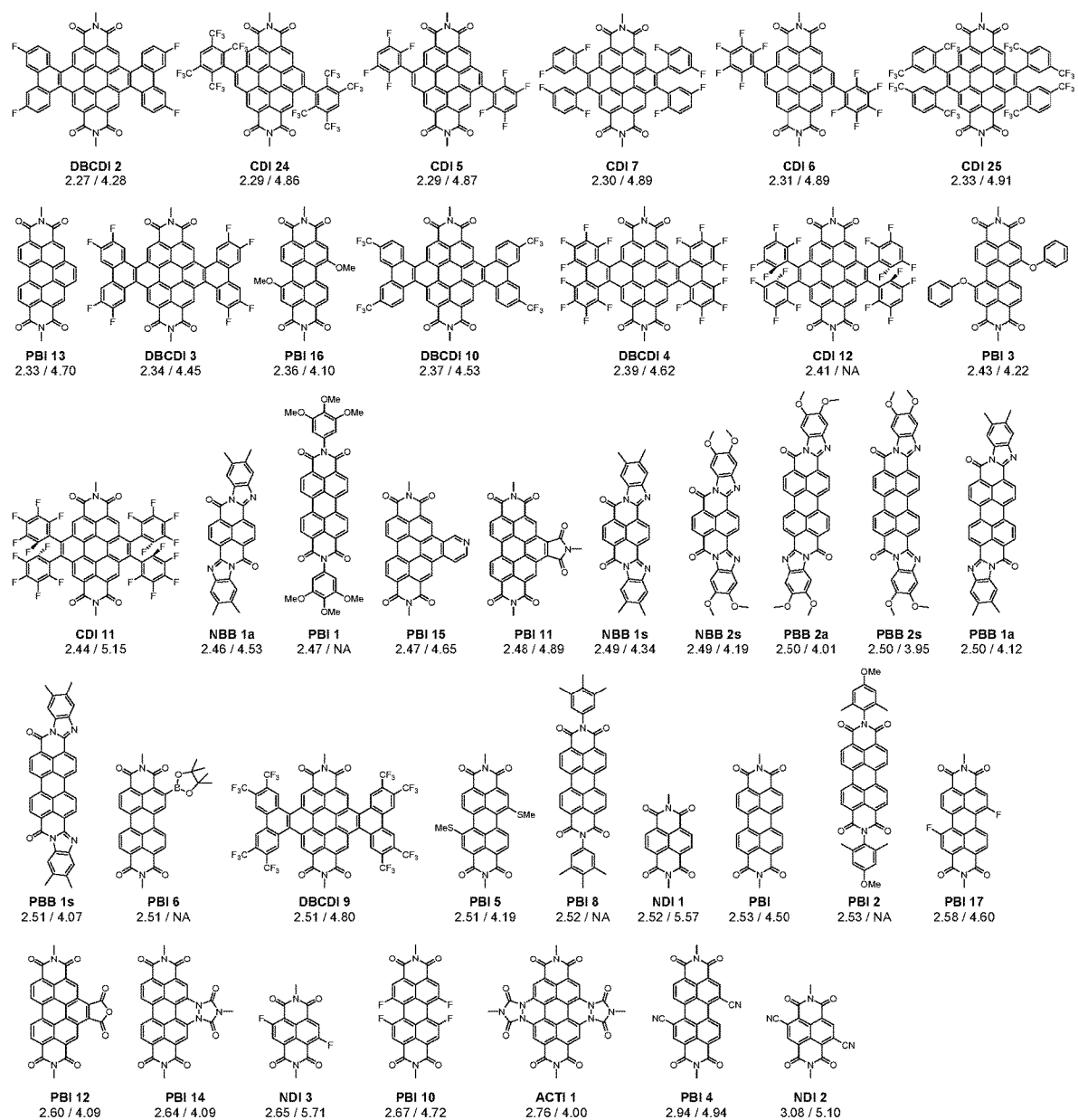
FIG. 16 shows molecular structures with electron affinity (E$_{ea}$) and ionization potential (E$_i$) calculated with the high-throughput computational model developed here and depicted below each structure (E$_{ea}$/E$_i$, vs. Li/Li$^+$). The structures are ordered from lowest to highest E$_{ea}$.
Figure 20:
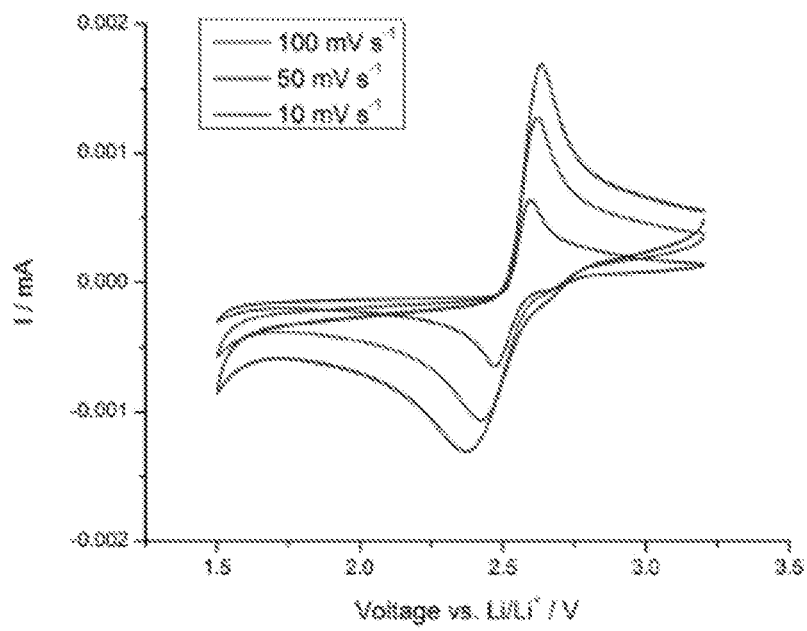
FIG. 20 shows cyclic voltammograms of PBI 1 at various scan rates.
Figure 21:
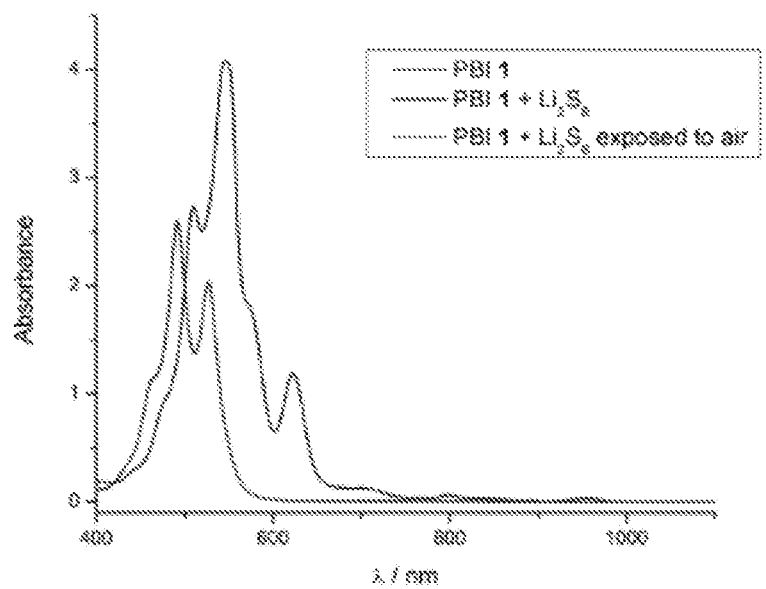
FIG. 21 shows UV-visible-NIR spectra of PBI 1 (red), PBI 1+Li$_2$S$_8$ (purple), and PBI 1+Li$_2$S$_8$ after exposure to air (teal). The spectra from PBI 1 (red) and PBI 1+Li$_2$S$_8$ after exposure to air (teal) perfectly overlap indicating the chemical reduction and subsequent oxidation are highly reversible.
Figure 22:
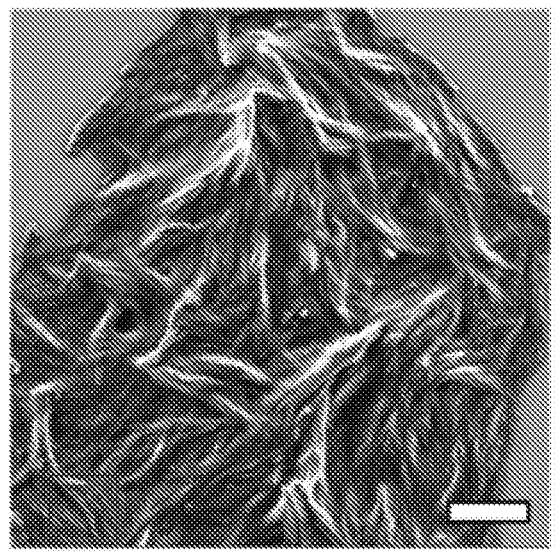
FIG. 22 shows fibrous nanostructured networks of a PBI 1+Li$_2$S$_8$ xerogel imaged with SEM. The scale bar is 2 μm and the blue box highlights the region depicted in FIG. 23.
Figure 23:
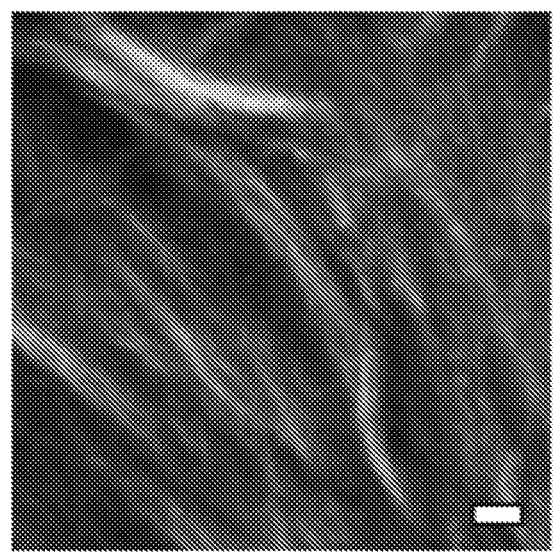
FIG. 23 shows fibrous nanostructured networks of a PBI 1+Li$_2$S$_8$ xerogel imaged with SEM. The scale bar is 200 nm. Fibers with ~20 nm diameter are resolved.
Figure 24:
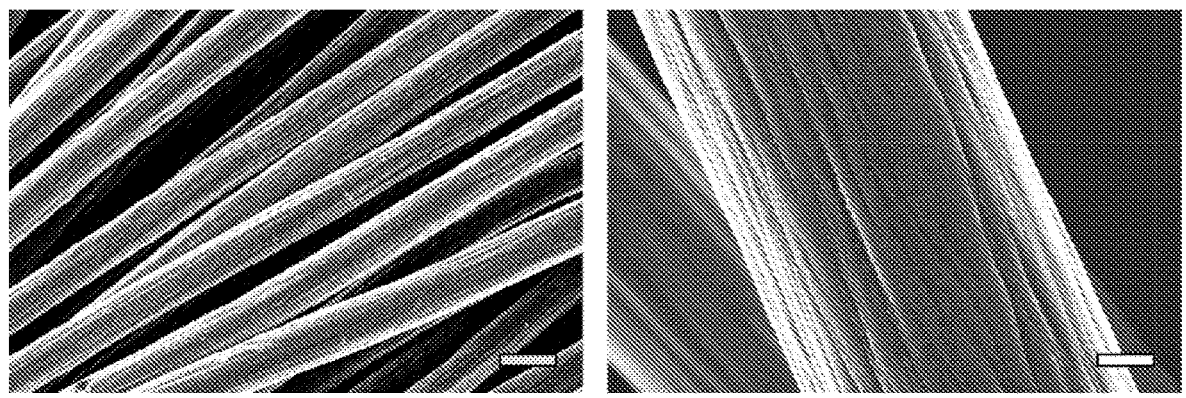
FIG. 24 shows SEM images of C felt from a battery with benzo[ghi]peryleneimide (BPI), but with no polysulfide, washed with the same procedure used to image Li$_2$S at different states of charge. This indicates that the deposits observed in the presence of Li$_2$S$_8$ are due to sulfur-based species, not electrolyte or BPI. Scale bar (left)=10 μm. Scale bar (right)=2 μm.
Figure 25:
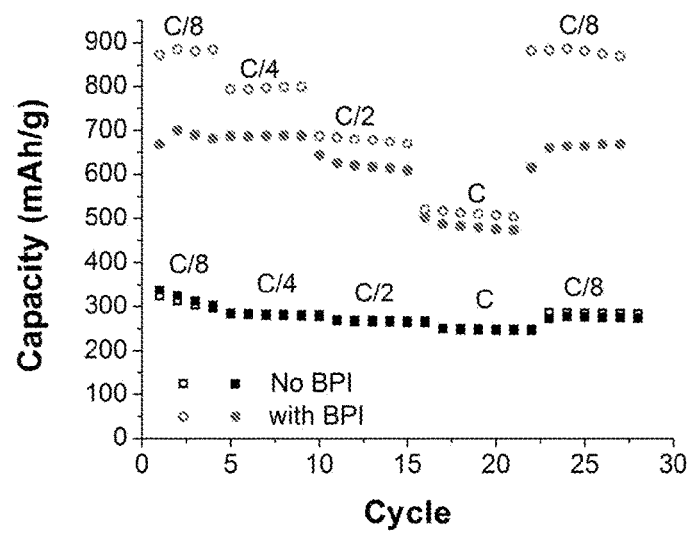
FIG. 25 shows charge (open) and discharge (filled) capacities for batteries cycling at various rates using BPI.
Figure 26:
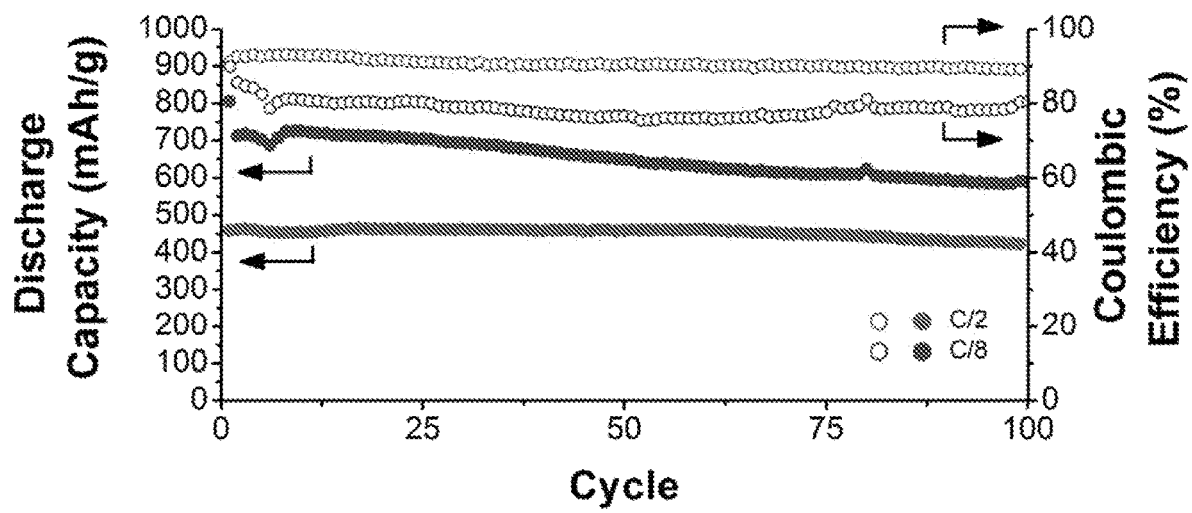
FIG. 26 shows discharge capacity (solid circles) and Coulombic efficiency (open circles) over 100 cycles of a battery with BPI.
Figure 27:
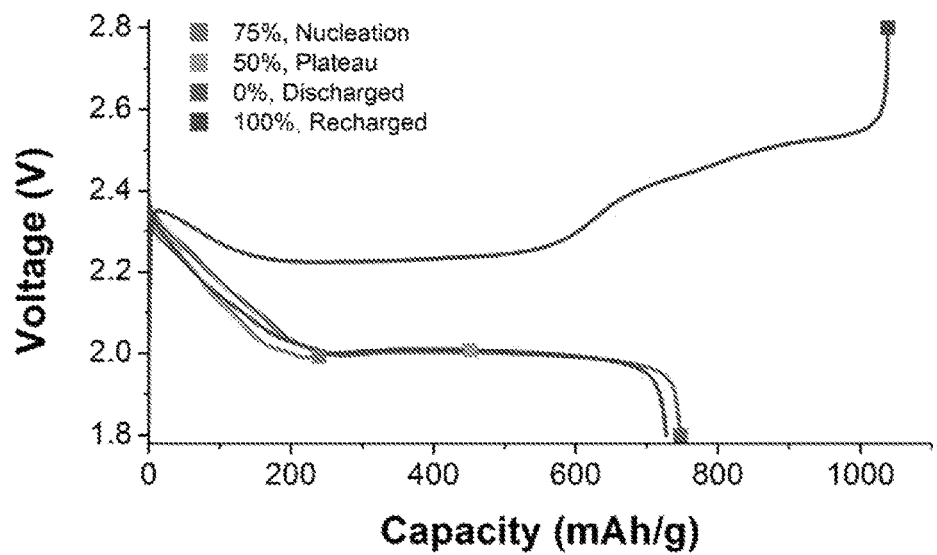
FIG. 27 shows points at which batteries with BPI were stopped to image the Li$_2$S deposition on the C felt.
Figure 28:
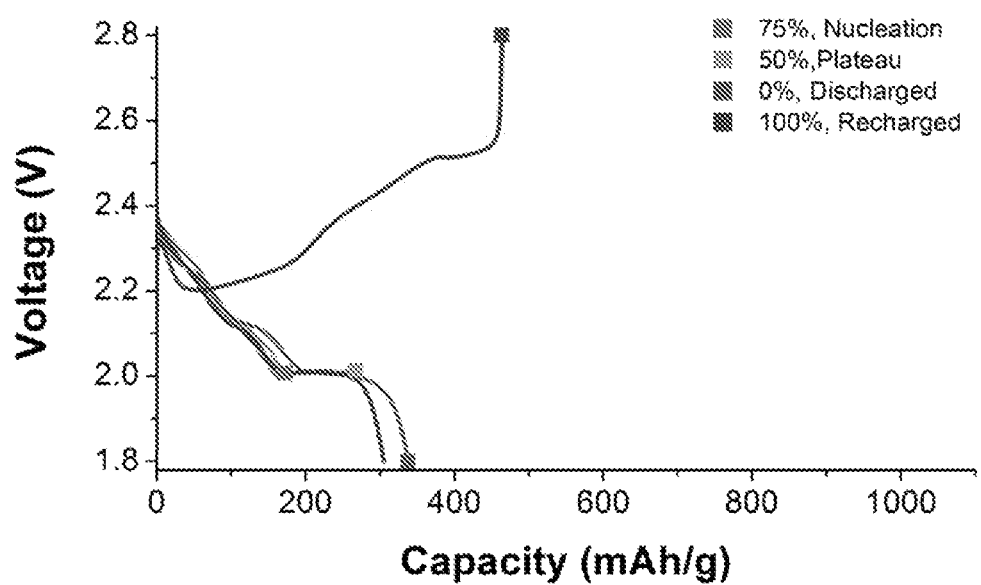
FIG. 28 shows points at which batteries that do not contain BPI were stopped to image the Li$_2$S deposition on the C felt.
Figure 30:
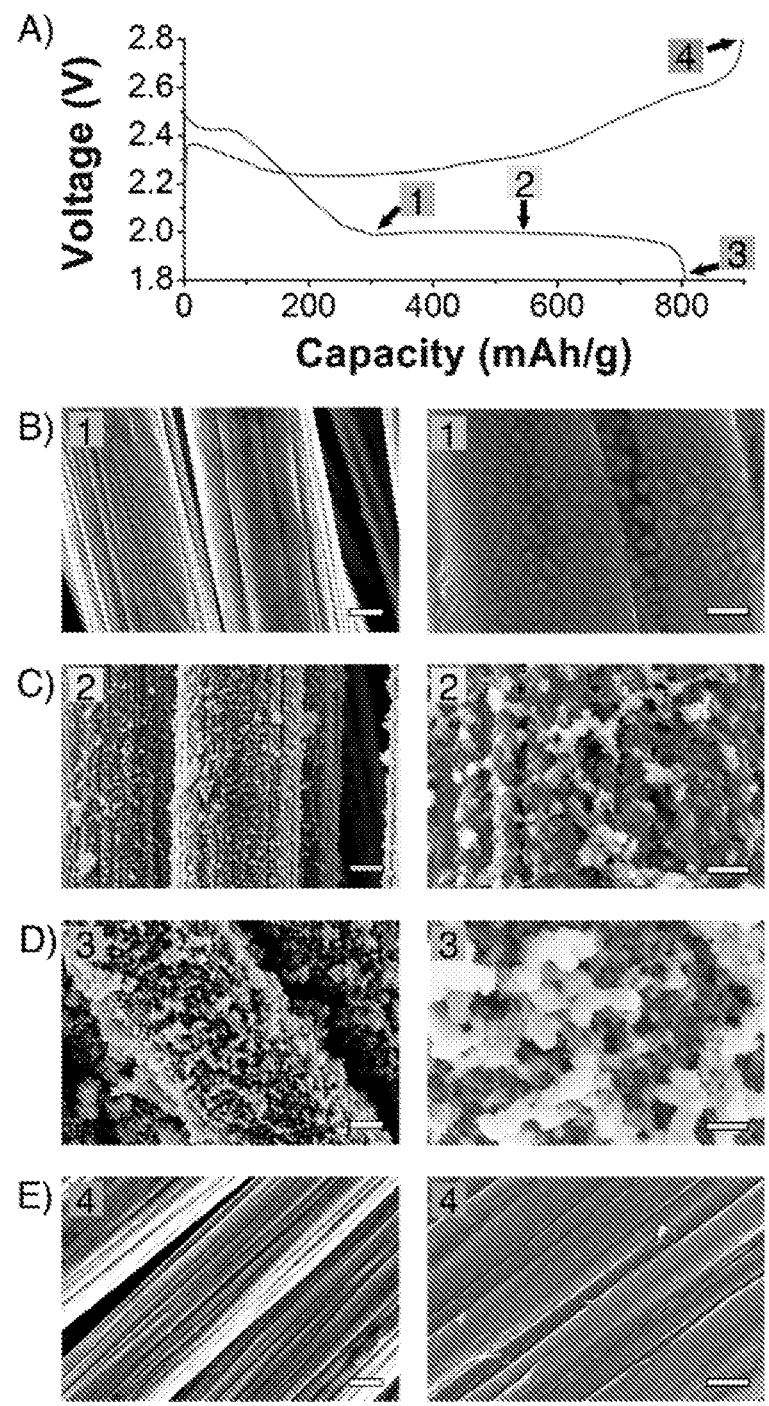
FIGS. 30A, B, C, D, and E show deposition of Li$_2$S on C cloth, imaged at different states-of-charge in Li—S cells with BPI redox mediator (first cycle at C/8 rate) A) Representative discharge/charge curve and the states-of-charge indicated at which separate cells were stopped to image the Li$_2$S deposition on C cloth. B) SEM images of Li$_2$S on C cloth at the nucleation point, 1. C) SEM images of $Li_2S$ on C cloth during the $Li_2S$ deposition plateau, 2. D) SEM images of $Li_2S$ on C cloth at the end of discharge, 3. E) SEM images of C cloth after recharge, 4. Scale bar (left images)=2 µm. Scale bar (right images)=500 nm.
Figure 31:
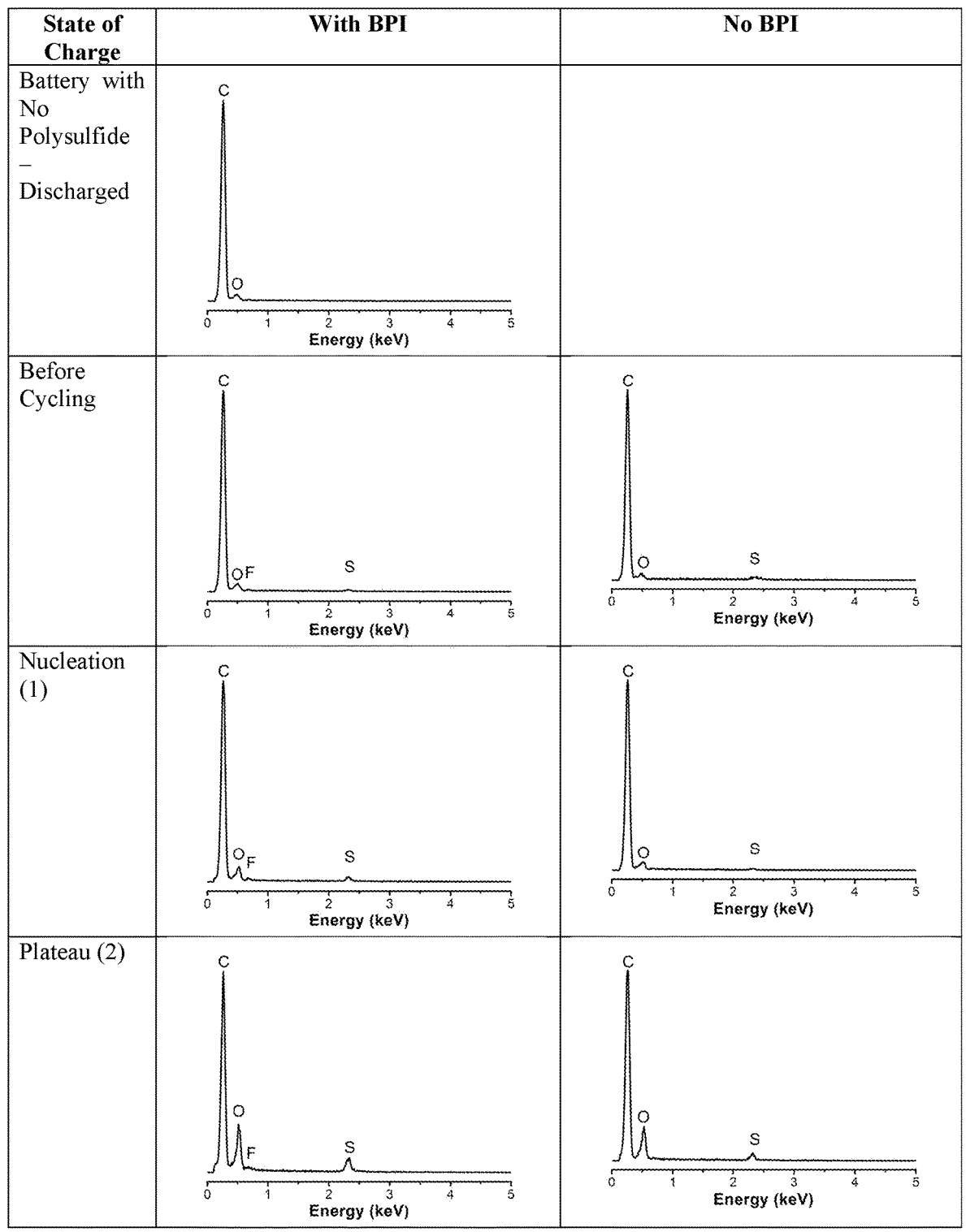
FIG. 31 shows EDX spectra of washed C felt at various states of charge with and without BPI.
Figure 31:
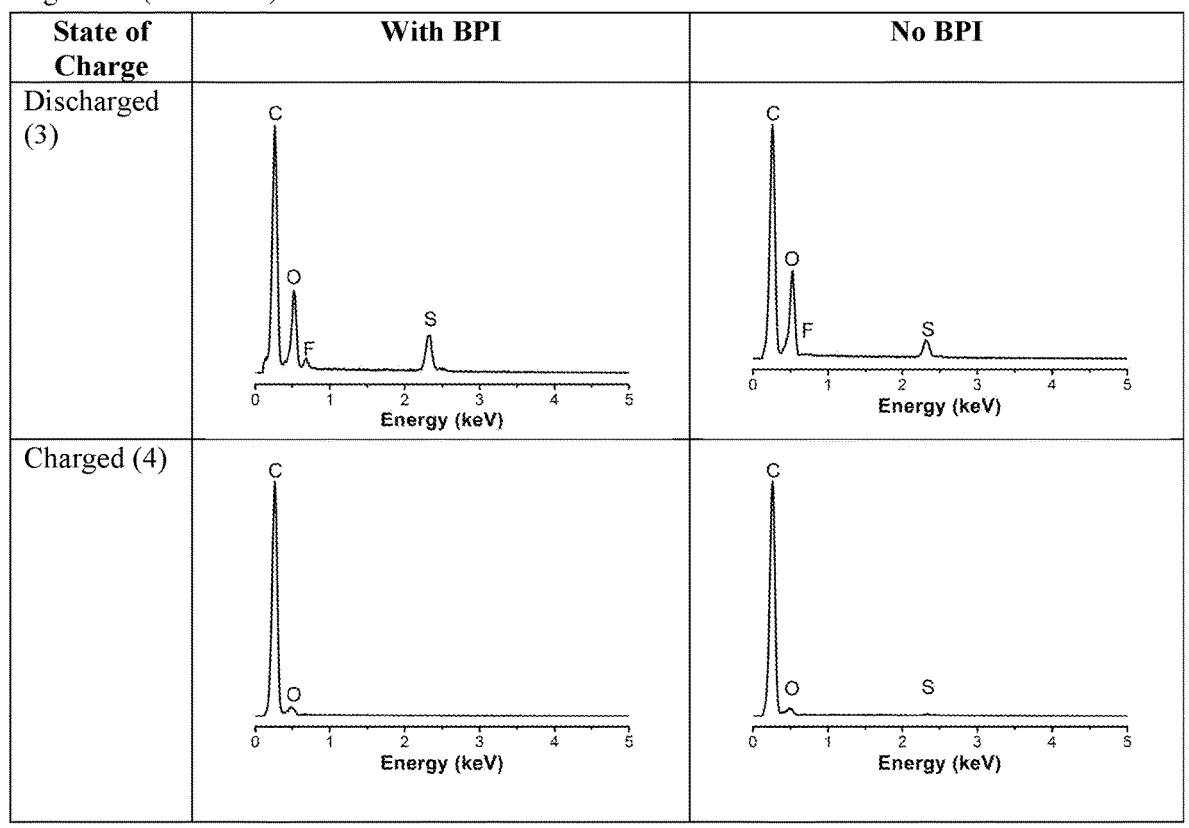
Figure 32:
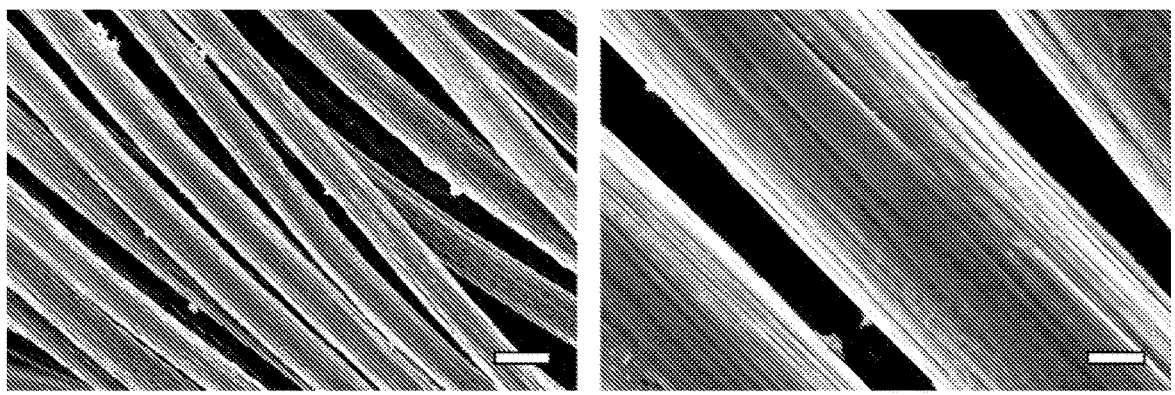
FIG. 32 shows SEM images of C felt containing BPI after exposure to polysulfides and washed by the standard procedure.
Figure 33:
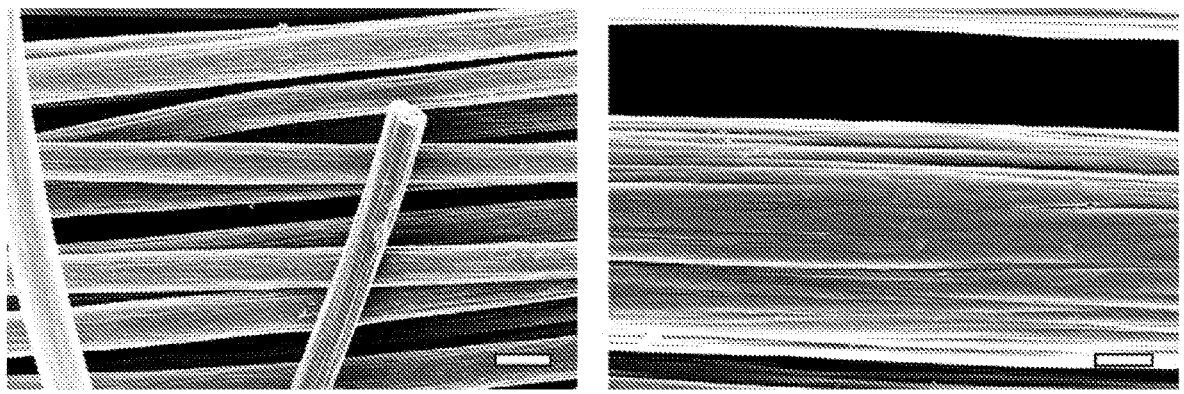
FIG. 33 shows SEM images of C felt with no BPI after exposure to polysulfides and washed by the standard procedure.
Figure 34:
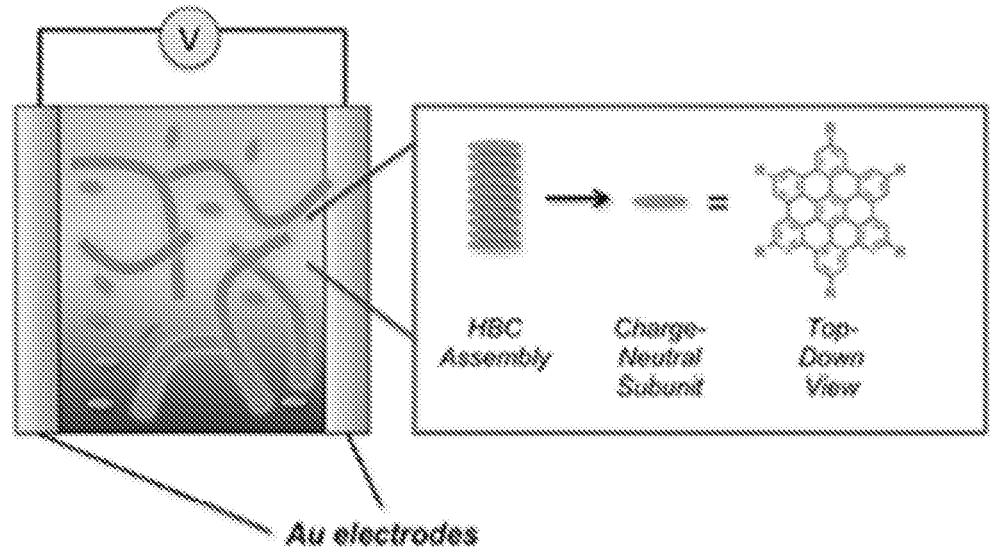

The total Wh discharged on the second cycle from the representative PBI 1+Li$_2$S$_8$ cell depicted in FIG. 8 was 0.829 mWh. The total catholyte mass was 20.4 mg. With a measured catholyte density of 1.12 g mL$^{-1}$ there was 0.0182 mL of catholyte. Taking into account the total Coulombs discharged (1.32 C measured, 2.09 C theoretical maximum) and assuming 100% excess lithium is necessary in a commercial cell the total Coulombs of lithium metal must be 4.18 C. From the Faraday constant (F) and the density of lithium as $\rho_{Li}$=0.534 g mL$^{-1}$ there must be 4.18 C/F×1 mol$_{Li}$/1 mol$_{e^-}$×6.94 g mol$^{-1}$$_{Li}$/0.534 g mL$^{-1}$=0.000563 mL of lithium metal. The total volume of catholyte and metal anode for a theoretical cell based on these metrics is then 0.0188 mL. The volumetric energy density is 0.829 mWh/0.0188 mL=44 Wh L$^{-1}$.

Analysis of Battery Discharge Capacities.

A minimum of 21 cells were cycled for each catholyte and the second discharge capacities were recorded (Table S2). The collection of discharge capacities was subjected to Chauvenet's criterion to identify and reject outliers. One outlier was identified and removed from each dataset for the final statistics reported in the manuscript (Tables S3).

Variable Concentration Study and Determination of $K_\alpha$ for PBI 1. Solutions of PBI 1 in electrolyte (TEGDME, 0.5 mol LiTFSI) were prepared between 1.5×10$^{-3}$ mol L$^{-1}$ and 4.9×10$^{-7}$ mol and UV-visible spectra were obtained. The extinction coefficient at 555 nm was determined for each spectrum, and the data set normalized. The isodesmic model for self-assembly was then used to fit the data. Origin 8.5 (OriginLab, Northampton, Mass.) was used to fit the equation $$\alpha = 1 - \frac{2K_aC + 1 - \sqrt{4K_aC + 1}}{2K_a^2C^2},$$

where α is the mole fraction of aggregated molecules, $K_\alpha$ is the association constant, and C is concentration. A $K_\alpha$ of $6.1 \pm 0.3 \times 10^4$ L mol$^{-1}$ was determined.

Reversible Reduction of PBI 1 by $Li_2S_8$.

In an Ar-filled glove box, a stock solution of PBI 1 (10 mL, $1.0 \times 10^{-3}$ mol L$^{-1}$) in TEGDME containing 0.50 mol L$^{-1}$ LiTFSI was prepared. A portion of this stock solution (3 mL) was diluted with an additional portion of electrolyte to a final concentration of $5.4 \times 10^{-5}$ mol L$^{-1}$. Separately, a sample of reduced PBI 1 was prepared by mixing a portion of the PBI 1 stock solution (3.0 mL) with a $Li_2S_8$ solution (0.60 mL, $8.0 \times 10^{-3}$ mol S L$^{-1}$ in electrolyte) and an additional portion of electrolyte (2 mL), giving a final concentration $5.4 \times 10^{-5}$ mol L$^{-1}$ PBI 1 and $3.2 \times 10^{-4}$ mol S L$^{-1}$. UV-visible-NIR spectra were obtained in sealed cuvettes. The reduced PBI 1 was then exposed to air, the cuvette shaken for 2 min and another spectrum was obtained. After exposure to air, the spectrum overlays with the PBI 1 sample indicating that PBI 1 can be reversibly reduced by $Li_2S_8$.

SEM Sample Preparation.

Electron microscopy of the actual catholyte gel was not feasible due to the disproportionately high concentration of salt (LiTFSI and LiNO$_3$) and lithium polysulfide relative to network forming PBI 1. To prepare samples that were both representative of the supramolecular gel network catholyte and amendable to SEM imaging, samples with lower salt and lithium polysulfide concentration were prepared. A 0.25 mol S L$^{-1}$ solution (nominal $Li_2S_8$ composition) was prepared by diluting ten-fold a 2.5 mol S L$^{-1}$ in TEGDME electrolyte (0.50 mol L$^{-1}$ LiTFSI and 0.15 mol L$^{-1}$ LiNO$_3$) with pure TEGDME. The 0.25 mol S L$^{-1}$ solution (40 µL) was then mixed with a 0.070 mol L$^{-1}$ solution of PBI 1 dissolved in pure TEGDME (43 µL). The mixture was dropcast onto a polished silicon wafer and dried under reduced pressure at room temperature for 48 h prior to analysis.

Images were acquired with a secondary electron detector, a 2 keV beam energy, and a 3.7 mm working distance.

Example 4. Preparation of Redox Mediator BPI

The preparation of BPI is provided below.

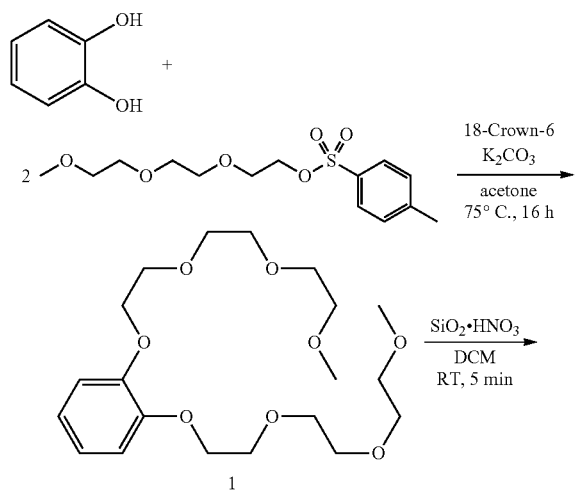

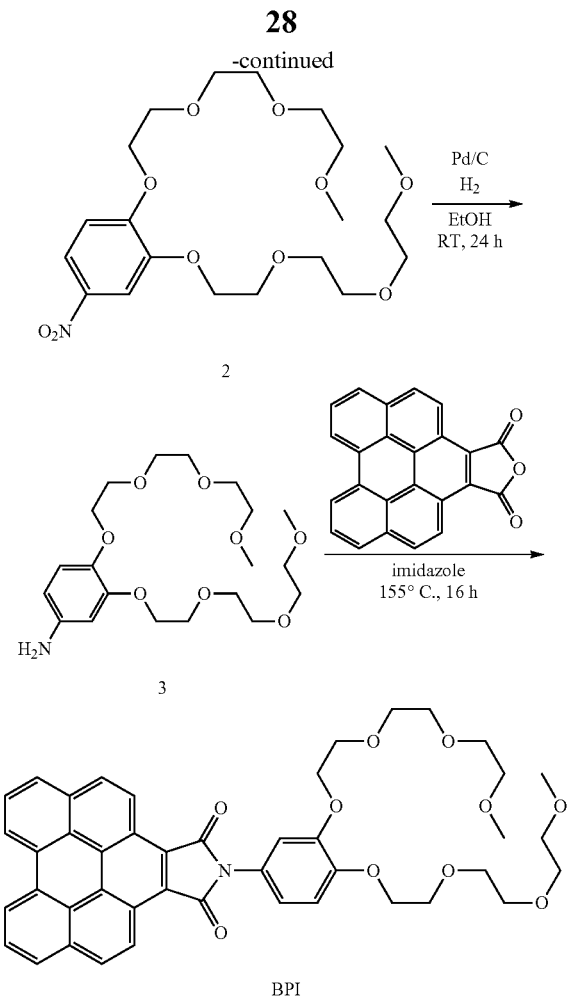

Synthesis of 1

Catechol (7.96 g, 72 mmol), tri(ethylene glycol) monomethyl ether tosylate (46 g, 144 mmol), K$_2$CO$_3$ (33 g, 239 mmol), 18-Crown-6 (3.75 g, 14 mmol), and acetone (200 mL) were added to an oven-dried 500 mL 3-necked flask. The reaction mixture was sparged with N$_2$ for 30 m, fitted with a reflux condenser, and refluxed (75° C.) for 16 h. The solvent was removed under reduced pressure. Dichloromethane was added, and the solution was washed with 50 mL saturated NaHCO$_3$, 2×50 mL H$_2$O, dried over MgSO$_4$, and filtered. The volatiles were removed in vacuo to isolate 26.71 g (92%) of a colorless oil. Spectra are consistent with those previously published.

Synthesis of 2

Compound 1 (8.4 g, 20.87 mmol) and dichloromethane (50 mL) were added to a 150 mL round bottom flask. After 1 dissolved, 20% HNO$_3$.SiO$_2$ (16.95 g) was added, and the suspension was stirred for 5 min. The suspension was filtered through a pad of Celite on a fritted filter, and solvent was then removed from the filtrate under reduced pressure. The mixture was purified by column chromatography with DCM/MeOH as the eluent (SiO$_2$, 0-8% MeOH). Column fractions containing pure and impure product were combined and solvent was removed under reduced pressure. The resulting mixture was purified again by column chromatography with 50:50 DCM:EtOAc as eluent to yield a dark orange oil (5.06 g, 54%). $^1$H NMR (CDCl$_3$) δ7.84 (dd, 1H, J$_{HH}$=9, 3 Hz, ArH), 7.76 (d, 1H, J$_{HH}$=3 Hz, ArH), 6.92 (d, 1H, J$_{HH}$=9 Hz, ArH), 4.22 (m, 4H, OCH$_2$), 3.87 (m, 4H, OCH$_2$), 3.71 (m, 4H, OCH$_2$), 3.65-3.61 (overlapping m, 8H, OCH$_2$), 3.51 (m, 4H, OCH$_2$), 3.34 (s, 6H, OCH$_3$); $^{13}\{^1H\}$ δ154.5, 148.6, 141.5, 118.1, 112.0, 109.1, 71.99 (2C), 71.02 (2C), 70.76, 70.75, 70.64, 70.62, 69.6, 69.5, 69.2, 69.1, 59.1 (2C); UV/vis (CHCl$_3$): λ$_{max}$/nm (ε/M$^{-1}$ cm$^{-1}$): 305 (5954), 338 (7291); Anal Calc'd for C$_{20}$H$_{33}$NO$_{10}$: C, 53.68; H, 7.43; N, 3.13; Found: C, 53.46, H, 7.30; N, 3.19; ESI-MS (MeOH) m/z=470.20 [M +Na]$^+$.

Synthesis of 3

Compound 2 (2.67 g, 5.97 mmol) and ethanol (120 mL) were added to a 250 mL flask. The flask was evacuated and refilled with N$_2$ three times before adding 10% by weight Pd/C (313. 21 mg, 0.294 mmol Pd) as a dispersion in EtOH. The flask was fitted with a 3-way valve connected to a H$_2$-filled balloon. The suspension was evacuated and refilled with H$_2$ three times and then allowed to stir under an H$_2$ atmosphere for 24 h. The reaction mixture was filtered through a glass frit containing a pad of Celite and the filtrate was concentrated under reduced pressure to yield a brown oil (1.98 g, 80%). $^1$H NMR (CDCl$_3$) δ6.77 (d, 1H, J$_{HH}$=9 Hz, ArH), 6.33 (d, 1H, J$_{HH}$=3 Hz, ArH), 6.22 (dd, 1H, J$_{HH}$=9 Hz, 3 Hz, ArH), 4.12 (t, 2H, J$_{HH}$=5 Hz, OCH$_2$), 4.08 (t, 2H, J$_{HH}$=5 Hz, OCH$_2$), 3.84 (t, 2H, J$_{HH}$=5 Hz, OCH$_2$), 3.79 (t, 2H, J$_{HH}$=5 Hz, OCH$_2$), 3.74-3.71 (overlapping m, 4H, OCH$_2$), 3.68-3.64 (overlapping m, 8H, OCH$_2$), 3.56-3.54 (overlapping m, 4H, OCH$_2$), 3.38 (s, 6H, OCH$_3$), 2.00 (br s, NH$_2$); $^{13}$C$\{^1H\}$ δ150.4, 142.0, 141.6, 118.4, 107.6, 103.4, 72.0 (2C), 70.9, 70.78 (2C), 70.77, 70.6 (2C), 70.4, 70.1, 69.8, 68.7, 59.14, 59.12; UV/vis (CHCl$_3$): λ$_{max}$/nm (ε/L mol$^{-1}$ cm$^{-1}$): 298 (7704); Anal Calc'd for C$_{20}$H$_{35}$NO$_8$: C, 57.54; H, 8.45; N, 3.35; Found: C, 57.03; H, 8.36; N, 3.33; ESI-MS (MeOH) m/z=440.20 [M +Na]$^+$.

Synthesis of BPI

Compound 3 (0.993 g 2.379 mmol), benzoperylene anhydride (0.641 g, 1.840 mmol), imidazole (6.3 g, 92.1 mmol), and a stir bar were added to a 40 mL septum-capped vial. The vial was evacuated and refilled with N$_2$ three times, and stirred at 155° C. for 16 h over which time the orange suspension becomes a brown solution. The vial was removed from heat and 30 mL CHCl$_3$ was added before the imidazole solidified. The solution was washed with 3×30 mL 1M HCl, dried over MgSO$_4$, filtered, and concentrated under reduced pressure. The crude product was purified with a SiO$_2$ plug. Perylene (yellow with blue fluorescence) was eluted first with DCM. The orange product was eluted with 5% MeOH in DCM. The solvent was removed under reduced pressure to isolate 1.159 g (84%) of a dark orange solid. $^1$H NMR (CDCl$_3$) δ8.12 (d, 2H, J$_{HH}$=8 Hz, ArH), 7.99 (d, 2H, J$_{HH}$=8 Hz, ArH), 7.57 (t, 2H, J$_{HH}$=8 Hz, ArH), 7.52 (d, 2H, J$_{HH}$=8 Hz, ArH), 7.22-7.17 (overlapping m, 5H, ArH), 4.35 (t, 4H, J$_{HH}$=5 Hz, OCH$_2$), 3.99 (q, 4H, J$_{HH}$=5 Hz, OCH$_2$), 3.86 (m, 4H, OCH$_2$), 3.79 (m, 4H, OCH$_2$), 3.74 (m, 4H, OCH$_2$), 3.70 (m, 4H, OCH$_2$), 3.64 (m, 4H, OCH$_2$), 3.58 (m, 4H, OCH$_2$), 3.45 (s, 3H, OCH$_3$), 3.38 (s, 3H, OCH$_3$); $^{13}$C $\{^1H\}$ NMR (CDCl$_3$) δ186.1, 149.4, 148.5, 131.0, 129.2, 128.7, 127.0, 126.9, 125.7, 125.1, 122.7, 122.7, 121.6, 121.5, 121.0, 119.7, 114.9, 113.4, 72.21, 72.16, 71.15, 71.11, 70.98, 70.96, 70.84, 70.78, 70.01, 69.95, 69.4, 69.3, 59.3, 59.2; UV/vis (CHCl$_3$): λ$_{max}$/nm (ε/L mol$^{-1}$ cm$^{-1}$): 330 (32257), 342 (56880), 368 (18725), 391 (17815), 459 (4881), 485 (6760); Anal Calc'd for C$_{44}$H$_{43}$NO$_{10}$: C, 70.86; H, 5.81, N, 1.88; Found: C, 70.62; H, 6.09; N, 2.09; MS (MALDI-TOF, DCTB) m/z=784.0837 [M+K]$^+$, 768.1177 [M+Na]$^+$.

Example 5. Preparation of Battery with BPI

Electrochemistry. The electrochemical cell was configured with a glassy carbon working electrode and lithium metal reference and counter electrodes. Working solutions for cyclic voltammetry (CV) were separated from lithium counter and reference electrodes with a glass frit with an average pore size of ~7 nm and thickness of 5 mm obtained from Advanced Glass and Ceramics (St. James, N.C., USA). In order to account for the potential drop across a highly resistive frit, all CV measurements were corrected for iR drop by measuring the impedance between the working and reference electrodes with an applied AC voltage with frequency of 100 MHz and correcting for 85% of the expected iR drop. CVs of polysulfide alone, BPI alone, and BPI with polysulfide were conducted in electrolyte with 2.5 mM BPI and 0.012 mM sulfur of nominal composition Li$_2$S$_8$ at 1 mV/s.

Battery Assembly.

Lithium disks (⅜ inch diameter) were punched from 1.5 mm thick Li foil and soaked in electrolyte for >1 h. One side of the Li disk was scraped with a spatula to expose a shiny Li surface. The scraped side was pressed onto a nickel electrode, 6 μL electrolyte and a piece of Celgard (½ inch diameter) were placed on top. Two pieces of C felt (with of without BPI) were placed in the well (0.5 mm deep, ¼ inch diameter) of a gold-coated nickel electrode. About 18 μL catholyte (1.0 M sulfur as Li$_2$S$_8$ in electrolyte, d=1.05 g/mL) was added to the well with the C felt (16-22 mg weight of catholyte), the weight was recorded, and the battery assembled.

Control Batteries without Sulfur.

In order to test if the BPI is contributing to the observed battery capacities, batteries were prepared with BPI, but no sulfur species. Batteries were assembled as above, using C felt containing BPI, but rather than polysulfide solution, 18 μL of electrolyte was used to fill the well in the electrode. The batteries were cycled at similar current densities to batteries with polysulfide (the electrolyte was weighed, and a C/8 current density was calculated as if 1.0 M sulfur as Li$_2$S$_8$ in electrolyte had been added). Of three batteries run, the greatest charge observed due to BPI was 3.72×10$^{-3}$ mAh. The batteries with BPI and 1.0 M sulfur average 0.42 mAh. The charging of BPI contributes at maximum 0.9% of the total capacity of the battery.

SEM of Li$_2$S at Various States-of-Charge (SOC).

Batteries were assembled as described above, both with and without BPI. They were cycled at C/8. Batteries were stopped at different states of discharge: (1) before cycling, SOC=100% (2) at nucleation of Li$_2$S, SOC=75%, (3) during the plateau, SOC=50%, (4) discharged, SOC=0%, and (5) recharged, SOC=100%

After the batteries were stopped, they were immediately disassembled inside the glove box. The top of the two carbon felt pieces was removed and washed with 5×0.5 mL CHCl$_3$, and dried under vacuum for 5 min. The samples were affixed to the stage for the SEM inside the glove box, brought to the SEM in a sealed jar, and transferred to the microscope sample chamber with <5 s exposure to air.

Images of C Felt Before Battery Cycling.

Two C felt disks (with or without BPI) were placed in an electrode well. 18 µL catholyte (1.0 M sulfur as Li$_2$S$_8$ in electrolyte) was added and the mixture was allowed to sit for 10 min. The C felt disks were then removed and washed with the same procedure as described above.

Example 6. Potentiostatic Electrodeposition Experiments

Procedure.

Cells were initially held at 2.09 V for up to 9 h, or until current fell below 6 µA, to minimize the amount of higher-order polysulfides in the solution. The cells were then held at 1.95V or 2.0V to initiate nucleation and growth of Li$_2$S.

Model of Electrodeposition.

In this work, electrodeposition is modeled as being on a planar surface, which we believe is a reasonable assumption considering that deposited layers are thin compared to the diameter of the carbon fibers. Furthermore, in a previous work we have shown that electrodeposition kinetics are limited by surface reaction rate rather than diffusion, and that the deposited insulating sulfide forms a passivating film that progressively reduces the carbon surface area available for deposition, resulting in two-dimensional growth and a thin film-like morphology.

For potentiostatic electrodeposition under these conditions, the current density vs. time relation is of the form $$\frac{J}{J_m} = \left(\frac{t}{t_m}\right)\exp\left[-\frac{1}{2}\left(\frac{t^2}{t_m^2}-1\right)\right]$$

Where $J_m$ and $t_m$ are respectively the maximum current and the time at which the maximum current occurs. This equation follows from the Avrami equation, which accounts for the impingement of islands after growth. In particular, the exponential factor represents the probability (from the Poisson distribution) that a given area element of the electrode is untransformed and therefore available for further reaction. The width of the peak can be used to determine the growth rate constant k.

$$t_m = (2\pi N_0 k^2)^{-1/2}$$

where $N_0$ is the number of nuclei.

In the case of electrodeposition of Li$_2$S involving the redox mediator BPI, we model the additional current due to the mediator with the term c. We assume that the rate-limiting step is due to BPI. If this were not the case, a horizontal asymptote would be present in the current-time plot. The resulting current due to BPI is c times the available surface area of the electrode. Our modified current-time relation is:

$$\frac{J}{J_m} = \left(\frac{t}{t_m}+c\right)\exp\left[-\frac{1}{2}\left(\frac{t^2}{t_m^2}-1\right)\right]$$

Example 7. Preparation of Redox Mediator HBC 7

The preparation of HBC 7 is provided below.

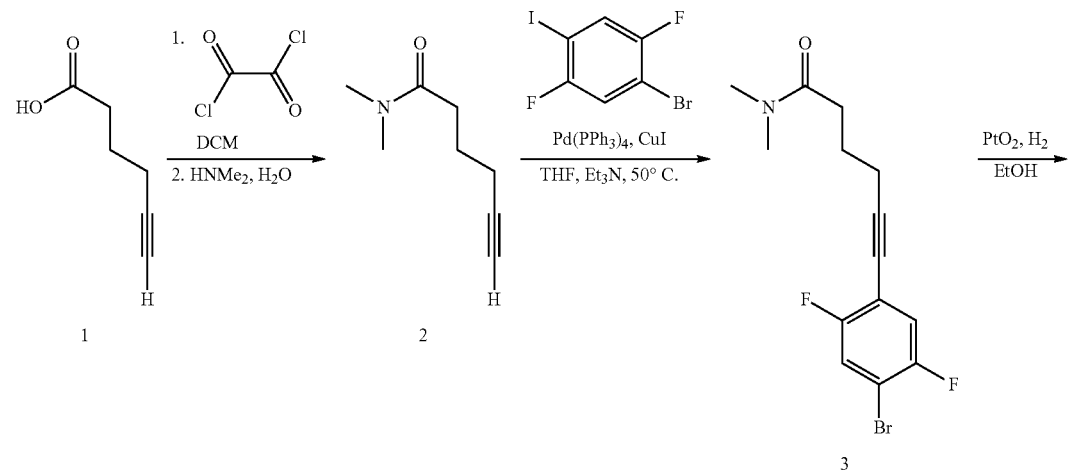

-continued

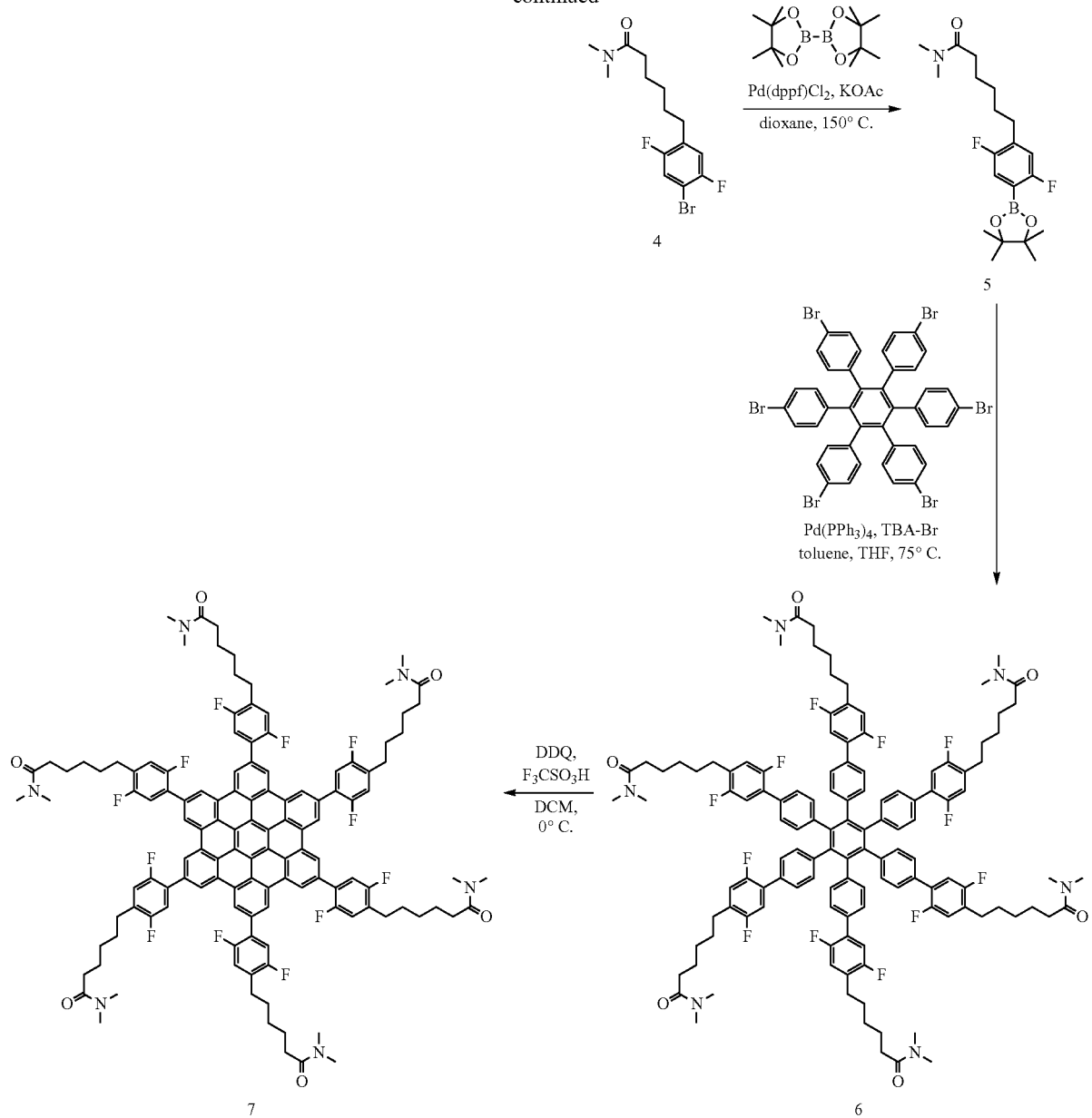

Synthesis of N,N-dimethylhex-5-ynamide (2)

A flame-dried 500 mL round bottom flask purged with nitrogen was charged with 5-hexynoic acid (15.1 g, 135 mmol) and anhydrous DCM (300 mL). A solution of oxalyl chloride (17.4 g, 137 mmol) in anhydrous DCM (45 mL) was added drop-wise over a period of 1.5 h. The resulting solution was stirred for 21 h under a nitrogen atmosphere and subsequently concentrated in vacuo. The crude product was slowly added (30 min) to a 150 mL Parr bottle containing an ice-cold stirred solution of dimethylamine in water (40% w/w, 95 mL). After addition of the first 2 mL, an ice bath was used to maintain a strict sub-ambient temperature. The bottle was sealed and stirring continued for 15 min, after which the ice bath was removed. After stirring for an additional 2 h at room temperature, the flask was cooled to 0° C. in the refrigerator before removing the seal. Excess dimethylamine was evaporated by bubbling nitrogen through the reaction mixture in a fume hood with adequate ventilation; aqueous 5 M NaOH solution (20 ml) was then added slowly. The product was extracted from the reaction mixture with DCM (3×200 mL). The combined organic layers were dried on $NaSO_4$ and concentrated in vacuo to give the product as a yellow oil (16.5 g, 118 mmol, 88%). $^1$H NMR ($CDCl_3$): δ3.03 (s, 3H), 2.95 (s, 3H), 2.46 (t, J=7.4 Hz, 2H), 2.29 (td, J=6.8 Hz, J=2.7 Hz, 2H), 1.97 (t, J=2.7 Hz, 1H), 1.87 (m, 2H); $^{13}$C NMR ($CDCl_3$): δ172.4, 84.1, 69.0, 37.3, 35.5, 31.8, 23.9, 18.1; FT-IR (neat): $\bar{v}$ 3291 (w), 3233 (w), 2940 (w), 2115 (w), 1636 (s), 1498 (m), 1456 (m), 1410 (m), 1399 (s), 1353 (w), 1335 (w), 1264 (m), 1217 (w), 1179 (w), 1141 (m), 1058 (w), 1045 (w), 1013 (w), 970 (w), 909 (w), 857 (w), 809 (w) cm$^{-1}$. ESI-MS (MeOH) m/z=162.09 [M+Na]$^+$. Anal Calc'd for $C_8H_{13}NO$: C, 69.03; H, 9.41; N, 10.06. Found: C, 68.79; H, 9.44; N, 10.23.

Synthesis of 3

Et$_3$N (250 mL) was added to a 1 L Schlenk flask and it was capped with a septum. The head-space was evacuated and refilled with N$_2$. N,N-dimethylhex-5-ynamide (7.23 g, 52 mmol) was added, followed by dry THF (250 mL). The solution was deoxygenated by bubbling N$_2$ through for 1 h. 1-bromo-2,5-difluoro-4-iodobenzene (15.0 g, 47 mmol), Pd(PPh$_3$)$_4$ (0.543 g, 0.47 mmol), and CuI (0.185 g, 0.97 mmol) were added as solids while the reaction mixture purged with nitrogen. The solution was heated to 50° C. for 18 h, over which time a white precipitate formed. The mixture was filtered and the solids were washed with toluene. The filtrate was washed with 3×50 mL water. The filtrate was concentrated and purified by column chromatography (SiO$_2$, 3:7 hexanes:EtOAc) to yield 13.4 g (89%) of a pale yellow solid. $^1$H NMR (CDCl$_3$) δ7.268 (dd, $^3J_{HF}$=8 Hz, $^4J_{HF}$=6 Hz, 1H, ArH), 7.124 (dd, $^3J_{HF}$=8 Hz, $^4J_{HF}$=6 Hz, 1H, ArH), 3.034 (s, 3H, CH$_3$), 2.960 (s, 3H, CH$_3$), 2.544 (t, $^3J_{HH}$=7 Hz, 2H, CH$_2$), 2.508 (t, $^3J_{HH}$=7 Hz, 2H, CH$_2$), 1.959 (quintet, $^3J_{HH}$=7 Hz, 2H, CH$_2$); $^{13}$C {$^1$H} NMR (CDCl$_3$) δ172.3 (s, C=O), 158.7 (dd, $^1J_{CF}$=249 Hz, $^4J_{CF}$=3 Hz, CO, 155.2 (dd, $^1J_{CF}$=243 Hz, $^4J_{CF}$=3 Hz, CF), 120.3 (dd, $^2J_{CF}$=25 Hz, $^3J_{CF}$=0.6 Hz, ArCH), 120.0 (dd, $^2J_{CF}$=25 Hz, $^3J_{CF}$=2 Hz, ArCH), 113.1 (dd, $^2J_{CF}$=18 Hz, $^3J_{CF}$=9 Hz, C$_{ipso}$), 108.8 (dd, $^2J_{CF}$=24 Hz, $^3J_{CF}$=9 Hz, C$_{ipso}$), 97.7 (d, $^3J_{CF}$=3.5 Hz, ArC≡C), 73.6 (d, $^4J_{CF}$=2.3 Hz, ArC≡C), 37.3, 35.6, 31.8, 23.8, 19.3 (aliphatic C); $^{19}$F NMR (CDCl$_3$) δ −114.39 (m), −115.9 (m). ESI-MS (MeOH) m/z=356.03 [M +Na]$^+$, 689.08 [2M +Na]$^+$. Anal Calc'd for C$_{14}$H$_{14}$BrF$_2$NO: C, 50.93; H, 4.27; N, 4.24. Found: C, 51.09; H, 4.35; N, 4.33.

Synthesis of 4

Compound 3 (1.38 g, 4.18 mmol), EtOH (50 mL), and PtO$_2$ (50 mg, 0.22 mmol) were added to a 100 mL flask. The solution was sparged with N$_2$ for 30 min. A 3-way valve connected to a balloon filled with hydrogen was attached. The head-space of the flask was evacuated and refilled three times with H$_2$. The reaction was stirred for 16 h under H$_2$ atmosphere after which time a $^1$H NMR spectrum of an aliquot showed complete conversion of 3. The reaction mixture was filtered over Celite, which was then washed with EtOH. The volatiles were removed in vacuo from the filtrate to yield 1.36 g (98%) as an orange oil. $^1$H NMR (CDCl$_3$) δ7.204 (dd, $^3J_{HF}$=9 Hz, $^4J_{HF}$=6 Hz, 1H, ArH), 6.950 (dd, $^3J_{HF}$=9 Hz, $^4J_{HF}$=6 Hz, 1H, ArH), 2.995 (s, 3H, CH$_3$), 2.943 (s, 3H, CH$_3$), 2.592 (t, $^3J_{HH}$=7.5 Hz, 2H, CH$_2$), 2.303 (t, $^3J_{HH}$=7.5 Hz, 2H, CH$_2$), 1.669 (quintet, $^3J_{HH}$=7.5 Hz, 2H, CH$_2$), 1.615 (quintet, $^3J_{HH}$=7.5 Hz, 2H, CH$_2$), 1.381 (quintet, $^3J_{HH}$=7.5 Hz, 2H, CH$_2$); $^{13}$C {$^1$H} NMR (CDCl$_3$) δ173.0 (s, C=O), 156.7 (dd, $^1J_{CF}$=244 Hz, $^4J_{CF}$=3 Hz, CF), 155.4 (dd, $^1J_{CF}$=242 Hz, $^4J_{CF}$=3 Hz, 130.7 (dd, $^2J_{CF}$=18.5 Hz, $^3J_{CF}$=6.5 Hz, C$_{ipso}$), 119.9 (d, $^2J_{CF}$=28 Hz, ArCH), 117.5 (dd, $^2J_{CF}$=24 Hz, $^3J_{CF}$=6 Hz, ArCH), 105.7 (dd, $^2J_{CF}$=23 Hz, $^3J_{CF}$=10 Hz, C$_{ipso}$), 37.4, 35.5, 33.2, 29.7, 29.0, 28.7, 24.9 (aliphatic C); $^{19}$F NMR (CDCl$_3$) δ −115.35 (m), −123.26 (m). ESI-MS (MeOH) m/z=352.00 [M+Na]$^+$, 681.01 [2M +Na]$^+$. Anal Calc'd for C$_{14}$H$_{18}$BrF$_2$NO: C, 50.31; H, 5.43; N, 4.19. Found: C, 50.33; H, 5.54; N, 4.33.

Synthesis of 5

Compound 4 (1.04 g, 3.12 mmol), bis(pinacolato)diboron (1.97 g, 7.76 mmol), Pd(dppf)Cl$_2$.DCM (0.130 g, 0.160 mmol), potassium acetate (2.62 g, 26.7 mmol), and dioxane (18 mL) were added to a septum-capped microwave flask. The reaction mixture was at 150° C. with microwave irradiation for 1 h. The reaction mixture was filtered, and the solids were washed with DCM. The volatiles were removed in vacuo from the combined filtrate. The mixture was purified by column chromatography (SiO$_2$, 0-50% of 100:5:1 DCM:MeOH:Et$_3$N in DCM) to yield 1.01 g (85%) of 5 as a yellow oil. $^1$H NMR (CDCl$_3$) δ7.322 (dd, $^3J_{HF}$=9.5 Hz, $^4J_{HF}$=4.5 Hz, 1H, ArH), 6.848 (dd, $^3J_{HF}$=9 Hz, $^4J_{HF}$=6 Hz, 1H, ArH), 2.993 (s, 3H, N(CH$_3$)$_2$), 2.940 (s, 3H, N(CH$_3$)$_2$), 2.642 (t, $^3J_{HH}$=7.5 Hz, 2H, CH$_2$), 2.296 (t, $^3J_{HH}$=7.5 Hz, 2H, CH$_2$), 1.663, 1.624 (overlapping quintets, $^3J_{HH}$=7.5 Hz, 4H, CH$_2$), 1.374 (quintet overlapping with next signal, $^3J_{HH}$=7.5 Hz, 2H, CH$_2$), 1.348 (s, 12H, BOCMe$_2$); $^{13}$C {$^1$H} NMR (CDCl$_3$) δ173.2 (C=O), 163.0 (dd, $^1J_{CF}$=245 Hz, $^4J_{CF}$=1.5 Hz, CF), 157.0 (dd, $^1J_{CF}$=240 Hz, $^4J_{CF}$=2 Hz, CF), 135.2 (dd, $^2J_{CF}$=19 Hz, $^3J_{CF}$=8.5 Hz, C$_{ipso}$), 122.1 (dd, $^2J_{CF}$=24 Hz, $^3J_{CF}$=9 Hz, ArCH), 117.1 (dd, $^2J_{CF}$=26.5 Hz, $^3J_{CF}$=5 Hz, ArCH), 84.12 (BOC$_2$Me$_4$), 37.5, 35.6, 33.4, 29.7, 29.2, 29.1, 25.04, 24.99 (NMe$_2$, CH$_2$, BO$_2$C$_2$Me$_4$). The C bonded to B could not be detected due to line broadening caused by the quadrupole moment of $^{11}$B (I=3/2)$^2$; $^{19}$F NMR (CDCl$_3$) δ −110.54 (m), −127.28 (m). ESI-MS (MeOH) m/z=404.20 [M +Na]$^+$, 785.43 [2M +Na]$^+$.

Synthesis of 6

Compound 5 (2.29 g, 6.00 mmol), hexakis(4-bromophenyl)benzene (0.667 g, 0.662 mmol), Pd(PPh$_3$)$_4$ (0.232 g, 0.201 mmol), and TBABr (0.153 g, 0.474 mmol) were added to 250 mL Schlenk flask. The flask was evacuated and refilled three times with N$_2$. Deoxygenated toluene (28 mL), THF (28 mL), and 1.0 M Na$_2$CO$_3$(aq) (24 mL) were added by syringe. The mixture was sparged with N$_2$ for 30 min, and then heated to 75° C. for 48 h. The organic and aqueous layers were separated and the organic washed with 3×50 mL water, dried over MgSO$_4$, filtered, and concentrated under reduced pressure. The mixture was purified by column chromatography (Biotage SNAP 100g KP-Sil, pure DCM to 95:5:1 DCM:MeOH:Et$_3$N over 12 column volumes. Fractions containing pure product and impure product were collected separately. To remove residual Pd, the mixtures were stirred with propylmercapto modified silica until the supernatant was colorless, then filtered, and extracted with 95:5 DCM:MeOH until the filtrate did not absorb UV light when spotted on a SiO$_2$ TLC plate. The impure product was subjected to column chromatography again with the same conditions (Biotage SNAP 50 g KP-Sil). The products from both columns were combined to yield 0.710 g (52% yield) as a white foam. $^1$H NMR (CDCl$_3$) δ7.094 (d, 2H, J$_{HH}$=8 Hz, ArH), 6.944 (d, 3H integrated with next signal, J$_{HH}$=8 Hz, ArH), 6.926 (dd, integrated with previous signal, J$_{HF}$=10 Hz, J$_{HH}$=7 Hz, ArH), 6.851 (dd, 1H, J$_{HF}$=11 Hz, J$_{HH}$=7 Hz, ArH), 2.982 (s, 3H, CO(CH$_3$)$_2$), 2.930 (s, 3H, CO(CH$_3$)$_2$), 2.584 (t, 2H, J$_{HH}$=8 Hz, CH$_2$), 2.291 (t, 2H, J$_{HH}$=8 Hz, CH$_2$), 1.654 (apparent quintet, 2H, J$_{HH}$=8 Hz, CH$_2$), 1.603 (apparent quintet, 2H, J$_{HH}$=8 Hz, CH$_2$), 1.373 (apparent quintet, 2H, J$_{HH}$=8 Hz, CH$_2$); $^{13}$C {$^1$H} NMR (CDCl$_3$) δ173.2 (C=O), 157.1 (dd, $^1J_{CF}$=240 Hz, $^4J_{CF}$=2 Hz, CF), 155.6 (dd, $^1J_{CF}$=240 Hz, $^4J_{CF}$=2 Hz, CF), 140.4, 140.2, 3 (d, J$_{CF}$=31 Hz), 132.1, 131.8, 129.8 (dd, J$_{CF}$=19 Hz, J$_{CF}$=8 Hz), 127.43, 127.40 (m), 117.5 (dd, J$_{CF}$=25 Hz, J$_{CF}$=6 Hz), 116.4 (dd, J$_{CF}$=26 Hz, J$_{CF}$=4 Hz), 37.5, 35.5, 33.4, 29.9, 29.2, 28.7, 25.0; MS (MALDI-TOF, DCTB) m/z=2053.90 [M]$^+$, 2075.85 [M+Na]$^+$; Anal Calc'd for $C_{126}H_{132}F_{12}N_6O_6$: C, 73.66; H, 6.48; N, 4.09. Found: C, 73.50; H, 6.67; N, 3.97.

Synthesis of 7

Compound 6 (0.499 g, 0.243 mmol) and DDQ (0.345 g, 1.52 mmol) were added to a 25 mL Schlenk flask, which was then evacuated and refilled three times with $N_2$. DCM (10 mL, dry, deoxygenated) was added, and the flask was cooled to 0° C. TfOH (0.25 mL, 2.8 mmol) was added dropwise and a brown precipitate formed on the sides of the flask. MALDI-TOF MS of an aliquot taken after 30 min showed residual unreacted 6. Additional portions of DDQ (0.172 g, 0.755 mmol) and TfOH (0.20 mL, 2.3 mmol) were added. MALDI-TOF MS of an aliquot taken after 30 m min of the second addition showed complete conversion of 6. To quench the reaction, saturated $NaHCO_3$(aq) (15 mL) was added slowly. The reaction mixture was then filtered, and the solids washed successively with $H_2O$, MeOH, and $CHCl_3$. The organic and aqueous phases were separated. The aqueous was extracted with 3×15 mL of $CHCl_3$. The combined organic phase was washed with 4×15 mL $H_2O$, dried with $MgSO_4$, filtered, and dried under reduced pressure. The compound was purified by Bio-bead (S—X1, $CHCl_3$) size exclusion chromatography. Fractions were analyzed by TLC ($SiO_2$, 95:5:1 DCM:MeOH:$Et_3N$) and only those containing pure 7 were combined to yield 126 mg (25%) as a yellow powder. The $^1H$ NMR spectrum is broad and $^{13}C$ NMR spectrum was unobtainable due to aggregation of 7. All peaks in the $^1H$ NMR spectrum are broad singlets and integration is unreliable. $^1H$ NMR ($3.8\times10^{-4}$M, $CDCl_3$): δ9.019, 8.598, 7.056, 3.195, 3.098, 3.026, 2.782, 2.586, 2.456, 1.831. UV/vis ($1.85\times10^{-5}$M, $CHCl_3$): $\lambda_{max}$/nm (ε/L mol$^{-1}$ cm$^{-1}$): 370 (169000), 416 (shoulder, 25900); MS (MALDI-TOF, DCTB) m/z=2040.55 [M]$^+$, 2063.59 [M+Na]$^+$; Anal Calc'd for $C_{126}H_{122}F_{12}N_6O_7$ (HBC.$H_2O$): C, 73.45; H, 5.97; N, 4.08. Found: C, 73.12; H, 5.70; N, 4.15.

DFT Calculations

Density functional theory (DFT) calculations were performed using the Q-Chem software package[3] with the B3LYP functional[4] and the cc-pVDZ basis set[5]. A polarizable continuum solvent model (dielectric constant 9) was applied.

Titration of HBC 7 with Magic Blue.

A solution of HBC 7 (3 mL, $1.5\times10^{-4}$ M) in electrolyte (benzonitrile, 0.10 M TBAPF$_6$) was prepared inside a dry box and added to a 1 cm screw-capped cuvette. A Magic Blue solution (15 mM in benzonitrile, 0.10 M TBAPF$_6$) was added in portions (6 μL each, 0.2 eq each) and UV-Vis-NIR spectra were obtained after each addition (450-1500 nm). After 1.0 equivalents, excess Magic Blue is observed, indicated by the emergence of a peak at $\lambda_{max}$=720 nm from the baseline. This indicates a quantitative one-electron oxidation to the HBC radical cation 8.

Zn powder (<5 mg) was added to the cuvette and the solution was shaken for 30 min. A spectrum was obtained from 450-1500 nm that shows no signal at higher wavelengths indicating complete, reversible reduction of 8. The mixture was then diluted 15-fold to $1.0\times10^{-5}$ M and a spectrum was obtained from 300-800 nm, which closely overlays with a spectrum of unreacted HBC 7 at the same concentration. The small difference in absorption is likely due to the presence of Zn(SbPF$_6$)$_2$ and tris(4-bromophenyl) amine. Addition of Zn(II) ions may enhance aggregation of HBC 7 by linking stacks of 7 through coordination of Zn(II) at the peripheral dimethylamido substituents. An increase in aggregation strength would manifest in the UV-Vis spectrum as a reduction in optical density around 350-450 nm.

Variable Temperature UV-Vis Spectroscopy.

All measurements were made in dual beam mode with an electrolyte reference (0.10 M TBAPF$_6$ in benzonitrile) held at the same temperature as the analyte. The temperature of both analyte and reference cuvettes was monitored internally and allowed to stabilize for five minutes prior to data collection. The concentration of 7 in electrolyte was 10 μM for the study of HBC assembly in a neutral state. A partially oxidized solution of HBC was prepared with a concentration of 7 in electrolyte of 10 μM followed by addition of 0.25 equivalents of Magic Blue from a concentrated stock solution (1.5 mM)

X-Ray Spectroscopy.

Samples of 7 were dropcast from EtOH (180 μM) onto Si wafers. XAS and XES spectra were collected at the Advanced Light Source Beamline 8.0.1. XAS spectra were recorded in total-electron-yield (TEY) mode by monitoring the sample drain current. The energy scale was calibrated to the π* peak at 285.5 eV in the XAS spectrum of highly oriented pyrolitic graphite (HOPG). XES spectra were collected using a Nordgren-type spectrometer.

IV Measurements.

Stock solutions of HBC (1.5 mM) and Magic Blue (375 μM, 750 μM, 1.875 mM, 3.75 mM, 7.5 mM) were prepared in 0.10 M TBAPF$_6$ in benzonitrile. 50 μL of HBC stock and 10 μL of MB stock were mixed and 4 μL of the final solution was added onto an interdigitated array (IDA). The IDA features 65 pairs of Au electrodes with width, length, and spacing of 10 μm, 2 mm, and 5 μm, respectively (CH Instruments, Austin, Tex., USA). The measurements were made with one set of electrodes connected to the working electrode lead and the other set connected to the reference and auxiliary leads of the potentiostat. The voltage was swept from $V_{oc}\pm0.2$ V at 20 mV/s.

Assessment of the electronic structure of HBC 7 in the condensed phase was provided by soft X-ray spectroscopy.[14] X-ray absorption (XAS) and X-ray emission (XES) spectra of HBC 7 were evaluated at the carbon K-edge to inform the energy level alignment for the unoccupied and occupied frontier molecular orbitals of the networked HBC, respectively; these orbitals are most closely associated with electronic charge transport. The HOMO-LUMO gap was calculated to be 1.85 eV, as determined by the difference between the highest and lowest energy peak in the first derivative of the XES and XAS spectra, respectively.

Additional insight into the nature of the molecular orbitals involved in charge transport through π-stacks of HBC 7 was obtained by density functional theory (DFT), where the alkyl side chains were truncated to methyl groups (see SI). Both the HOMO and LUMO are spread across the PAH π-core of the molecule. Extensive delocalization of the HOMO across the π-system helps to stabilize the radical cation as well as facilitates hopping through a network assembled through π-stacking. The calculated spin density of HBC·+8 also exhibits delocalization over the entire aromatic core.

Chemical doping is essential to enhance charge transport in self-assembled stacks of organic semiconductors; however, the phenomenon is rarely investigated in solution. Therefore, the chemical oxidation of HBC 7 in electrolyte was performed to probe the redox chemistry and transport behaviour of dynamic assemblies of HBC 7. Tris(4-bromophenyl)ammoniumyl hexachloroantimonate or "Magic Blue" (MB) was a superior oxidizing agent for generating HBC radical cations, owing to the presence of Lewis basic dimethylamides in HBC 7 (which were found to be incompatible with $SbCl_5$ and $NOBF_4$).[15] Controlled addition of MB to a solution of HBC 7 in electrolyte led to the growth of a peak at $\lambda_{max}=1025$ nm in the optical spectra, consistent with generation of a HBC radical cation. The intensity of the peak associated with HBC·+8 increased until one molar equivalent of MB was added, after which point excess MB was observed ($\lambda_{max}=721$ nm); this supports a quantitative one-electron oxidation. We also showed that the oxidation of HBC 7 to HBC·+8 is reversible; after addition of excess Zn powder, HBC 7 is observed by optical spectroscopy.

Self-assembly of HBC 7 in a partially oxidized state was interrogated by variable temperature optical spectroscopy. MB (0.25 eq.) was added to a solution of HBC 7 (10 μM in electrolyte) to form a 3:1 mixture of HBC 7:HBC·+8. Upon heating the solution from 30 to 90° C. changes consistent with a disassembly process are observed: sharpening of the spectral features and increased E. Isosbestic points are observed at 352.5, 358.0, 363.5, and 423 nm, indicating that only the one process is occurring (i.e., disassembly). The temperature induced changes are similar to those observed for neutral HBC 7 alone although the increase in optical density is more extreme for the mixed HBC 7:HBC·+ 8 system and the isosbestic points are shifted slightly.

By interchanging charge-neutral HBC subunits 7 with radical cation subunits 8 within the assembly, enhanced electronic transport should be possible via hopping.[16] This hypothesis was tested by measuring the shuttling current for HBC assemblies in solution with varying rations of HBC 7:HBC·+8. To evaluate the shuttling current, we carried out I-V measurements for electrolyte alone, charge-neutral HBC 7 assemblies, and HBC assemblies doped with controlled amounts of MB (1.25 mM HBC in benzonitrile with 0.10 M $TBAPF_6$). These measurements employed an interdigitated array (IDA) of Au microelectrodes. All IDA measurements were made with one set of electrodes connected to the working electrode lead and the other set connected to the reference and auxiliary leads of the potentiostat. The voltage bias was cycled over a ±0.2 V range from the open circuit potential. Self-assembled networks of charge-neutral HBC 7 show a negligible increase in current over electrolyte. On the other hand, as self-assembled networks of HBC 7 are oxidatively doped by the addition of MB a steady increase in shuttling current is observed up to a maximum current at a 1:1 ratio of HBC 7:HBC·+8. These results indicate that HBC 7 is able to transport charge as part of a supramolecular redox-active network in solution.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. An energy storage device comprising:
   an anode;
   a cathode comprising:
      a lithium sulfide $M_xS_y$, wherein M is lithium, subscript x is from 0 to 2 and y is from 1 to 8,
      a dissolved redox mediator, wherein the dissolved redox mediator is a benzoperyleneimide (BPI) of Formula II:

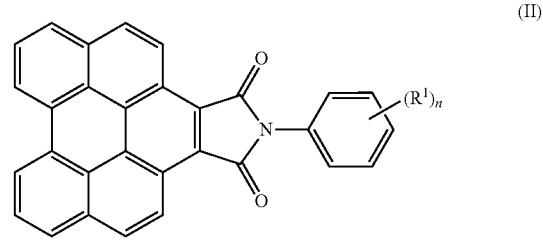

wherein
   each $R^1$ is independently selected from the group consisting of halogen, $C_{1-20}$ alkyl, $C_{1-20}$ haloalkyl, $C_{1-20}$ alkoxy, $C_{1-20}$ heteroalkyl, $C_{3-20}$ carbocycle, $C_{3-20}$ heterocycle, $C_{6-20}$ aryl, $C_{5-20}$ heteroaryl, —N($R^3$)($R^4$), —O$R^3$, —C(O)$R^3$, —C(O)O$R^3$, —OC(O)$R^3$, —C(O)N($R^3$)($R^4$), —N($R^3$)C(O)$R^4$, —N($R^3$)C(O)N($R^4$)($R^5$), —OC(O)N($R^4$)($R^5$), —N($R^3$)C(O)O$R^4$, —S$R^3$, —S(O)$R^3$, —S(O)$_2R^3$, —$N_3$, —B(O$R^3$)$_2$, and —Se$R^3$,
   alternatively, two $R^1$ groups on adjacent ring atoms can be combined to form —O(CH$_2$CH$_2$)$_m$O—, wherein subscript m is an integer from 3 to 10,
   each $R^3$, $R^4$ and $R^5$ is independently selected from the group consisting of H and $C_{1-20}$ alkyl, and
   subscript n is from 1 to 5,
   the BPI having a redox potential suitable for reducing or oxidizing lithium sulfide $M_xS_y$ or reducing elemental sulfur, and
   an electrolyte;
   a membrane separator between the anode and the cathode; and
   a current collector in electrical contact with the anode and cathode.

2. The energy storage device of claim 1, wherein the anode comprises lithium.

3. The energy storage device of claim 1, wherein the lithium sulfide comprises at least one of $Li_2S_8$ and $Li_2S_6$.

4. The energy storage device of claim 1, wherein the electrolyte comprises a metal salt.

5. The energy storage device of claim 4, wherein
   the cation of the metal salt is selected from the group consisting of lithium and sodium; and
   the anion of the metal salt is selected from the group consisting of bis(trifluoromethyl)sulfonimide, trifluoromethylsulfonate, fluorosulfonimide, perchlorate, tetrafluoroborate, hexafluorophosphate, nitrate, fluoride, chloride, bromide, and iodide.

6. The energy storage device of claim 1, wherein the electrolyte comprises at least one of diglyme, PGMEA, dimethoxyethane, triglyme, tetraglyme, dioxolane, THF, propylene carbonate, dimethylcarbonate, ethylene carbonate, ethyl methyl sulfone (EMS), propyl methyl sulfone (PMS), water, poly(ethylene oxide) and copolymers thereof, dimethylsulfoxide, N-methylpyrrolidinone, and acetonitrile.

7. The energy storage device of claim 1, wherein the cathode further comprises a conductive additive.

8. The energy storage device of claim 7, wherein the conductive additive comprises carbon.

9. The energy storage device of claim 1, wherein the current collector comprises at least one of carbon cloth, carbon felt, carbon paper, carbon particles, carbon nanomaterial, metal chalcogenide, metal, and metal oxide.

10. The energy storage device of claim 1, wherein:
the anode comprises lithium;
the lithium sulfide is $Li_2S_8$,
the BPI has the structure:

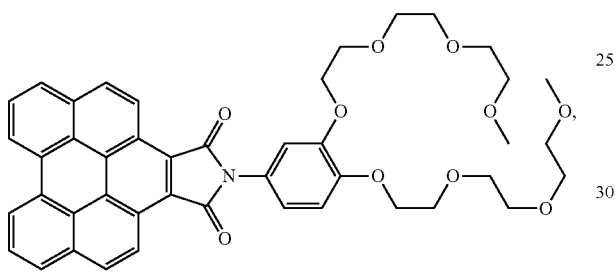

and
the electrolyte comprises diglyme, lithium bis(trifluoromethyl)sulfonamide, and lithium nitrate.

11. An electrode composition, comprising:
a lithium sulfide $M_xS_y$, wherein M is metal lithium, subscript x is from 0 to 2 and y is from 1 to 8;
a redox mediator, wherein the redox mediator is a benzoperyleneimide (BPI) of Formula II:

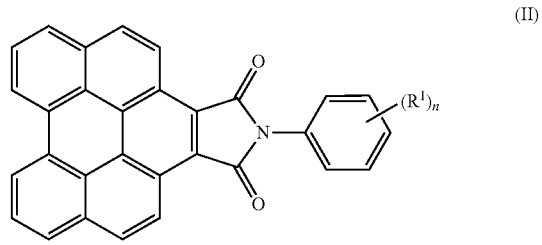

(II)

wherein
each $R^1$ is independently selected from the group consisting of halogen, $C_{1-20}$ alkyl, $C_{1-20}$ haloalkyl, $C_{1-20}$ alkoxy, $C_{1-20}$ heteroalkyl, $C_{3-20}$ carbocycle, $C_{3-20}$ heterocycle, $C_{6-20}$ aryl, $C_{5-20}$ heteroaryl, $—N(R^3)(R^4)$, $—OR^3$, $—C(O)R^3$, $—C(O)OR^3$, $—OC(O)R^3$, $—C(O)N(R^3)(R^4)$, $—N(R^3)C(O)R^4$, $—N(R^3)C(O)N(R^4)(R^5)$, $—OC(O)N(R^4)(R^5)$, $—N(R^3)C(O)OR^4$, $—SR^3$, $—S(O)R^3$, $—S(O)_2R^3$, $—N_3$, $—B(OR^3)_2$, and $—SeR^3$,
alternatively, two $R^1$ groups on adjacent ring atoms can be combined to form $—O(CH_2CH_2)_mO—$, wherein subscript m is an integer from 3 to 10, each $R^3$, $R^4$ and $R^5$ is independently selected from the group consisting of H and $C_{1-20}$ alkyl, and
subscript n is from 1 to 5,
the BPI having a redox potential suitable for reducing or oxidizing $M_xS_y$; and
an electrolyte.

* * * * *

UNITED STATES PATENT AND TRADEMARK OFFICE
CERTIFICATE OF CORRECTION

PATENT NO. : 10,727,488 B2
APPLICATION NO. : 15/502479
DATED : July 28, 2020
INVENTOR(S) : Brett A. Helms et al.

Page 1 of 1

It is certified that error appears in the above-identified patent and that said Letters Patent is hereby corrected as shown below:

In the Claims

In Column 42, Line 2, Claim 11, delete "metal"

Signed and Sealed this
Tenth Day of November, 2020

Andrei Iancu
*Director of the United States Patent and Trademark Office*